United States Patent
Wunberg et al.

(10) Patent No.: US 9,090,564 B2
(45) Date of Patent: Jul. 28, 2015

(54) 5-ALKYNYL-PYRIDINES

(71) Applicants: Tobias Wunberg, Hinterbruehl (AT); Siegfried Schneider, Vienna (AT); Lars Van Der Veen, Alsbach-Haehnlein (DE)

(72) Inventors: Tobias Wunberg, Hinterbruehl (AT); Siegfried Schneider, Vienna (AT); Lars Van Der Veen, Alsbach-Haehnlein (DE)

(73) Assignee: Boehringer Ingelheim International GmbH, Ingelheim am Rhein ( * ) Notice: Subject to any disclaimer, the term of this patent is extended or adjusted under 35 U.S.C. 154(b) by 0 days.

(21) Appl. No.: 13/795,722

(22) Filed: Mar. 12, 2013

(65) Prior Publication Data

US 2013/0196975 A1 Aug. 1, 2013

Related U.S. Application Data

(63) Continuation of application No. 12/763,434, filed on Apr. 20, 2010, now abandoned.

(30) Foreign Application Priority Data

Apr. 21, 2009 (EP) .................................. 09158327

(51) Int. Cl.
| | |
|---|---|
| C07D 213/73 | (2006.01) |
| C07D 401/14 | (2006.01) |
| C07D 405/14 | (2006.01) |
| C07D 413/14 | (2006.01) |
| C07D 487/08 | (2006.01) |
| C07D 471/04 | (2006.01) |

(52) U.S. Cl.
CPC ............ C07D 213/73 (2013.01); C07D 401/14 (2013.01); C07D 405/14 (2013.01); C07D 413/14 (2013.01); C07D 471/04 (2013.01); C07D 487/08 (2013.01)

(58) Field of Classification Search
CPC .............................. C07D 213/73; C07D 401/14
See application file for complete search history.

(56) References Cited

U.S. PATENT DOCUMENTS

| | | | |
|---|---|---|---|
| 2005/0245530 A1 | 11/2005 | Borzilleri et al. | |
| 2011/0230472 A1 | 9/2011 | Mitsuoka et al. | |

FOREIGN PATENT DOCUMENTS

| | | |
|---|---|---|
| JP | 2008528663 A | 7/2008 |
| JP | 2010510242 A | 4/2010 |
| JP | 2011529468 A | 12/2011 |
| WO | 2006044823 A2 | 4/2006 |
| WO | 2006082373 A1 | 8/2006 |
| WO | 2008061236 A2 | 5/2008 |
| WO | 2010012740 A1 | 2/2010 |
| WO | 2010024258 A1 | 3/2010 |

OTHER PUBLICATIONS

Aakeroy et al., Dalton Transactions, Dec. 2005, pp. 1627-1635.
Li et al., Bioorganic & Medicinal Chemistry Letters, vol. 16, 2006, pp. 2000-2007.
International Search repot, Form PCT/ISA/210, and Written Opinion, Form PCT/ISA/237, for corresponding PCT/EP2010/055293, Date of mailing Jul. 16, 2010.

*Primary Examiner* — Samira Jean-Louis
(74) *Attorney, Agent, or Firm* — Michael P. Morris; Alan R. Stempel

(57) ABSTRACT

The present invention encompasses compounds of general formula (1)

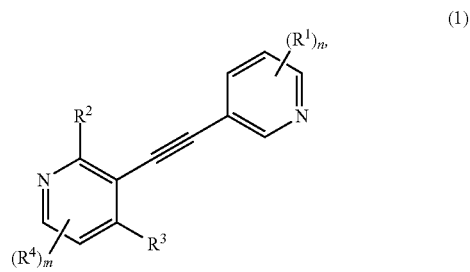

wherein
$R^1$ to $R^4$, m and n are defined as in the specification, which are suitable for the treatment of diseases characterized by excessive or abnormal cell proliferation, and the use thereof for preparing a medicament having the above-mentioned properties.

10 Claims, No Drawings

5-ALKYNYL-PYRIDINES

The present invention relates to new 5-alkynyl-pyridines of general formula (1)

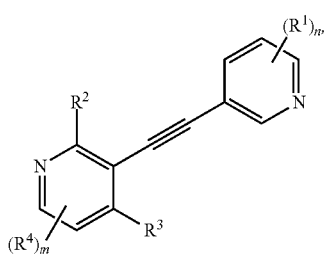

(1)

wherein the groups $R^1$ to $R^4$, m and n have the meanings given below, the isomers thereof, processes for preparing these alkynyl-pyrimidines and their use as medicaments.

BACKGROUND OF THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

The phosphoinositide 3-kinase (PI3K) pathway is activated in a broad spectrum of human cancers. This may occur either via mutation of PI3K resulting in activation of the kinase, or indirectly via inactivation of the phosphotase and tensin homologue (PTEN) suppressor. In both cases, an activation of the signalling cascade is induced that promotes transformation of cells both in vitro and in vivo. Within the cascade, the PI3K family of enzymes and the kinase mTOR play a pivotal role. The PI3K family comprises 15 lipid kinases with distinct substrate specificities, expression pattern and modes of regulation. They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories. The mammalian target of rapamycin (mTOR) is a serine/threonine kinase related to the lipide kinases of the PI3-kinase family. It exists in two complexes, mTORC1 and mTORC2, which are differentially regulated, have distinct substrate specificities, and are differentially sensitive to rapamycin. The central role of mTOR in controlling key cellular growth and survival pathways has sparked interest in discovering mTOR inhibitors that bind to the ATP site and therefore target both mTORC2 and mTORC1. As a consequence, inhibition of the PI3K pathway, particularly mediated via PI3Kα and mTOR, has emerged as an attractive target for cancer therapeutics. play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

5-Alkynyl-pyrimidines are described for example as protein kinases inhibiting compounds in WO2006044823.

DETAILED DESCRIPTION OF THE INVENTION

It has now surprisingly been found that compounds of general formula (1), wherein the groups $R^1$ to $R^4$, m and n have the meanings given below, act as inhibitors of kinases. Thus, the compounds according to the invention may be used for example for the treatment of diseases connected with the activity of kinases and characterised by excessive or abnormal cell proliferation.

The present invention relates to compounds of general formula (1)

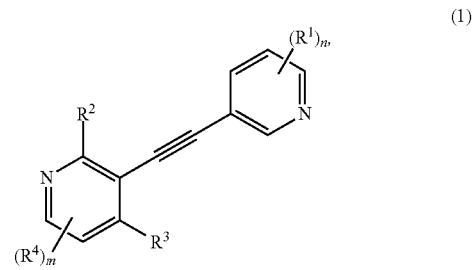

(1)

wherein
$R^1$ and $R^4$ independently from one another denotes a group selected from among $R^a$, $R^b$ and $R^a$ substituted by one or more identical or different $R^b$ and/or $R^c$; or
one $R^1$ together with the pyridine form a 9-10 membered heteroaryl ring, which is optionally substituted with one or more identical or different $R^b$ and/or $R^c$; and
$R^2$ and $R^3$ independently from one another denotes a group selected from among $C_{1-6}$alkyl, $C_{3-8}$cycloalkyl, 3-8 membered heterocycloalkyl, $C_{6-10}$aryl and 5-12 membered heteroaryl, optionally substituted by one or more identical or different $R^5$ and
each $R^5$ denotes a group selected from among $R^a$, $R^b$ and $R^a$ substituted by one or more identical or different $R^b$ and/or $R^c$; and
each $R^a$ independently of one another denotes a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^b$ denotes a suitable group and is selected independently of one another from among =O, —$OR^c$, $C_{1-3}$haloalkyloxy, —$OCF_3$, =S, —$SR^c$, =$NR^c$, =$NOR^c$, =$NNR^c$$R^c$, =NN($R^g$)C(O)$NR^cR^c$, —$NR^cR^c$, —$ONR^cR^c$, —N($OR^c$)$R^c$, —N($R^g$)$NR^cR^c$, halogen, —$CF_3$, —CN, —NC, —OCN, —SCN, —NO, —$NO_2$, =$N_2$, —$N_3$, —S(O)$R^c$, —S(O)$OR^c$, —$S(O)_2R^c$, —$S(O)_2OR^c$, —S(O)$NR^cR^c$, —$S(O)_2NR^cR^c$, —OS(O)$R^c$, —$OS(O)_2R^c$, —$OS(O)_2OR^c$, —OS(O)$NR^cR^c$, —$OS(O)_2NR^cR^c$, —C(O)$R^c$, —C(O)$OR^c$, —C(O)$SR^c$, —C(O)$NR^cR^c$, —C(O)N($R^g$)$NR^cR^c$, —C(O)N($R^g$)$OR^c$, —C($NR^g$)$NR^cR^c$, —C(NOH)$R^c$, —C(NOH)$NR^cR^c$, —OC(O)$R^c$, —OC(O)$OR^c$, OC(O)$SR^c$, —OC(O)$NR^cR^c$, —OC($NR^g$)$NR^cR^c$, —SC(O)$R^c$, —SC(O)$OR^c$, —SC(O)$NR^cR^c$, —SC($NR^g$)$NR^cR^c$, —N($R^g$)C(O)$R^c$, —N[C(O)$R^c$]$_2$, —N($OR^g$)C(O)$R^c$, —N($R^g$)C($NR^g$)$R^c$, —N($R^g$)N($R^g$)C(O)

$R^c$, —N[S(O)$R^c$]$_2$NR$^c$R$^c$, —N($R^g$)C(S)$R^c$, —N($R^g$)S(O)$R^c$, —N($R^g$)S(O)O$R^c$, —N($R^g$)S(O)$_2$$R^c$, —N[S(O)$_2$$R^c$]$_2$, —N($R^g$)S(O)$_2$O$R^c$, —N($R^g$)S(O)$_2$NR$^c$R$^c$, —N($R^g$)[S(O)$_2$]$_2$$R^c$, —N($R^g$)C(O)O$R^c$, —N($R^g$)C(O)S$R^c$, —N($R^g$)C(O)NR$^c$R$^c$, —N($R^g$)C(O)NR$^g$NR$^c$R$^c$, —N($R^g$)N($R^g$)C(O)NR$^c$R$^c$, —N($R^g$)C(S)NR$^c$R$^c$, —[N($R^g$)C(O)]$_2$$R^c$, —N($R^g$)[C(O)]$_2$$R^c$, —N{[C(O)]$_2$$R^c$}$_2$, —N($R^g$)[C(O)]$_2$O$R^c$, —N($R^g$)[C(O)]$_2$NR$^c$R$^c$, —N{[C(O)]$_2$O$R^c$}$_2$, —N{[C(O)]$_2$NR$^c$R$^c$}$_2$, —[N($R^g$)C(O)]$_2$O$R^c$, —N($R^g$)C(N$R^g$)O$R^c$, —N($R^g$)C(NOH)$R^c$, —N($R^g$)C(N$R^g$)S$R^c$, —N($R^g$)C(N$R^g$)NR$^c$R$^c$ and —N=C($R^g$)NR$^c$R$^c$ and each $R^c$ independently of one another denotes hydrogen or a group optionally substituted by one or more identical or different $R^d$ and/or $R^e$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each $R^d$ denotes a suitable group and is selected independently of one another from among =O, —O$R^e$, C$_{1-3}$haloalkyloxy, —OCF$_3$, =S, —S$R^e$, =N$R^e$, =NO$R^e$, =NN$R^e$$R^e$, =NN($R^g$)C(O)NR$^e$R$^e$, —NR$^e$R$^e$, —ONR$^e$R$^e$, —N($R^g$)NR$^e$R$^e$, halogen, —CF$_3$, —CN, —NC, —OCN, —SCN, —NO, —NO$_2$, =N$_2$, —N$_3$, —S(O)$R^e$, —S(O)O$R^e$, —S(O)$_2$$R^e$, —S(O)$_2$O$R^e$, —S(O)NR$^e$R$^e$, —S(O)$_2$NR$^e$R$^e$, —OS(O)$R^e$, —OS(O)$_2$$R^e$, —OS(O)$_2$O$R^e$, —OS(O)NR$^e$R$^e$, —OS(O)$_2$NR$^e$R$^e$, —C(O)$R^e$, —C(O)O$R^e$, —C(O)S$R^e$, —C(O)NR$^e$R$^e$, —C(O)N($R^g$)NR$^e$R$^e$, —C(O)N($R^g$)O$R^e$, —C(N$R^g$)NR$^e$R$^e$, —C(NOH)$R^e$, —C(NOH)NR$^e$R$^e$, —OC(O)$R^e$, —OC(O)O$R^e$, —OC(O)S$R^e$, —OC(O)NR$^e$R$^e$, —OC(N$R^g$)NR$^e$R$^e$, —SC(O)$R^e$, —SC(O)O$R^e$, —SC(O)NR$^e$R$^e$, —SC(N$R^g$)NR$^e$R$^e$, —N($R^g$)C(O)$R^e$, —N[C(O)$R^e$]$_2$, —N(O$R^g$)C(O)$R^e$, —N($R^g$)C(N$R^g$)$R^e$, —N($R^g$)N($R^g$)C(O)$R^e$, —N[C(O)$R^e$]NR$^e$R$^e$, —N($R^g$)C(S)$R^e$, —N($R^g$)S(O)$R^e$, —N($R^g$)S(O)O$R^e$, —N($R^g$)S(O)$_2$$R^e$, —N[S(O)$_2$$R^e$]$_2$, —N($R^g$)S(O)$_2$O$R^e$, —N($R^g$)S(O)$_2$NR$^e$R$^e$, —N($R^g$)[S(O)$_2$]$_2$$R^e$, —N($R^g$)C(O)O$R^e$, —N($R^g$)C(O)S$R^e$, —N($R^g$)C(O)NR$^e$R$^e$, —N($R^g$)C(O)NR$^g$NR$^e$R$^e$, —N($R^g$)N($R^g$)C(O)NR$^e$R$^e$, —N($R^g$)C(S)NR$^e$R$^e$, —[N($R^g$)C(O)]$_2$$R^e$, —N($R^g$)[C(O)]$_2$$R^e$, —N{[C(O)]$_2$$R^e$}$_2$, —N($R^g$)[C(O)]$_2$O$R^e$, —N($R^g$)[C(O)]$_2$NR$^e$R$^e$, —N{[C(O)]$_2$O$R^e$}$_2$, —N{[C(O)]$_2$NR$^e$R$^e$}$_2$, —[N($R^g$)C(O)]$_2$O$R^e$, —N($R^g$)C(N$R^g$)O$R^e$, —N($R^g$)C(NOH)$R^e$, —N($R^g$)C(N$R^g$)S$R^e$, —N($R^g$)C(N$R^g$)NR$^e$R$^e$ and —N=C($R^g$)NR$^e$R$^e$ and each $R^e$ independently of one another denotes hydrogen or a group optionally substituted by one or more identical or different $R^f$ and/or $R^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —O$R^g$, C$_{1-3}$haloalkyloxy, —OCF$_3$, =S, —S$R^g$, =N$R^g$, =NO$R^g$, =NN$R^g$$R^g$, =NN($R^h$)C(O)NR$^g$R$^g$, —NR$^g$R$^g$, —ONR$^g$R$^g$, —N($R^h$)NR$^g$R$^g$, halogen, —CF$_3$, —CN, —NC, —OCN, —SCN, —NO, —NO$_2$, =N$_2$, —N$_3$, —S(O)$R^g$, —S(O)O$R^g$, —S(O)$_2$$R^g$, —S(O)$_2$O$R^g$, —S(O)NR$^g$R$^g$, —S(O)$_2$NR$^g$R$^g$, —OS(O)$R^g$, —OS(O)$_2$$R^g$, —OS(O)$_2$O$R^g$, —OS(O)NR$^g$R$^g$, —OS(O)$_2$NR$^g$R$^g$, —C(O)$R^g$, —C(O)O$R^g$, —C(O)S$R^g$, —C(O)NR$^g$R$^g$, —C(O)N($R^h$)NR$^g$R$^g$, —C(O)N($R^h$)O$R^g$, —C(N$R^h$)NR$^g$R$^g$, —C(NOH)$R^g$, —C(NOH)NR$^g$R$^g$, —OC(O)$R^g$, —OC(O)O$R^g$, —OC(O)S$R^g$, —OC(O)NR$^g$R$^g$, —OC(N$R^h$)NR$^g$R$^g$, —SC(O)$R^g$, —SC(O)O$R^g$, —SC(O)NR$^g$R$^g$, —SC(N$R^h$)NR$^g$R$^g$, —N($R^h$)C(O)$R^g$, —N[C(O)$R^g$]$_2$, —N(O$R^h$)C(O)$R^g$, —N($R^h$)C(N$R^h$)$R^g$, —N($R^h$)N($R^h$)C(O)$R^g$, —N[C(O)$R^g$]NR$^g$R$^g$, —N($R^h$)C(S)$R^e$, —N($R^h$)S(O)$R^e$, —N($R^h$)S(O)O$R^g$, —N($R^h$)S(O)$_2$$R^g$, —N[S(O)$_2$$R^g$]$_2$, —N($R^h$)S(O)$_2$O$R^g$, —N($R^h$)S(O)$_2$NR$^g$R$^g$, —N($R^h$)[S(O)$_2$]$_2$$R^g$, —N($R^h$)C(O)O$R^g$, —N($R^h$)C(O)S$R^g$, —N($R^h$)C(O)NR$^g$R$^g$, —N($R^h$)C(O)NR$^h$NR$^g$R$^g$, —N($R^h$)N($R^h$)C(O)NR$^g$R$^g$, —N($R^h$)C(S)NR$^g$R$^g$, [N($R^h$)C(O)]$_2$$R^g$, —N($R^h$)[C(O)]$_2$$R^g$, —N{[C(O)]$_2$$R^g$}$_2$, —N($R^h$)[C(O)]$_2$O$R^g$, —N($R^h$)[C(O)]$_2$NR$^g$R$^g$, —N{[C(O)]$_2$O$R^g$}$_2$, —N{[C(O)]$_2$NR$^g$R$^g$}$_2$, —[N($R^h$)C(O)]$_2$O$R^g$, —N($R^h$)C(N$R^h$)O$R^g$, —N($R^h$)C(NOH)$R^g$, —N($R^h$)C(N$R^h$)S$R^g$, —N($R^h$)C(N$R^h$)NR$^g$R$^e$; and —N=C($R^g$)NR$^e$R$^e$; and each $R^g$ independently of one another denotes hydrogen or a group optionally substituted by one or more identical or different $R^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each $R^h$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl; and m denotes 0, 1 or 2; and n denotes 0, 1, 2 or 3; and optionally in the form of the prodrugs, the tautomers, the racemates, the enantiomers, the diastereomers, the prodrugs and the mixtures thereof, and optionally the pharmacologically acceptable salts thereof.

One aspect of the invention relates to compounds of general formula (1), wherein $R^3$ denotes C$_{6-10}$aryl or 5-12 membered Heteroaryl, optionally substituted by one or more identical or different $R^5$.

Another aspect of the invention relates to compounds of general formula (1), wherein $R^3$ denotes phenyl, optionally substituted by one or more identical or different $R^5$.

Another aspect of the invention relates to compounds of general formula (1), wherein $R^3$ denotes pyridyl, optionally substituted by one or more identical or different $R^5$.

Another aspect of the invention relates to compounds of general formula (1), wherein $R^3$ denotes pyrazolyl, optionally substituted by one or more identical or different $R^5$.

Another aspect of the invention relates to compounds of general formula (1), wherein $R^2$ denotes methyl or ethyl.

Another aspect of the invention relates to compounds of general formula (1), wherein n denotes 1 or 2.

Another aspect of the invention relates to compounds of general formula (1), wherein $R^1$ denotes methyl, ethyl or —NR$^c$R$^c$.

Another aspect of the invention relates to compounds of general formula (1), wherein $R^1$ is selected from —NH$_2$, —NH—CH$_3$ and —N(CH$_3$)$_2$.

Another aspect of the invention relates to compounds of general formula (1), wherein le is selected from hydrogen, methyl, ethyl and cyclopropyl.

Another aspect of the invention relates to compounds of general formula (1), wherein $R^b$ is selected from —F, —CH$_3$, —OCH$_3$, —CF$_3$, —C(O)—$R^c$, —C(O)NR$^c$R$^c$, —C(O)OH, —C(O)OCH$_3$, —C(O)—NH$_2$, —C(O)—NHCH$_3$, —C(O)—N(CH$_3$)$_2$, —S(O)$_2$CH$_3$, -2-propyl-$R^c$.

Another aspect of the invention relates to compounds of general formula (1), wherein $R^c$ is selected from —H, —CN, -methyl, -ethyl, —(CH$_2$)$_2$—OCH$_3$, piperazinyl, piperidinyl, pyrrolidinyl and morpholinyl.

Another aspect of the invention relates to compounds of general formula (1), wherein $R^3$ is phenyl substituted with one or more $R^5$, wherein at least one of $R^5$ is —C(O)$R^c$ and wherein $R^c$ is

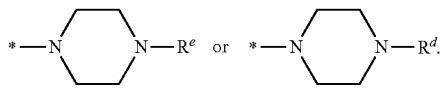

Another aspect of the invention relates to compounds of general formula (1), wherein $R^d$ is selected from —H, -methyl, -ethyl, -propyl, —OH, —OCH$_3$, and —C(O)CH$_3$.

Another aspect of the invention relates to compounds of general formula (1), wherein $R^c$ is selected from -cyclopropyl, cyclopentyl, oxiranyl, tetrahydropyranyl, and morpholinyl.

Another aspect of the invention relates to compounds of general formula (1), wherein $R^3$ is selected from the group consisting of:

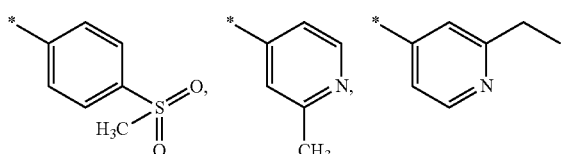

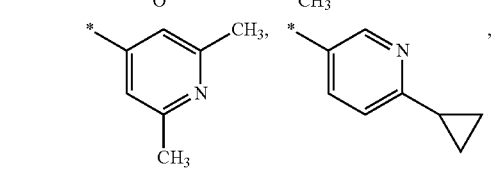

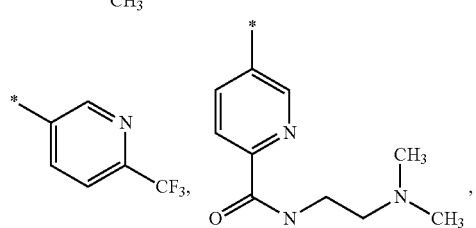

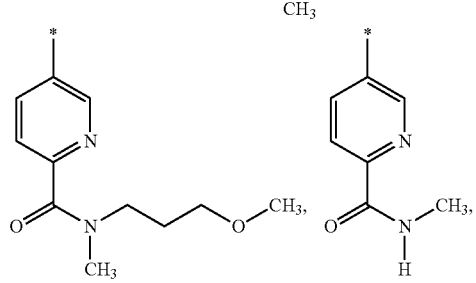

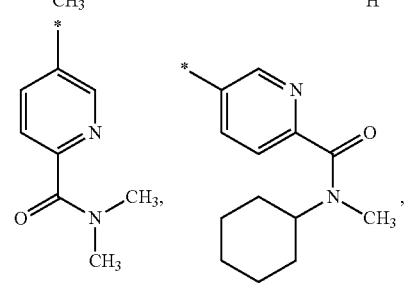

-continued

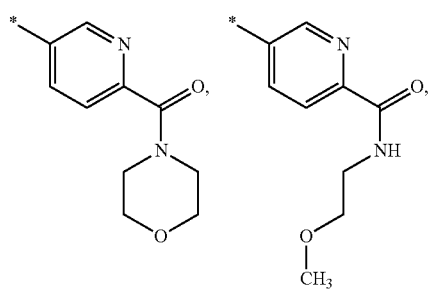

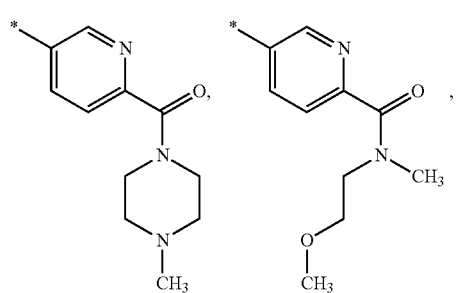

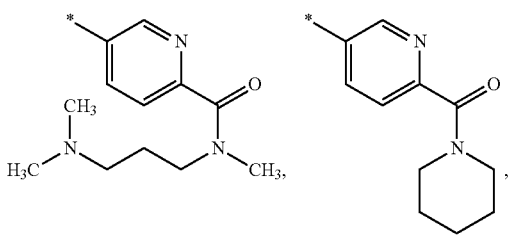

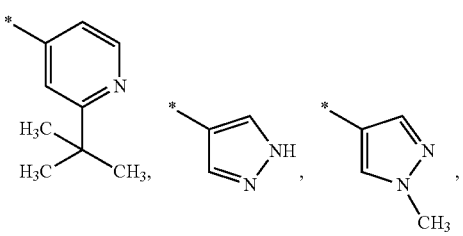

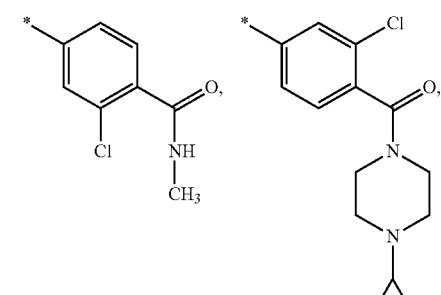

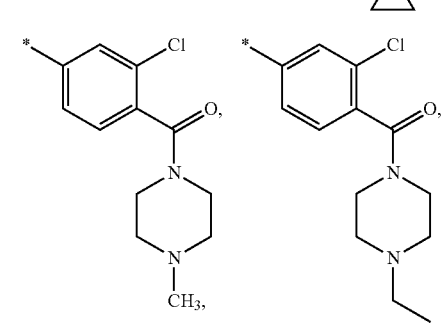

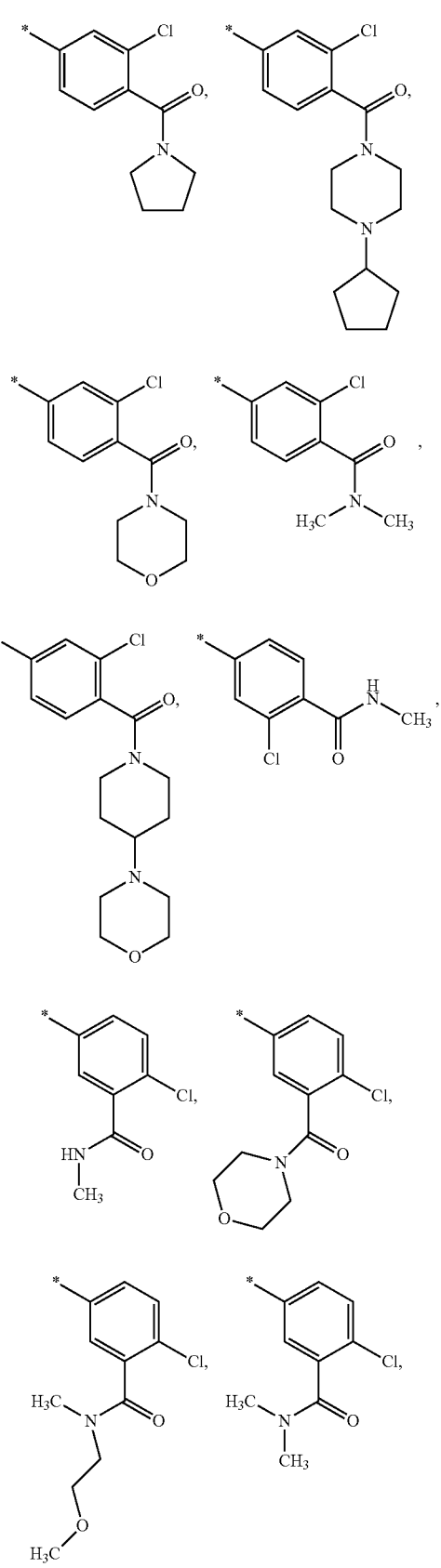
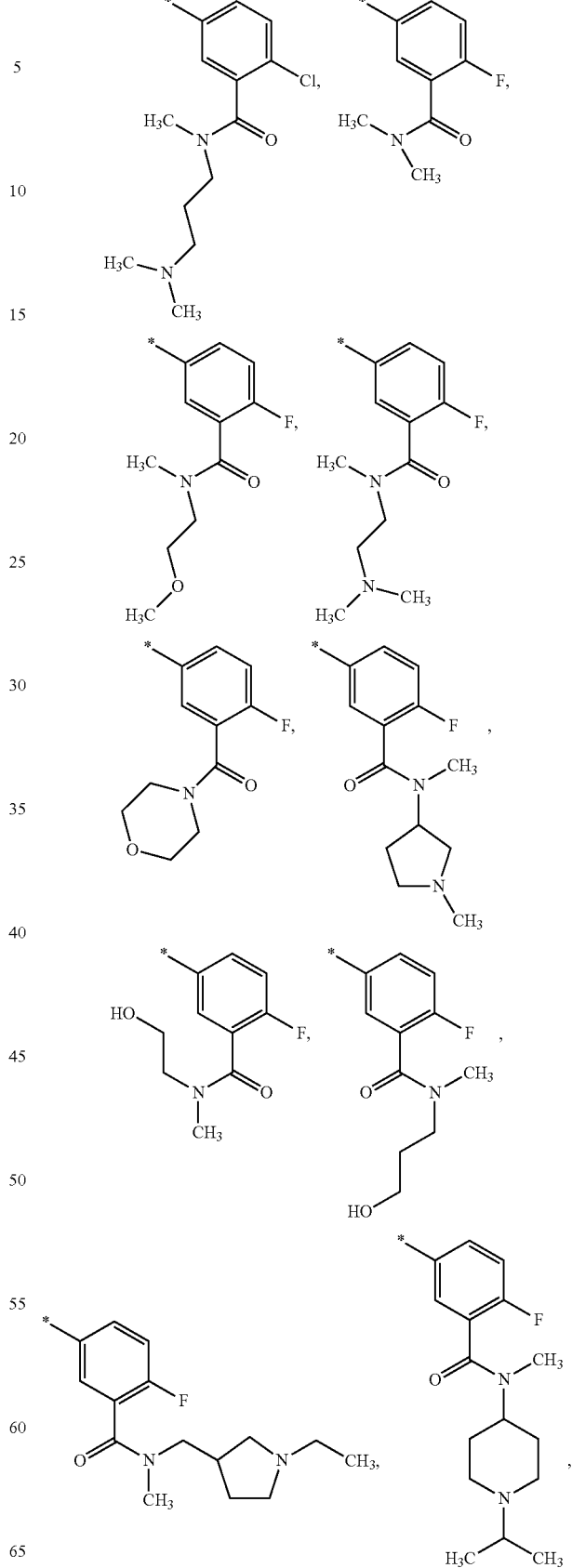

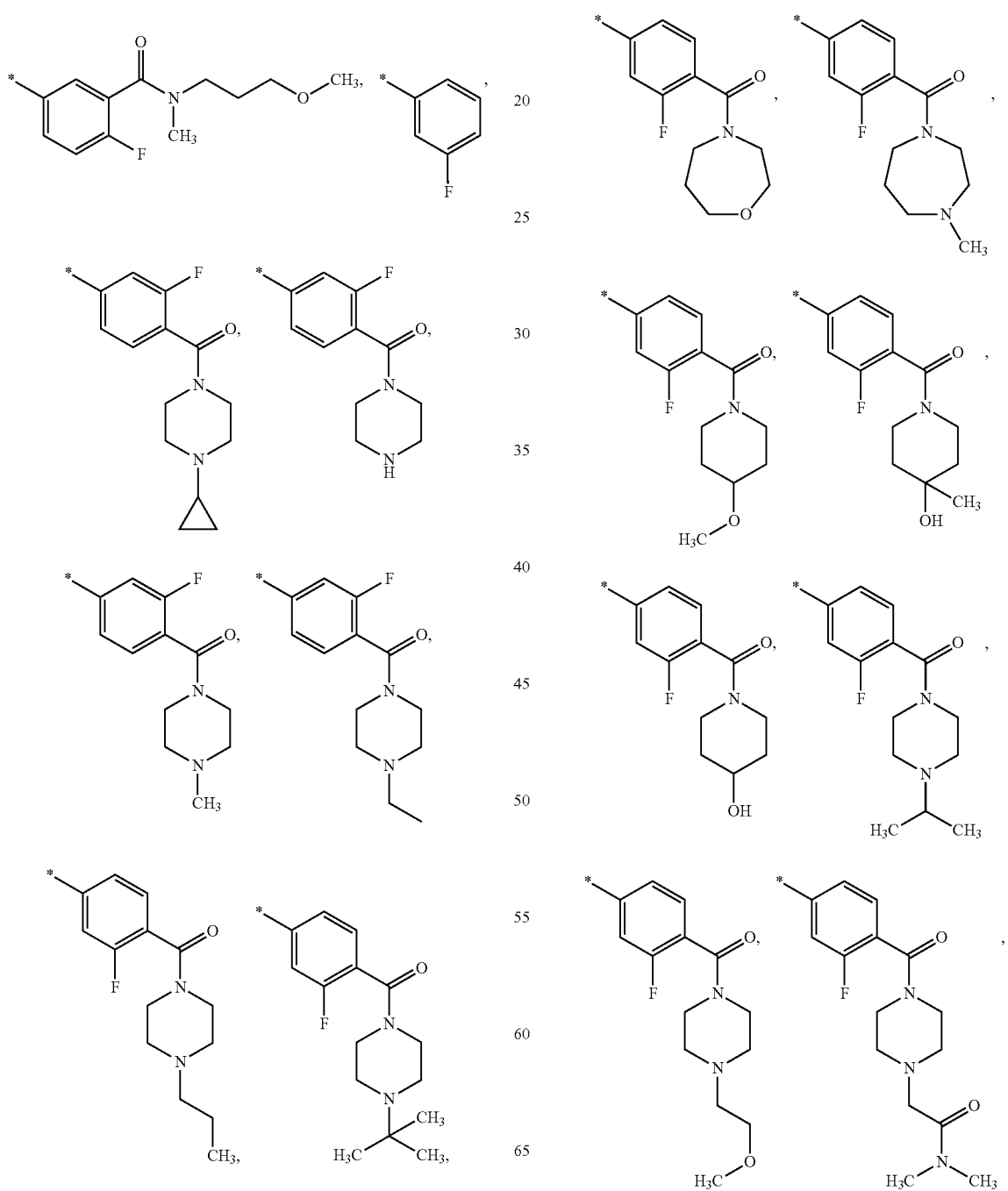

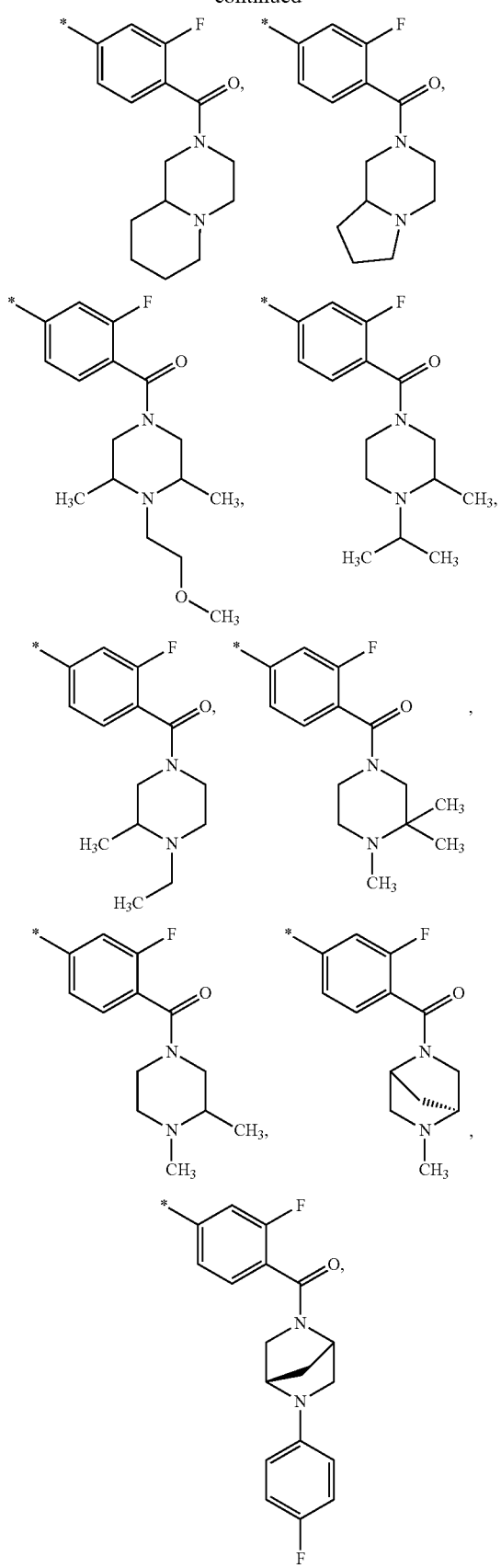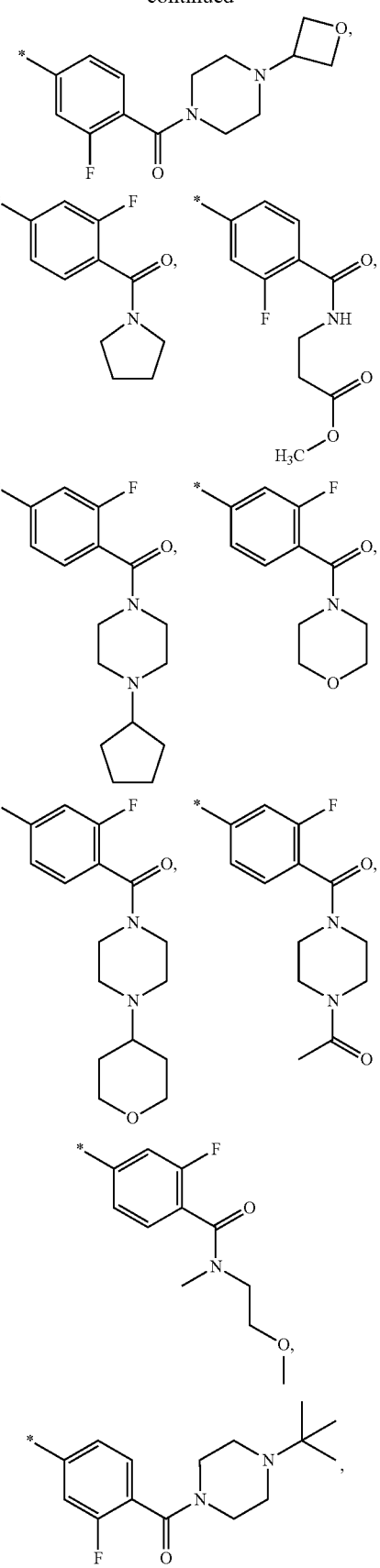

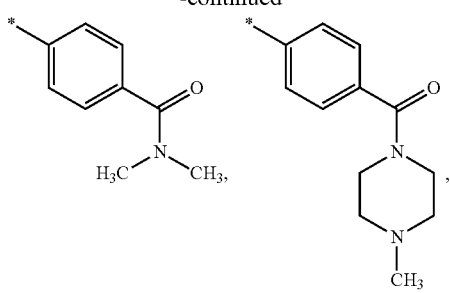
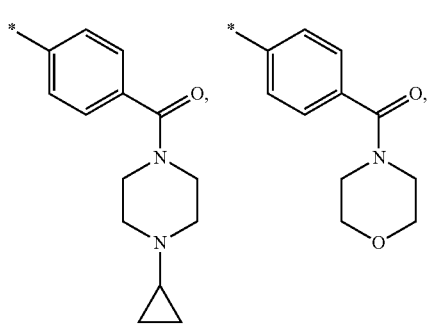
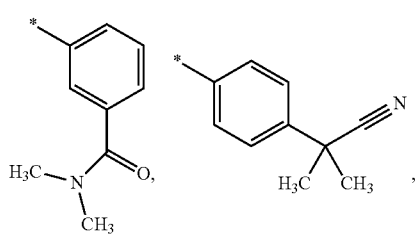
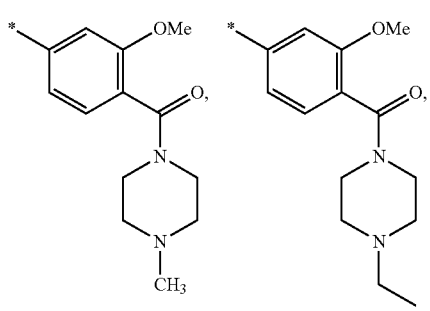
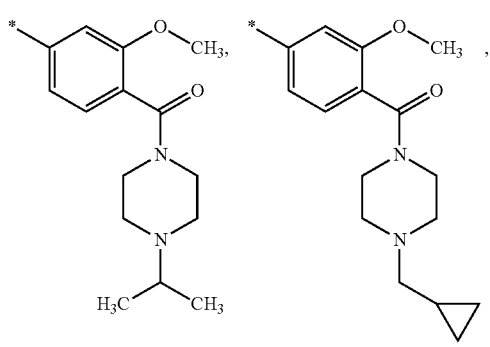
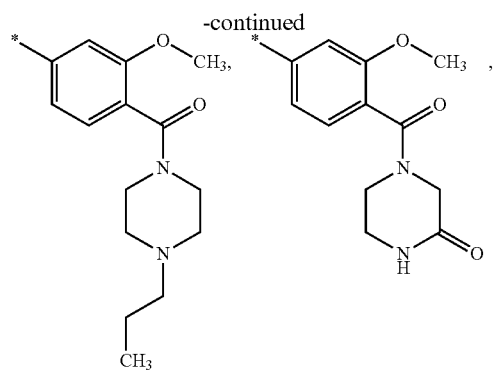

One aspect of the invention relates to compounds of general formula (1), or the pharmacologically effective salts thereof, as medicaments.

One aspect of the invention relates to compounds of general formula (1), or the pharmacologically effective salts thereof, for preparing a medicament with an antiproliferative activity.

One aspect of the invention is a pharmaceutical preparations, containing as active substance one or more compounds of general formula (1), or the pharmacologically effective salts thereof, optionally in combination with conventional excipients and/or carriers.

One aspect of the invention is the use of compounds of general formula (1) for preparing a medicament for the treatment and/or prevention of cancer, infections, inflammatory and autoimmune diseases.

One aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, as well as optionally the pharmacologically acceptable salts thereof.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —CH$_3$ in the hydrocarbon chains independently of one another by the groups —OH, —SH or —NH$_2$, one or more of the groups —CH$_2$— independently of one another by the groups —O—, —S— or —NH—, one or more of the groups

by the group

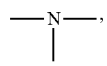

one or more of the groups ═CH— by the group ═N—, one or more of the groups ═CH₂ by the group ═NH or one or more of the groups ≡CH by the group ≡N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF═CF₂, —CCl═CH₂, —CBr═CH₂, —CI═CH₂, —C≡C—CF₃, —CHFCH₂CH₃ and —CHFCH₂CF₃.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, benzopyrazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocycloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-aza-bicyclo[3.2.1]octane, 3.8-diaza-bicyclo[3.2.1]octane, 2,5-diaza-bicyclo[2.2.1]heptane, 3.8-diaza-bicyclo[3.2.1]octane, 3.9-diaza-bicyclo[4.2.1]nonane and 2.6-diaza-bicyclo[3.2.2]nonane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

General Procedure GP1: Sonogashira Reaction

The halide (1.0 eq.) is dissolved in DMF or THF and PdCl₂(PPh₃)₂ (0.1 eq.) and CuI (0.1 eq.) are added. Subsequently, triethylamine (10.0 eq.) and finally the alkyne (1.5 eq.) are added and the reaction mixture is stiffed at 55-65° C.

The reaction is monitored by LC-MS. If the iodide is not completed converted after 4 h, additional amounts of alkyne are added in small portions.

General Procedure GP2: Desilylation of Alkynes

The TMS-alkyne (1.0 eq.) is dissovled in MeOH, $K_2CO_3$ (0.5 eq.) is added in one portion and the reaction mixture is stirred at room temperature until conversion is complete (3-16 h). The solvent is removed in vaccuo, the crude product is dissolved in ethyl acetate and the organic phase is extracted with water. The organic phase is dried over $MgSO_4$, filtered off and the solvent removed in vaccuo. The product is either used without further purification or purified by chromatography on silica gel using DCM/MeOH or (cyclo-) hexane/ethyl acetate.

General Procedure GP3: Suzuki Coupling

The 4-chloropyridine (1.0 eq.) is taken up in dioxane, boronic acid (2.0 eq.), $K_3PO_4$ (1.2 eq.), $Pd_2(dba)_3$ (0.1 eq.) and Dicyclohexyl(2',4',6'-thisopropylbiphenyl-2-yl)phosphan ("X-Phos", 0.3 eq.) are added and the reaction mixture is stirred either for 3-16 h under reflux or alternatively for 60-180 min at 150° C. under microwave radiation. In case the conversion of the starting material is not complete, additional amounts of boronic acid and Pd-catalyst are added and the reaction is re-run.

General Procedure GP4: Saponification of Esters

The ester is taken up in either THF or dioxane, 1.0-2.0 eq. of 1 N NaOH are added and the mixture is heated under reflux until reaction control shows complete conversion of the starting material. The product either precipitates from the reaction mixture (e.g. after acidification) and is used without additional purification steps or can further be purified by chromatography.

General Procedure 5 (GP5): Amide Formation with Amines

To a mixture of 0.21 mmol starting material, 0.31 mmol TBTU or HATU and 0.42 mmol Huenig's base in 2 mL DMSO or THF or NMP is stirred for 5 min 0.31 mmol of amine is added and the resultant mixture is stirred at RT over night. Purification is performed via preparative RP-HPLC or chromatography on silica gel yielding after evaporation of the solvent the desired product.

General Procedure 6 (GP6) Amide Formation with Acid Chlorides

To a mixture of 0.13 mmol of starting material and 67 μL Huenig's base in 2 mL THF is added 0.26 mmol acid chloride. The reaction mixture is stirred over night at RT. The solvent is evaporated and the residue is taken up in 1 mL DMSO insoluble material is filtered off and the resulting solution is purified via preparative RP-HPLC or chromatography on silica gel yielding after evaporation of the solvent the desired product.

General Procedure 7 (GP7): Urea Formation with Isocyanates

To a mixture of 0.16 mmol of starting material and 64.4 μL Huenig's base in 2 mL THF is added 0.49 mmol isocyanate. The reaction mixture is stirred over night at RT. The solvent is evaporated and the residue is taken up in 1 mL DMSO. Insoluble material is filtered off and the resulting solution is purified via preparative RP-HPLC or chromatography on silica gel yielding after evaporation of the solvent the desired product.

General Procedure 8 (GP8): Urea Formation Via Pre-Activation of the Amine

To a mixture of 0.34 mmol amine and 0.34 mmol N,N'-carbonyldiimidazole and 0.34 mmol 1,8-diazabicyclo[5.4.0]undec-7-ene is stirred for 10 min at RT. 0.32 mmol of starting material are added in one portion. The reaction mixture is heated at 100° C. for 1 h in the microwave. The solvent is evaporated and the residue is taken up in 1 mL DMSO, insoluble material is filtered off and the resulting solution is purified via preparative RP-HPLC or chromatography on silica gel yielding the desired product.

General Procedure 9 (GP9): Amide Formation with Carbonic Acids

To a mixture of 0.62 mmol carbonic acid, 0.93 mmol TBTU and 1.2 mmol Huenig's base in 2 mL DMSO is stiffed for 5 min 0.31 mmol of starting material is added and the resultant mixture is stirred at RT over night. Purification is performed via preparative RP-HPLC or chromatography on silica gel yielding after evaporation of the solvent the desired product.

Intermediates A

A-1) 5-Iodo-3-trifluoromethyl-pyridin-2-ylamine

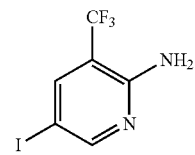

The title compound is synthesized according to general procedure GP1 starting from 5.0 g (31 mmol) 3-trifluoro-2-amino pyridine and 6.9 g (31 mmol) NIS. Yield after precipitation from the reaction mixture: 6.78 g (76%).

A-2) 2-Methyl-5-trimethylsilanylethynyl-pyridine

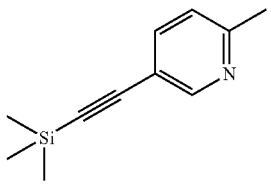

The title compound is synthesized according to general procedure GP2 starting from 2.0 g (11.6 mmol) 5-bromo-2-methyl-pyridine and 2.3 mL (16.3 mmol) 1-trimethylsilyl-ethyne using 68 mg (0.36 mmol) CuI, 305 mg (1.2 mmol) triphenylphosphine, 213 mg (0.30 mmol) $PdCl_2(PPh_3)_2$ and 18 mL (127 mmol) triethylamine in 18 mL dry THF. For the work-up the reaction mixture is diluted with ethyl acetate, the organic phase is extracted with water and brine. The product is purified by chromatography on silica gel using a hexane/ethyl acetate gradient. Yield: 1.5 g (68%). Note: Sublimation of the product is observed at 40° C./40 mbar.

A-3) 5-Trimethylsilanylethynyl-pyridin-2-ylamine

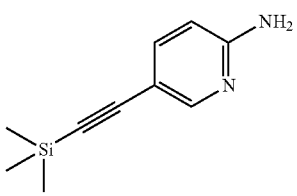

The title compound is synthesized according to general procedure GP2 starting from 5.0 g (28.9 mmol) 5-bromo-2- amino-pyridine and 5.7 mL (40.5 mmol) 1-trimethylsilyl-ethyne using 168 mg (0.88 mmol) CuI, 758 mg (2.9 mmol) triphenylphosphine, 533 mg (0.76 mmol) PdCl$_2$(PPh$_3$)$_2$ and 40 mL (288 mmol) triethylamine in 40 mL dry THF. For the work-up the reaction mixture is diluted with ethyl acetate and small amounts of cyclohexane, the organic phase is extracted with water and brine. The product is purified by chromatography on silica gel using hexane/ethyl acetate (10/1 v/v). Yield: 5.0 g (91%).

A-4) Methyl-(5-trimethylsilanylethynyl-pyridin-2-yl)-amine

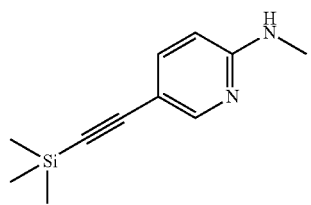

The title compound is synthesized according to general procedure GP2 starting from 4.3 g (23.0 mmol) 5-bromo-2-methylamino-pyridine and 4.5 mL (32.2 mmol) 1-trimethylsilyl-ethyne using 134 mg (0.71 mmol) CuI, 601 mg (2.3 mmol) triphenylphosphine, 420 mg (0.60 mmol) PdCl$_2$(PPh$_3$)$_2$ and 32 mL (101 mmol) triethylamine in 40 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient. Yield: 4.0 g (85%). Note: Sublimation of the product is observed at 40° C./40 mbar.

A-5) Ethyl-(5-trimethylsilanylethynyl-pyridin-2-yl)-amine

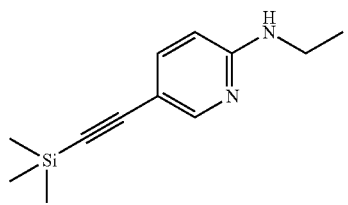

The title compound is synthesized according to general procedure GP2 starting from 909 mg (4.5 mmol) 5-bromo-2-ethylamino-pyridine and 0.89 mL (6.3 mmol) 1-trimethylsilyl-ethyne using 26 mg (0.13 mmol) CuI, 118 mg (0.45 mmol) triphenylphosphine, 82 mg (0.12 mmol) PdCl$_2$(PPh$_3$)$_2$ and 6.3 mL (45.0 mmol) triethylamine in 7 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient.

Yield: 980 mg (99%).

A-6) 5-Trimethylsilanylethynyl-pyridin-3-ol

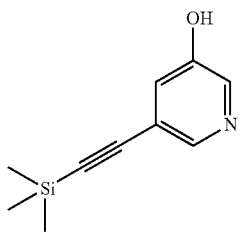

The title compound is synthesized according to general procedure GP2 starting from 2.0 g (11.6 mmol) 5-bromo-3-hydroxy-pyridine and 2.3 mL (16.2 mmol) 1-trimethylsilyl-ethyne using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using DCM/MeOH gradient. Yield: 2.0 g (91%)

A-7) 5-Trimethylsilanylethynyl-pyridin-3-ylamine

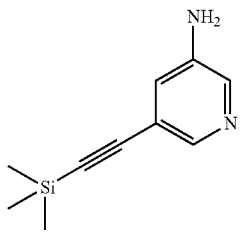

The title compound is synthesized according to general procedure GP2 starting from 2.0 g (11.6 mmol) 5-bromo-3-amino-pyridine and 2.3 mL (16.2 mmol) 1-trimethylsilyl-ethyne using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using DCM/MeOH gradient. The product precipitated on the column and is subsequently extracted from the silica gel with pure MeOH. Yield: 2.0 g (91%).

A-8) 5-Trimethylsilanylethynyl-1H-pyrazolo[3,4-b]pyridine

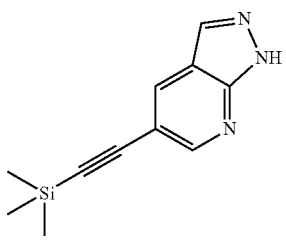

The title compound is synthesized according to general procedure GP2 starting from 1.0 g (5.1 mmol) 5-bromo-1H- pyrazolo[4,5-B]pyridine and 1.0 mL (7.1 mmol) 1-trimethylsilyl-ethyne using 29 mg (0.15 mmol) CuI, 133 mg (0.51 mmol) triphenylphosphine, 106 mg (0.15 mmol) PdCl$_2$(PPh$_3$)$_2$ and 8.4 mL (60.6 mmol) triethylamine in 8 mL dry THF. The formed precipitate is filtered off and the product is purified by RP-HPLC using ACN/H$_2$O gradient. Yield: 542 mg (50%)

A-9) 5-Trimethylsilanylethynyl-1H-pyrrolo[2,3-b]pyridine

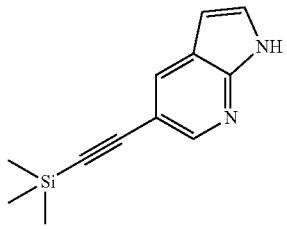

The title compound is synthesized according to general procedure GP2 starting from 3.0 g (15.2 mmol) 5-bromo-1H-pyrrolo[2,3-B]pyridine and 3.0 mL (21.3 mmol) 1-trimethylsilyl-ethyne using 87 mg (0.46 mmol) CuI, 400 mg (1.5 mmol) triphenylphosphine, 312 mg (0.46 mmol) PdCl$_2$(PPh$_3$)$_2$ and 25.4 mL (182 mmol) triethylamine in 25 mL dry THF. The formed precipitate is filtered off and the product is purified by chromatography on silica gel using a DCM/MeOH gradient. Yield: 3.05 g (94%)

A-10) 6-Trimethylsilanylethynyl-3H-imidazo[4,5-b]pyridine

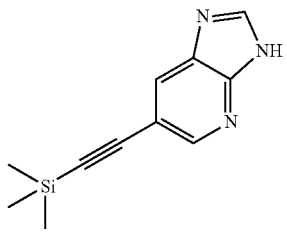

The title compound is synthesized according to general procedure GP2 starting from 1.2 g (6.1 mmol) 5-bromo-3H-imidazo[4,5-B]pyridine and 1.2 mL (8.4 mmol) 1-trimethylsilyl-ethyne using 34 mg (0.18 mmol) CuI, 159 mg (0.61 mmol) triphenylphosphine, 128 mg (0.18 mmol) PdCl$_2$(PPh$_3$)$_2$ and 10.1 mL (72.7 mmol) triethylamine in 10 mL dry THF. The formed precipitate is filtered off and the product is purified by RP-HPLC using a ACN/H$_2$O gradient. Yield: 606 mg (46%)

A-11) 5-Ethynyl-2-methyl-pyridine

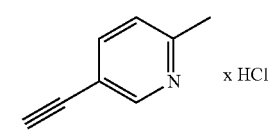

The title compound is synthesized according to general procedure GP3 starting from 2.2 g (11.6 mmol) 2-methyl-5-trimethylsilanylethynyl-pyridine (A4) and 802 mg (5.8 mmol) K$_2$CO$_3$ in 13 mL MeOH. The crude product is purified by chromatography on silica gel using a cyclohexane/ethyl acetate gradient. Since sublimation is observed at 40° C./40 mbar the product is extracted from the organic phase with 1 N HCl and isolated as the hydrochloride after lyophilization. Yield: 1.3 g (73%).

A-12) 5-Ethynyl-2-amino-pyridine

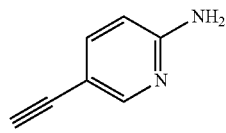

The title compound is synthesized according to general procedure GP3 starting from 5.5 g (28.9 mmol) 5-trimethylsilanylethynyl-pyridin-2-ylamine (A5) and 2.0 mg (14.4 mmol) K$_2$CO$_3$ in 30 mL MeOH. Yield: 2.89 mg (85%) after chromatography on silica gel.

A-13 (5-Ethynyl-pyridin-2-yl)-methyl-amine

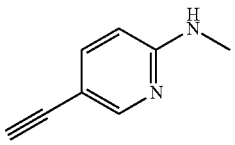

The title compound is synthesized according to general procedure GP3 starting from 1.5 g (7.3 mmol) methyl-(5-trimethylsilanylethynyl-pyridin-2-yl)-amine (A6) and 507 mg (3.7 mmol) K$_2$CO$_3$ in 10 mL MeOH. Yield: 698 mg (56%) after chromatography on silica gel.

A-14) (5-Ethynyl-pyridin-2-yl)-ethyl-amine

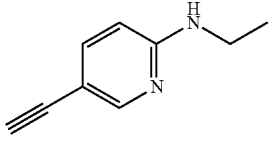

The title compound is synthesized according to general procedure GP3 starting from 980 mg (4.5 mmol) TMS-alkyne and 310 mg (2.3 mmol) K$_2$CO$_3$ in 6 mL MeOH.

Yield: 388 mg (59%) after chromatography on silica gel.

A-15) 5-Ethynyl-pyridin-3-ol

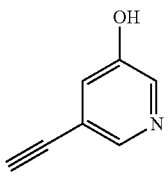

The title compound is synthesized according to general procedure GP3 starting from 2.0 g (10.5 mmol) TMS-alkyne and 722 mg (5.2 mmol) K$_2$CO$_3$ in 10 mL MeOH. Yield: 804 mg (49%) after chromatography on silica gel.

A-16) 5-Ethynyl-pyridin-3-ylamine

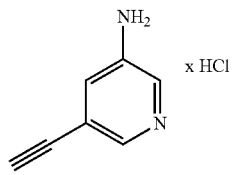

The title compound is synthesized according to general procedure GP3 starting from 2.0 g (10.5 mmol) TMS-alkyne and 722 mg (5.2 mmol) K$_2$CO$_3$ in 10 mL MeOH. Yield: 1.2 g (74%) after chromatography on silica gel and precipitation from dioxane/HCl.

A-17) 5-Ethynyl-1H-pyrazolo[3,4-b]pyridine

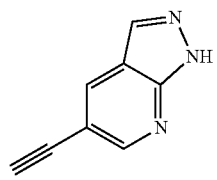

The title compound is synthesized according to general procedure GP3 starting from 542 mg (2.5 mmol) TMS-alkyne and 174 mg (1.3 mmol) K$_2$CO$_3$ in 6 mL MeOH.
Yield: 330 mg (92%) after extraction.

A-18) 5-Ethynyl-1H-pyrrolo[2,3-b]pyridine

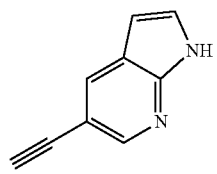

The title compound is synthesized according to general procedure GP3 starting from 3.05 g (14.2 mmol) TMS-alkyne and 983 mg (7.1 mmol) K$_2$CO$_3$ in 15 mL MeOH. Yield: 1.23 g (61%) after chromatography on silica gel.

A-19) 6-Ethynyl-3H-imidazo[4,5-b]pyridine

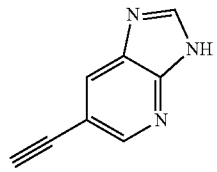

The title compound is synthesized according to general procedure GP3 starting from 706 mg (3.3 mmol) TMS-alkyne and 227 mg (1.6 mmol) K$_2$CO$_3$ in 6 mL MeOH. Yield: 491 mg (94%) after extraction.

A-20) 3-Iodo-2-methyl-pyridin-4-ol

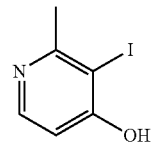

To a solution of 10 g (91.6 mmol) 2-methyl-pyridin-4-ol in 100 mL water 20.6 g (91.6 mmol) NIS are added in one portion. The reaction mixture is stirred at RT until reaction control by LC-MS indicated complete conversion of the starting material. The precipitate is filtered off, washed with washed an dried. The isolated solid comprises a mixture of the desired product and bis-iodated starting material (presumably 4-hydroxy-3,5-diiodo-2-methyl-pyridine) and is used for the next step without further purification.
Yield: 17.6 g.

A-21) 4-Chloro-3-iodo-2-methyl-pyridine

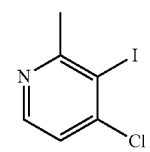

Under an inert atmosphere the crude product obtained from the iodination is taken up in 300 mL acteonitrile. A solution of 82 g (898 mmol) POCl$_3$ in 50 mL acetonitrile as well as catalytic amounts of P$_2$O$_5$ are added before the reaction mixture is heated under reflux for 2 h. LC-MS indicated complete conversion of the starting material. After cooling to RT the mixture is concentrated under vacuum to a volume of about 50 mL. The formed precipitate is filtered off and discarded. The pH of the solution is adjusted to pH about 1 by addition of KOH (s). Again, the precipitate is filtered off and discarded. Additional KOH is added until pH about 7. The product precipitated from the reaction mixture, is filtered off, washed with water and dried under vacuum at 40° C. Yield: 8.1 g (43% over 2 steps).

A-22) 2-Ethyl-pyridine-1-oxide

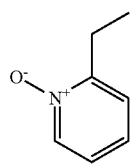

To the solution 500 g (4.7 mol) 2-ethylpyridine in 2.0 L acetic acid is added H$_2$O$_2$ (1586.0 g, 13.900 mol). Then the mixture is heated to 80° C. overnight. After cooling to room RT, the mixture is poured into the crushed ice, and extracted with DCM (8×1.0 L). The DCM layers are combined, washed with saturated Na$_2$SO$_3$ solution, dried over anhydrous Na$_2$SO$_4$. The solvent is removed in vaccuo to afford the title compound.
Yield: 573.8 g (100%).

A-23) 2-Ethyl-4-nitro-pyridine-1-oxide

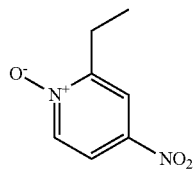

Concentrated H₂SO₄ (1826.0 g, 18.660 mol) and fuming HNO₃ (1174.0 g, 18.640 mol) are mixed at 0° C. Then 573.8 g (4.7 mol) 2-ethyl-pyridine-1-oxide are added to the mixture over 1 h. The resulting mixture is heated to 80° C. for 3 h. After cooling to RT, the mixture is slowly poured into the crushed ice with fierce stirring. The aqueous layer is extracted with DCM (6×1.0 L), the combined layer is dried over anhydrous Na₂SO₄. The solvent is removed in vaccuo to afford the title compound. Yield: 700.0 g (89%).

A-24) 2-Ethyl-pyridin-4-ylamine

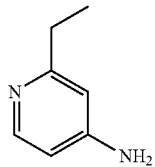

A solution of 388.0 g (2.3 mol) 2-ethyl-4-nitro-pyridine-1-oxide in 3.0 L EtOH and 1.0 L saturated NH₄Cl solution (1.0 L) is stirred with 647.5 g (11.6 mol) iron powder. This mixture is refluxed for 3 h. The iron powder is filtered off with Celite®, and the solvent is removed from the filtrate in vaccuo to afford a crude oil. This oil is diluted with DCM/MeOH (1.0 L, 10:1) and the undissolved NH₄Cl is removed by filtration, the filtrate is dried in vaccuo to afford the title compound. Yield: 200.0 g (71%).

A-25) 2-Ethyl-pyridin-4-ol

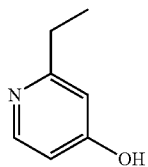

282.1 g (2.3 mol) 2-Ethyl-pyridin-4-ylamine are dissolved in concentrated HNO₃ (789 mL, 11.561 mol) and H₂O (1.5 L). Then a solution of NaNO₂ (238.9 g, 3.468 mol) in H₂O (600 mL) is slowly added to the solution over 2 h at 0° C. After the addition, the mixture is warmed to RT and stirred for additional 2 h. The reaction mixture is stored at −2° C. overnight. The precipitate is collected by filtration, and dried in vaccuo to afford the title compound. Yield: 155.1 g, (54%)

A-26) 2-Ethyl-3-iodo-pyridin-4-ol

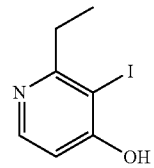

To a solution of 72.0 g (0.58 mol) 2-ethyl-pyridin-4-ol in 1.0 L H₂O 130.0 g (0.58 mol) NIS are added in ten portions over 1 h. The mixture is stirred at RT overnight. The acetic acid (1.5 L) is added in one portion. The formed precipitate is removed by filtration. The filtrate is purified on silica gel chromatography (DCM:MeOH about 30:1) to afford the title compound. Yield: 9.0 g (6%).

A-27) 4-Chloro-2-ethyl-3-iodo-pyridine

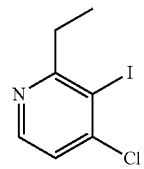

A solution of 165.1 g (1.08 mol) POCl₃ in 100 mL CH₃CN is added dropwise to a solution of 27.1 g (108 mmol) 2-ethyl-3-iodo-pyridin-4-ol in 150 mL CH₃CN at RT. Then Et₃N (21.9 g, 216 mmol) is added slowly over 20 min before the reaction mixture is heated to 60° C. for 3 h. The reaction mixture is evaporated in vaccuo to afford an oil. This crude oil is poured into the crushed ice, and the aqueous phase is extracted with petroleum ether/EtOAc (3×, 200 mL; 10:1). The organic phase is collected, dried over anhydrous Na₂SO₄. The solvent is removed in vacuo to afford desired product. Yield: 22.0 g (76%).

A-28) 5-(4-Chloro-2-methyl-pyridin-3-ylethynyl)-pyridin-2-ylamine

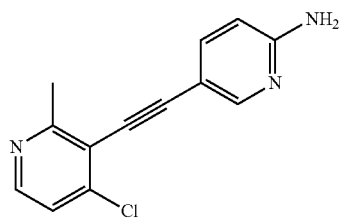 [SMILES: Cc1nccc(Cl)c1C#Cc1ccc(N)nc1]

The title compound is synthesized according to general procedure GP1 starting from 1.0 g (4.0 mmol) 4-chloro-3-iodo-2-methyl-pyridine and 513 mg (4.3 mmol) 2-amino-5-ethynyl-pyridine using 75 mg (0.40 mmol) CuI, 276 mg (0.40 mmol) PdCl₂(PPh₃)₂ and 5.4 mL (39.5 mmol) triethylamine in 40 mL dry DMF. After completion of the reaction the solvent is removed under vacuum and the product is purified by chromatography on silica gel using a DCM/MeOH gradient (100:0 to 90:10). Yield: 617 mg (64%).

A-29) [5-(4-Chloro-2-methyl-pyridin-3-ylethynyl)-pyridin-2-yl]-methyl-amine

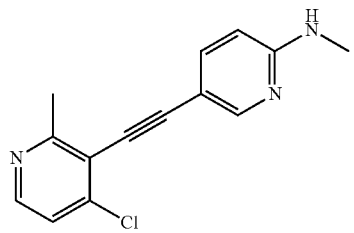 [SMILES: CNc1ccc(C#Cc2c(Cl)ccnc2C)cn1]

The title compound is synthesized according to general procedure GP1 starting from 20 mg (0.08 mmol) 4-chloro-3-iodo-2-methyl-pyridine and 11 mg (0.09 mmol) (5-Ethynyl-pyridin-2-yl)-methyl-amine using 1.5 mg (0.01 mmol) CuI, 5.5 mg (0.01 mmol) $PdCl_2(PPh_3)_2$ and 0.11 mL (0.8 mmol) triethylamine in 1 mL dry DMF. After completion of the reaction the product is purified by RP-HPLC using a ACN/$H_2O$ gradient (95:5 to 70:30). Yield: 20 mg (98%).

A-30) 5-(4-Chloro-2-ethyl-pyridin-3-ylethynyl)-pyridin-2-ylamine

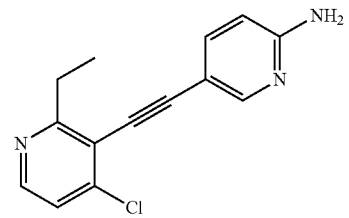 [SMILES: CCc1nccc(Cl)c1C#Cc1ccc(N)nc1]

The title compound is synthesized according to general procedure GP1 starting from 1.0 g (3.7 mmol) 4-chloro-3-iodo-2-ethyl-pyridine and 485 mg (4.1 mmol) 2-amino-5-ethynyl-pyridine using 36 mg (0.40 mmol) CuI, 131 mg (0.40 mmol) $PdCl_2(PPh_3)_2$ and 5.2 mL (39.5 mmol) triethylamine in 25 mL dry DMF. After completion of the reaction the reaction mixture is added dropwise into water. The precipitate is filtered off and taken up with iPrOH. The product remains is solution while the side-product (alkyne dimer from Glaser-homo-coupling) forms a precipitate and is filtered off. The mother liquid is concentrated under vacuum. Yield: 718 mg (75%).

A-31) 4-[3-(6-Amino-pyridin-3-ylethynyl)-2-methyl-pyridin-4-yl]-2-fluoro-benzoic acid methyl ester

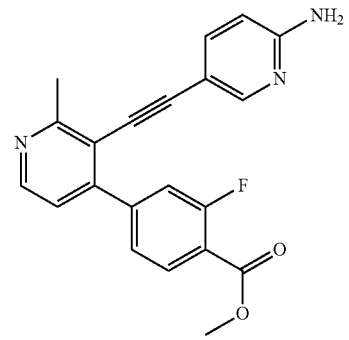 [SMILES: COC(=O)c1ccc(-c2ccnc(C)c2C#Cc2ccc(N)nc2)cc1F]

The title compound is synthesized according to general procedure GP3 starting from 500 mg (2.1 mmol) 5-(4-chloro-2-methyl-pyridin-3-ylethynyl)-pyridin-2-ylamine using 812 mg (4.1 mmol) 3-fluoro-4-methoxycarbonylphenyl boronic acid, 188 mg (0.21 mmol) $Pd_2(dba)_3$, 293 mg (0.62 mmol) X-Phos and 567 mg (2.5 mmol) $K_3PO_4$ in 4 mL dioxane. The reaction mixture is stirred for 180 min at 150° C. under microwave irradiation. The product is purified by chromatography on silica gel using an DCM/MeOH-gradient (99:1 to 90:10, 20 min). Yield: 52 mg (70%).

A-32) 4-[3-(6-Amino-pyridin-3-ylethynyl)-2-methyl-pyridin-4-yl]-2-fluoro-benzoic acid

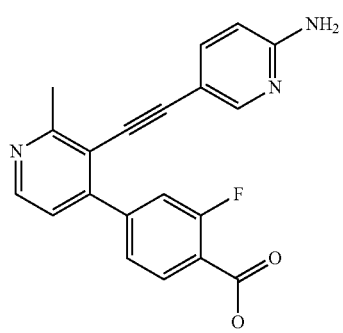 [SMILES: Cc1nccc(-c2ccc(C(=O)O)c(F)c2)c1C#Cc1ccc(N)nc1]

The title compound is synthesized according to general procedure GP4 starting from 300 mg (0.83 mmol) 4-[3-(6-amino-pyridin-3-ylethynyl)-2-methyl-pyridin-4-yl]-2-fluoro-benzoic acid methyl ester using 0.83 mL (0.83 mmoL) 1 N NaOH in 5 mL THF. The precipitate is collected by filtration and washed with THF. Yield: 280 mg (97%).

A-33) 4-[3-(6-Amino-pyridin-3-ylethynyl)-2-methyl-pyridin-4-yl]-benzoic acid methyl ester

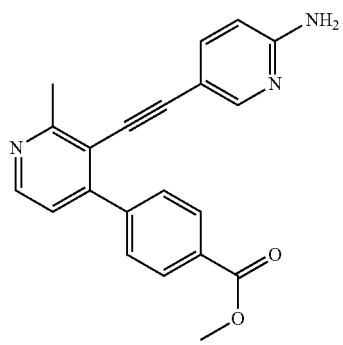 [SMILES: COC(=O)c1ccc(-c2ccnc(C)c2C#Cc2ccc(N)nc2)cc1]

The title compound is synthesized according to general procedure GP3 starting from 1.5 g (6.2 mmol) 5-(4-chloro-2-methyl-pyridin-3-ylethynyl)-pyridin-2-ylamine using 2.2 g (12.3 mmol) 4-methoxycarbonylphenyl boronic acid, 281 mg (0.31 mmol) $Pd_2(dba)_3$, 440 mg (0.92 mmol) X-Phos and 1.7 g (7.4 mmol) $K_3PO_4$ in 25 mL dioxane. The reaction mixture is stirred over night at 100° C. After cooling to RT the reaction mixture is added dropwise into water, the precipitate is filtered off. The solid is taken up in iPrOH, stirred for a few minutes, filtered off and dried under vacuum. Yield: 2.0 g (95%, residual Pd).

A-34) 4-[3-(6-Amino-pyridin-3-ylethynyl)-2-methyl-pyridin-4-yl]-benzoic acid

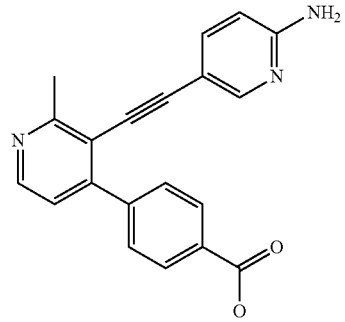 [SMILES: Cc1nccc(-c2ccc(C(=O)O)cc2)c1C#Cc1ccc(N)nc1]

The title compound is synthesized according to general procedure GP4 starting from 2.0 g (5.8 mmol) 4-[3-(6-amino-pyridin-3-ylethynyl)-2-methyl-pyridin-4-yl]-benzoic acid methyl ester using 11.6 mL (11.6 mmoL) 1 N NaOH in 8 mL THF. After completion of the reaction the pH is adjusted to pH about 5 with 1.0 N HCl. The precipitate is collected by filtration, washed with water and dried under vacuum. The solid is taken up in iPrOH, stirred for a few minutes before the solid is isolated by filtration and dried at 40° C. under vacuum. Yield: 1.9 g (99%).

A-35) 4-[3-(6-Amino-pyridin-3-ylethynyl)-2-methyl-pyridin-4-yl]-2-chloro-benzoic acid methyl ester

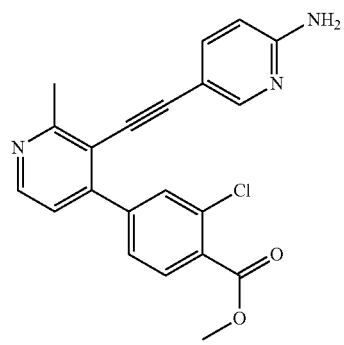 [SMILES: COC(=O)c1ccc(-c2ccnc(C)c2C#Cc2ccc(N)nc2)cc1Cl]

The title compound is synthesized according to general procedure GP3 starting from 300 mg (1.2 mmol) 5-(4-chloro-2-methyl-pyridin-3-ylethynyl)-pyridin-2-ylamine using 527 mg (2.4 mmol) 3-chloro-4-methoxycarbonylphenyl boronic acid, 112 mg (0.12 mmol) Pd$_2$(dba)$_3$, 176 mg (0.37 mmol) X-Phos and 340 mg (1.5 mmol) K$_3$PO$_4$ in 4 mL dioxane. The reaction mixture is stirred for 60 min at 140° C. under microwave irradiation. The solvent is removed under reduced pressure before DMF is added and the formed precipitate is filtered off. The product is isolated from the mother liquid by RP-HPLC chromatography using an ACN/H$_2$O-gradient. Yield: 300 mg (65%).

A-36) 4-[3-(6-Amino-pyridin-3-ylethynyl)-2-methyl-pyridin-4-yl]-2-chloro-benzoic acid

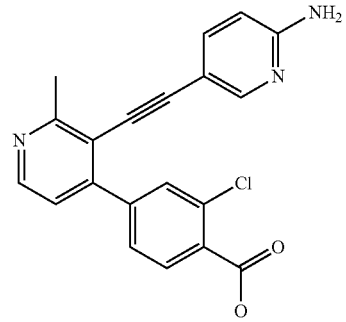 [SMILES: Cc1nccc(-c2ccc(C(=O)O)c(Cl)c2)c1C#Cc1ccc(N)nc1]

The title compound is synthesized according to general procedure GP4 starting from 460 mg (1.2 mmol) 4-[3-(6-amino-pyridin-3-ylethynyl)-2-methyl-pyridin-4-yl]-2-chloro-benzoic acid methyl ester using 2.4 mL (2.4 mmoL) 1 N NaOH in 10 mL THF. The product is purified by chromatography on silica gel using an DCM/MeOH-gradient (100:0 to 90:10, NH$_3$). Yield: 420 mg (95%).

A-37) 4-[3-(6-Amino-pyridin-3-ylethynyl)-2-ethyl-pyridin-4-yl]-2-fluoro-benzoic acid methyl ester

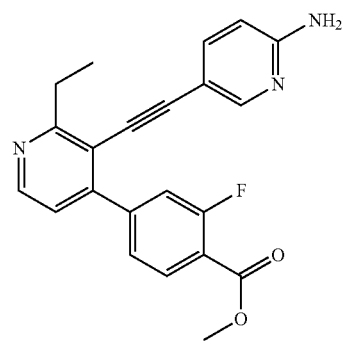 [SMILES: CCc1nccc(-c2ccc(C(=O)OC)c(F)c2)c1C#Cc1ccc(N)nc1]

The title compound is synthesized according to general procedure GP3 starting from 3.2 g (12.3 mmol) 5-(4-Chloro-2-ethyl-pyridin-3-ylethynyl)-pyridin-2-ylamine (A-30) using 3.6 g (18.4 mmol) 3-Fluoro-4-methoxycarbonylphenyl boronic acid, 561 mg (0.61 mmol) Pd$_2$(dba)$_3$, 877 mg (1.84 mmol) X-Phos, 519 mg (12.3 mmol) LiCl and 3.39 g (14.7 mmol) K$_3$PO$_4$ in a mixture of 60 mL 1,2-dimethoxyethane and 10 mL water. The reaction mixture is stirred for 16 h at 95° C. After completion of the reaction, the mixture is poured into water and the formed precipitate is collected by filtration. The product is purified by chromatography on silica gel using an DCM/MeOH-mixture (3% MeOH, flow 55 mL/min). Yield: 2.46 g (53%).

A-38) 4-[3-(6-Amino-pyridin-3-ylethynyl)-2-ethyl-pyridin-4-yl]-2-fluoro-benzoic acid

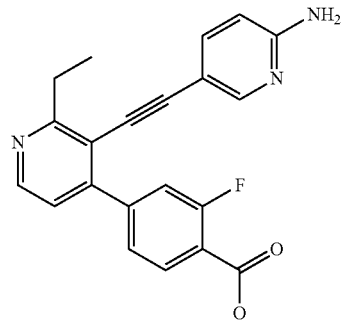 [SMILES: CCc1nccc(-c2ccc(C(=O)O)c(F)c2)c1C#Cc1ccc(N)nc1]

The title compound is synthesized according to general procedure GP4 starting from 2.36 g (6.3 mmol) 4-[3-(6-Amino-pyridin-3-ylethynyl)-2-ethyl-pyridin-4-yl]-2-fluoro-benzoic acid methyl ester (A-37) using 9.4 mL (9.4 mmoL) 1N NaOH in 40 mL THF. The reaction mixture is stirred for 2 h at 95° C. The solvent is removed under reduced pressure, the crude product is taken up with water and the pH is adjusted to 5 (with 1N HCl). The precipitate is collected by filtration. Yield after drying: 2.2 g (97%).

A-39) 4-[3-(6-Amino-pyridin-3-ylethynyl)-2-ethyl-pyridin-4-yl]-2-chloro-benzoic acid methyl ester

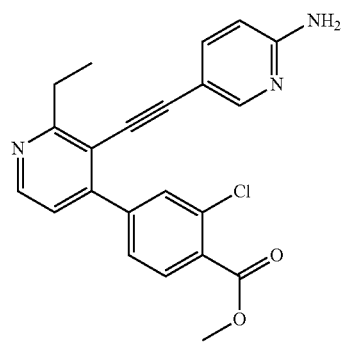 [SMILES: CCc1nccc(-c2ccc(C(=O)OC)c(Cl)c2)c1C#Cc1ccc(N)nc1]

The title compound is synthesized according to general procedure GP3 starting from 2.0 g (7.8 mmol) 5-(4-Chloro-2-ethyl-pyridin-3-ylethynyl)-pyridin-2-ylamine (A-30) using 2.5 g (11.6 mmol) 3-chloro-4-methoxycarbonylphenyl boronic acid, 335 mg (0.39 mmol) $Pd_2(dba)_3$, 555 mg (1.2 mmol) X-Phos and 2.7 g (11.6 mmol) $K_3PO_4$ in a mixture of 100 mL DME and 20 mL water. The reaction mixture is stiffed under reflux for 4 days. The DME is removed under reduced pressure and the aqueous is extracted with ethyl acetate. The organic phase is dried over $Na_2SO_4$, filtered and the solvent removed under vacuum. The product is purified by chromatography on silica gel using an DCM/MeOH-gradient. Yield: 0.59 g (19%).

A-40) 4-[3-(6-Amino-pyridin-3-ylethynyl)-2-ethyl-pyridin-4-yl]-2-chloro-benzoic acid

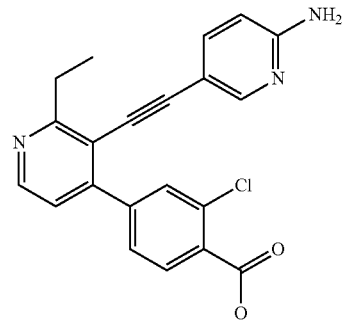 [SMILES: CCc1nccc(-c2ccc(C(=O)O)c(Cl)c2)c1C#Cc1ccc(N)nc1]

The title compound is synthesized according to general procedure GP4 starting from 1.1 g (2.8 mmol) 4-[3-(6-Amino-pyridin-3-ylethynyl)-2-ethyl-pyridin-4-yl]-2-chloro-benzoic acid methyl ester (A-39) using 134 mg (5.6 mmoL) LiOH in a mixture of 100 mL THF and 20 mL water. After completion of the reaction, THF is removed under reduced pressure, the aqueous solution is acidified with 1N HCl to pH ~1 before the pH is adjusted to 6 with saturated aqueous $NaHCO_3$ solution. The precipitated product is collected by filtration, washed with water and methanol. Yield: 760 mg (72%).

A-41) 4-[3-(6-Amino-pyridin-3-ylethynyl)-2-ethyl-pyridin-4-yl]-2-methoxy-benzoic acid methyl ester

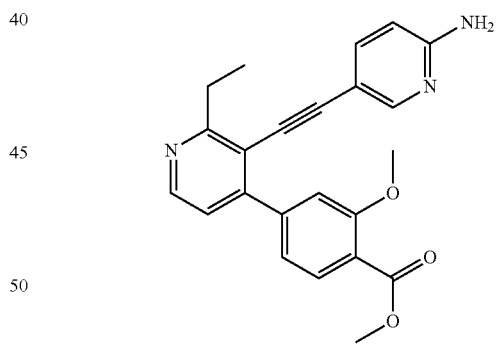

The title compound is synthesized according to general procedure GP3 starting from 1.5 g (5.0 mmol) 5-(4-Chloro-2-ethyl-pyridin-3-ylethynyl)-pyridin-2-ylamine (A-30) using 1.6 g (7.4 mmol) 3-methoxy-4-methoxycarbonylphenyl boronic acid, 135 mg (0.15 mmol) $Pd_2(dba)_3$, 354 mg (0.74 mmol) X-Phos and 2.2 g (9.4 mmol) $K_3PO_4$ in 20 mL dioxane. The reaction mixture is stirred under reflux over night. The solvent is removed under reduced pressure before water is added and the formed precipitate is collected by filtration. The product is purified by chromatography on silica gel using a DCM/MeOH-gradient. Yield: 1.07 g (56%).

A-42) 4-[3-(6-Amino-pyridin-3-ylethynyl)-2-ethyl-pyridin-4-yl]-2-methoxy-benzoic acid

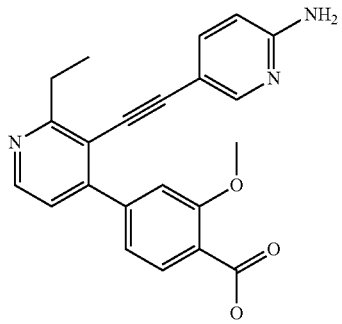 [SMILES: CCc1nccc(-c2ccc(C(=O)O)c(OC)c2)c1C#Cc1ccc(N)nc1]

The title compound is synthesized according to general procedure GP4 starting from 1.07 g (2.77 mmol) 4-[3-(6-Amino-pyridin-3-ylethynyl)-2-ethyl-pyridin-4-yl]-2-methoxy-benzoic acid methyl ester (A-41) using 2.4 mL (2.4 mmoL) 1N NaOH in 30 mL THF. The reaction mixture is stirred over night, after complete consumption of the starting material the pH is adjusted to 4 (using 1N HCl). As no precipitate is formed, the aqueous phase is extracted with DCM. However, the product precipitates upon addition of DCM and is collected by filtration. Additional product is precipitated from the mother liquid by adjustment of the pH to 6 (using 1N NaOH). Yield of the combined fractions: 990 mg (96%).

A-43) 4-[3-(6-Amino-2-ethyl-pyridin-3-ylethynyl)-2-ethyl-pyridin-4-yl]-2-fluoro-benzoic acid methyl ester

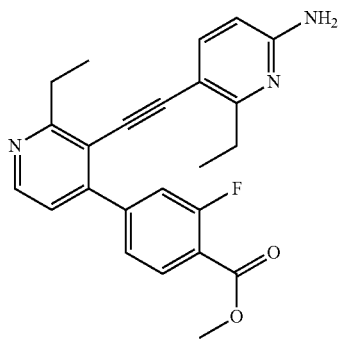 [SMILES: CCc1nc(N)ccc1C#Cc1c(-c2ccc(C(=O)OC)c(F)c2)ccnc1CC]

The title compound is synthesized according to general procedure GP3 starting from 1.29 g (4.5 mmol) 5-(4-Chloro-2-ethyl-pyridin-3-ylethynyl)-6-ethyl-pyridin-2-ylamine (A-30) using 1.34 mg (6.8 mmol) 3-Fluoro-4-methoxycarbonylphenyl boronic acid, 1.4 g (0.9 mmol) Pd(PPh$_3$)$_4$ and 1.19 g (8.6 mmol) K$_2$CO$_3$ in a mixture of 9 mL 1,2-dimethoxyethane and 2.25 mL water. The reaction mixture is stirred twice for 30 min at 130° C. under microwave irradiation. The product is precipitated by the addition of water, filtered off and purified by chromatography on silica gel using a cyclohexane/ethyl acetate gradient. Yield: 944 mg (52%).

A-44) 4-[3-(6-Amino-2-ethyl-pyridin-3-ylethynyl)-2-ethyl-pyridin-4-yl]-2-fluoro-benzoic acid

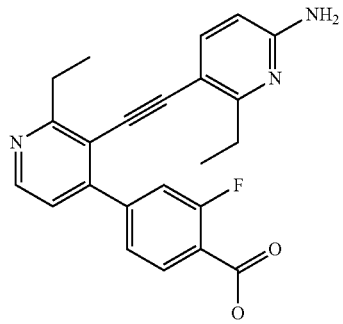 [SMILES: CCc1nc(N)ccc1C#Cc1c(-c2ccc(C(=O)O)c(F)c2)ccnc1CC]

The title compound is synthesized according to general procedure GP4 starting from 944 mg (2.34 mmol) 4-[3-(6-Amino-2-ethyl-pyridin-3-ylethynyl)-2-ethyl-pyridin-4-yl]-2-fluoro-benzoic acid methyl ester (A-43) using 3.5 mL (3.5 mmoL) 1N NaOH in 25 mL THF. The reaction mixture is diluted with water and the product extracted with DCM. The organic phase is separated and the solvent removed under reduced pressure. The crude product is used without further purification. Yield: 945 mg (>100%).

A-45) 4-[2-Ethyl-3-(6-methylamino-pyridin-3-ylethynyl)-pyridin-4-yl]-2-fluoro-benzoic acid methyl ester

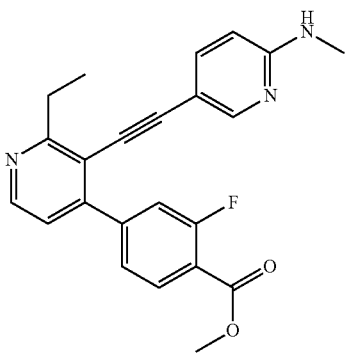 [SMILES: CCc1nccc(-c2ccc(C(=O)OC)c(F)c2)c1C#Cc1ccc(NC)nc1]

The title compound is synthesized according to general procedure GP3 starting from 770 mg (2.8 mmol) 5-(4-Chloro-2-ethyl-pyridin-3-ylethynyl)-pyridin-2-yl]-methylamine (A-30) using 841 mg (4.3 mmol) 3-Fluoro-4-methoxycarbonylphenyl boronic acid, 882 mg (0.57 mmol) Pd(PPh$_3$)$_4$ and 752 mg (5.4 mmol) K$_2$CO$_3$ in a mixture of 7.5 mL 1,2-dimethoxyethane and 1.5 mL water. The reaction mixture is stirred for 30 min at 180° C. under microwave irradiation. The reaction mixture is filtered off and the product is precipitated from the solution by addition of water. After filtration, the product is purified by chromatography on silica gel using an DCM/MeOH-gradient. Yield: 850 mg (77%).

A-46) 4-[2-Ethyl-3-(6-methylamino-pyridin-3-yl-ethynyl)-pyridin-4-yl]-2-fluoro-benzoic acid

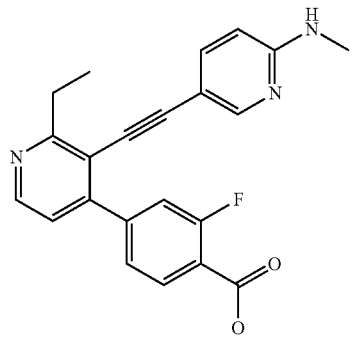 [SMILES: CCc1nccc(-c2ccc(C(=O)O)c(F)c2)c1C#Cc1ccc(NC)nc1]

The title compound is synthesized according to general procedure GP4 starting from 850 mg (2.18 mmol) 4-[3-(6-Amino-pyridin-3-ylethynyl)-2-ethyl-pyridin-4-yl]-2-fluoro-benzoic acid methyl ester (A-45) using 3.3 mL (3.3 mmoL) 1N NaOH in 22 mL THF. The reaction mixture is stirred for 72 h at 65° C. The product is precipitated by addition of water and is collected by filtration. Yield after drying: 747 mg (91%).

Examples 1-130

The example compounds are synthesized according to the general procedures GP3 (Suzuki coupling) or GP5-9 (formation of amides or ureas) as outlined above. The appropriate starting materials required for synthesis can be deduced from the table of the examples. All building blocks and reagents are either commercially available or can be synthesized by methods well known in literature.

TABLE 1

| | Examples | | | | |
|---|---|---|---|---|---|
| No. | Structures | Starting material | MW | [M + H]$^+$ | $t_{Ret}$ |
| 1 | | A-36 | 472.0 | M + H = 472/474<br>M − H = 470/472 | tR = 1.75<br>(1.90) |
| 2 | | A-32 | 455.5 | M + H = 456 | tR = 1.73 |

TABLE 1-continued

Examples

| No. | Structures | Starting material | MW | [M + H]+ | $t_{Ret}$ |
|---|---|---|---|---|---|
| 3 | 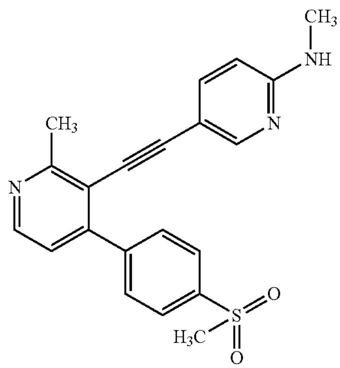 [SMILES: CNc1ccc(C#Cc2c(-c3ccc(S(C)(=O)=O)cc3)ccnc2C)cn1] | A-29 | 377.5 | M + H = 378 (258) | tR = 1.58 (1.65) |
| 4 | 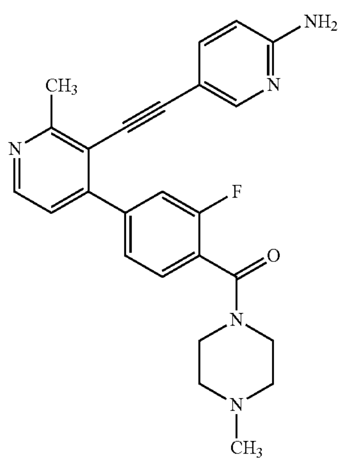 | A-32 | 429.5 | M + H = 429 | tR = 1.51 |
| 5 | 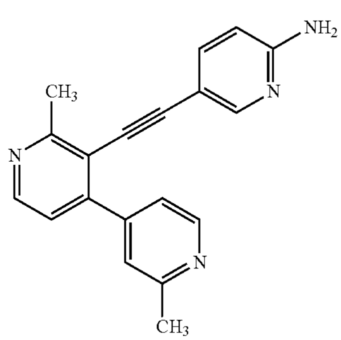 [SMILES: Cc1cc(-c2ccnc(C)c2C#Cc2ccc(N)nc2)ccn1] | A-28 | 300.4 | M + H = 301 | tR = 1.43 |

TABLE 1-continued
Examples
| No. | Structures | Starting material | MW | [M + H]⁺ | $t_{Ret}$ |
|---|---|---|---|---|---|
| 6 | 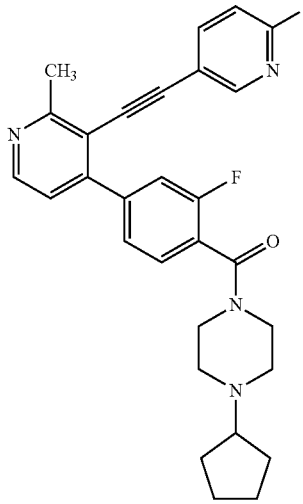 | A-32 | 483.6 | M + H = 484 | tR = 1.80 |
| 7 | 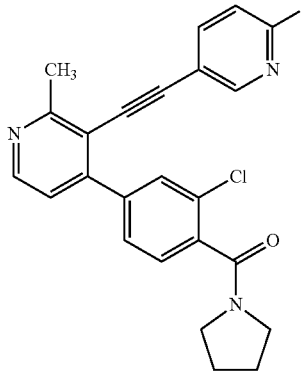 | A-36 | 416.9 | M + H = 417/419 | tR = 1.65 |
| 8 | 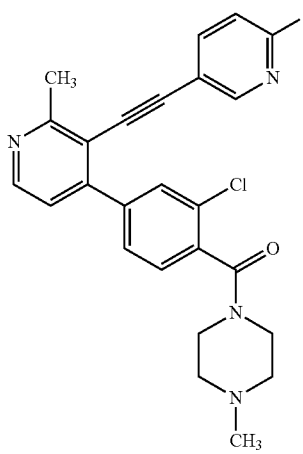 | A-36 | 446.0 | M + H = 446 | tR = 1.54 |

TABLE 1-continued
| No. | Structures | Starting material | MW | [M + H]⁺ | $t_{Ret}$ |
|---|---|---|---|---|---|
| 9 | 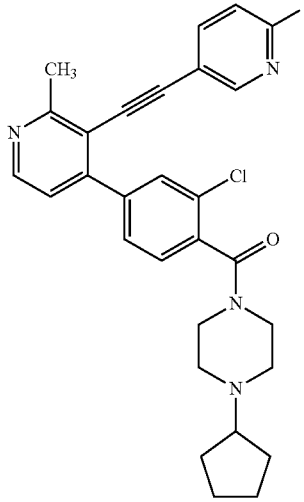 | A-36 | 500.0 | M + H = 500 | tR = 1.85 |
| 10 | 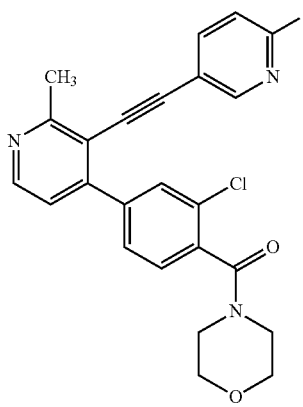 | A-36 | 432.9 | M + H = 433 | tR = 1.54 |
| 11 | 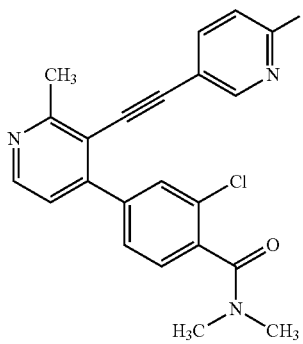 | A-36 | 390.9 | M + H = 391/393 | tR = 1.56 |

TABLE 1-continued
| | | Examples | | | |
|---|---|---|---|---|---|
| No. | Structures | Starting material | MW | [M + H]+ | $t_{Ret}$ |
| 12 | 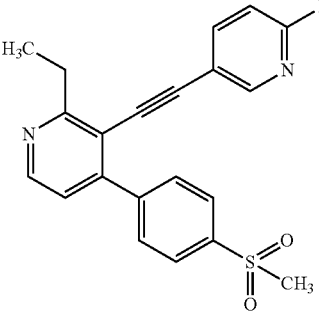 | A-30 | 377.5 | M + H = 378 | tR = 1.54 |
| 13 | 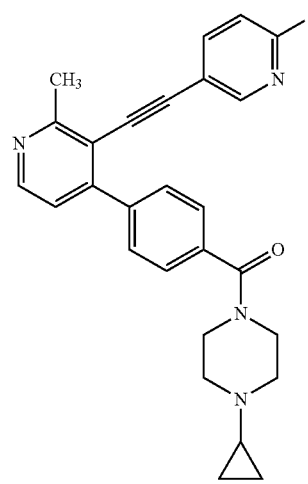 | A-34 | 437.5 | M + H = 438 | tR = 1.62 |
| 14 | 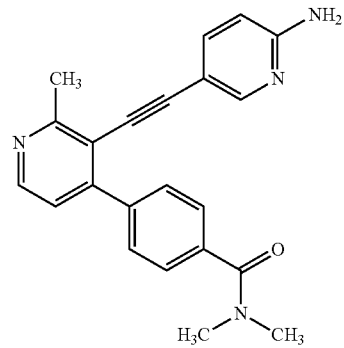 [SMILES: Cc1nccc(-c2ccc(C(=O)N(C)C)cc2)c1C#Cc1ccc(N)nc1] | A-34 | 356.4 | M + H = 357 | tR = 1.43 |

TABLE 1-continued

| No. | Structures | Starting material | MW | [M + H]⁺ | $t_{Ret}$ |
|---|---|---|---|---|---|
| 15 | 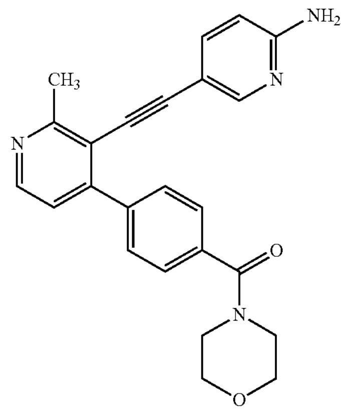 [SMILES: Cc1nccc(-c2ccc(C(=O)N3CCOCC3)cc2)c1C#Cc1ccc(N)nc1] | A-34 | 398.5 | M + H = 399 | tR = 1.42 |
| 16 | 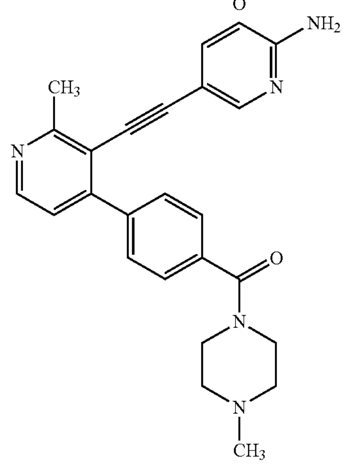 | A-34 | 411.5 | M + H = 412 | tR = 1.43 |
| 17 | 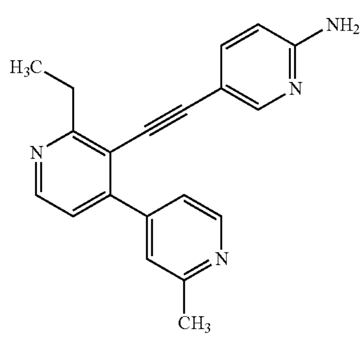 [SMILES: CCc1nccc(-c2ccnc(C)c2)c1C#Cc1ccc(N)nc1] | A-30 | 314.4 | M + H = 315 | tR = 1.51 |
| 18 | 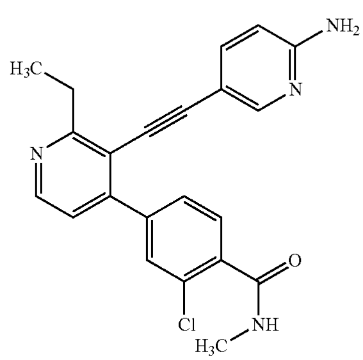 [SMILES: CCc1nccc(-c2ccc(C(=O)NC)c(Cl)c2)c1C#Cc1ccc(N)nc1] | A-30 | 390.9 | M + H = 391 | tR = 1.52 |

Example 19

2-{4-[3-(6-Amino-pyridin-3-ylethynyl)-2-ethyl-pyridin-4-yl]-phenyl}-2-methyl-propionitrile

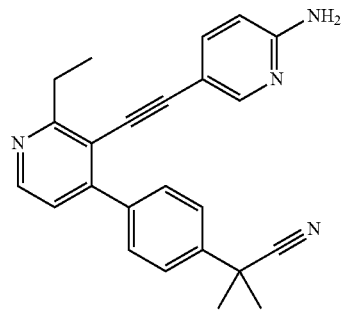 [SMILES: CCc1nccc(-c2ccc(C(C)(C)C#N)cc2)c1C#Cc1ccc(N)nc1]

The title compound is synthesized according to general procedure GP3 starting from 100 mg (0.39 mmol) 5-(4-Chloro-2-ethyl-pyridin-3-ylethynyl)-pyridin-2-ylamine (A-30) using 110 mg (0.58 mmoL) 4-2(2-cyanopropan-2-yl) benzeneboronic acid 22 mg (0.02 mmol) Pd(PPh$_3$)$_4$ and 103 mg (0.74 mmol) K$_2$CO$_3$ in a mixture of 1.0 mL DME and 0.2 mL water. The reaction mixture is stirred twice under microwave irradiation at 130° C. for 30 min. After completion of the reaction, water is added and the precipitate is collected by filtration. The crude product is purified by chromatography on silica gel using a DCM/MeOH-gradient. Since the product was not obtained in sufficient purity, it was re-purified by RP-HPLC using a H$_2$O/ACN-gradient. Yield: 30 mg (21%).

MW=366.5; [M+H]$^+$=367; $t_{Ret}$=1.83 min

Example 20

5-(2,2'-Diethyl-[4,4']bipyridinyl-3-ylethynyl)-pyridin-2-ylamine

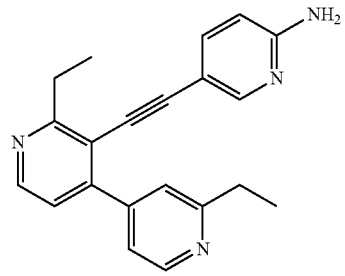 [SMILES: CCc1cc(-c2ccnc(CC)c2C#Cc2ccc(N)nc2)ccn1]

The title compound is synthesized according to general procedure GP3 starting from 100 mg (0.39 mmol) 5-(4-Chloro-2-ethyl-pyridin-3-ylethynyl)-pyridin-2-ylamine (A-30) using 146 mg (~60% purity, 0.58 mmoL) 2-ethyl-pyrid-4-yl boronic acid, 18 mg (0.02 mmol) Pd$_2$(dba)$_3$, 28 mg (0.06 mmol) XPhos and 107 mg (0.47 mmol) K$_3$PO$_4$ in a mixture of 6.0 mL DME. The reaction mixture is stirred twice under microwave irradiation at 190° C. for 300 min. The reaction mixture is concentrated in vaccuo and the crude product is purified by chromatography on silica gel using a DCM/MeOH-gradient. Yield: 9 mg (7%).

MW=328.4; [M+H]$^+$=329; $t_{Ret}$=1.61 min

Example 21

5-(2-Ethyl-2',6'-dimethyl-[4,4]bipyridinyl-3-ylethynyl)-pyridin-2-ylamine

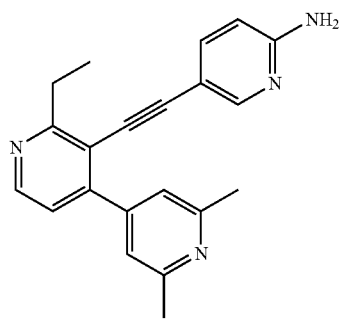 [SMILES: CCc1nccc(-c2cc(C)nc(C)c2)c1C#Cc1ccc(N)nc1]

The title compound is synthesized according to general procedure GP3 starting from 100 mg (0.39 mmol) 5-(4-Chloro-2-ethyl-pyridin-3-ylethynyl)-pyridin-2-ylamine (A-30) using 88 mg (0.58 mmoL) 2,6-dimethyl-pyrid-4-yl boronic acid, 18 mg (0.02 mmol) Pd$_2$(dba)$_3$, 28 mg (0.06 mmol) XPhos and 107 mg (0.47 mmol) K$_3$PO$_4$ in a mixture of 6.0 mL DME. The reaction mixture is stirred twice under microwave irradiation at 190° C. for 300 min. The reaction mixture is concentrated in vaccuo and the crude product is purified by chromatography on silica gel using a DCM/MeOH-gradient. Yield: 17 mg (14%).

MW=328.4; [M+H]$^+$=329; $t_{Ret}$=1.61 min

Example 22

5-(6-Cyclopropyl-2'-ethyl-[3,4]bipyridinyl-3'-ylethynyl)-pyridin-2-ylamine

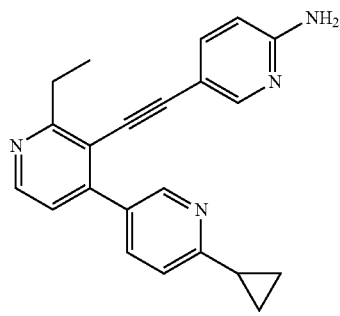 [SMILES: CCc1nccc(-c2ccc(C3CC3)nc2)c1C#Cc1ccc(N)nc1]

The title compound is synthesized according to general procedure GP3 starting from 150 mg (0.58 mmol) 5-(4-Chloro-2-ethyl-pyridin-3-ylethynyl)-pyridin-2-ylamine (A-30) using 142 mg (0.87 mmoL) 2-cyclopropyl-pyrid-5-yl boronic acid, 4.5 mg (0.03 mmol) Pd(PPh$_3$)$_4$ and 154 mg (1.11 mmol) K$_2$CO$_3$ in a mixture of 6.0 mL DME and 1.5 mL water. The reaction mixture is stirred twice under microwave irradiation at 150° C. for 120 min. The reaction mixture is concentrated in vaccuo and the crude product is purified by chromatography on silica gel using a DCM/MeOH-gradient. Yield: 68 mg (34%).

MW=340.4; [M+H]$^+$=341; $t_{Ret}$=1.51 min

Example 23

5-(2'-Ethyl-6-trifluoromethyl-[3,4]bipyridinyl-3'-ylethynyl)-pyridin-2-ylamine

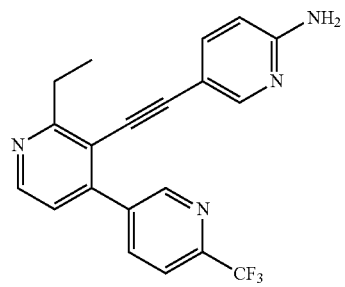 [SMILES: CCc1nccc(-c2ccc(C(F)(F)F)nc2)c1C#Cc1ccc(N)nc1]

The title compound is synthesized according to general procedure GP3 starting from 150 mg (0.58 mmol) 5-(4-Chloro-2-ethyl-pyridin-3-ylethynyl)-pyridin-2-ylamine (A-30) using 167 mg (0.87 mmoL) 2-trifluoromethyl-pyrid-5-yl boronic acid, 4.5 mg (0.03 mmol) Pd(PPh$_3$)$_4$ and 154 mg (1.11 mmol) K$_2$CO$_3$ in a mixture of 6.0 mL DME and 1.5 mL water. The reaction mixture is stirred twice under microwave irradiation at 150° C. for 120 min. The reaction mixture is concentrated in vaccuo and the crude product is purified by chromatography on silica gel using a DCM/MeOH-gradient. Yield: 15 mg (7%).

MW=368.4; [M+H]$^+$=369; $t_{Ret}$=1.56 min

Example 24

{4-[3-(6-Amino-pyridin-3-ylethynyl)-2-ethyl-pyridin-4-yl]-2-fluoro-phenyl}-morpholin-4-yl-methanone

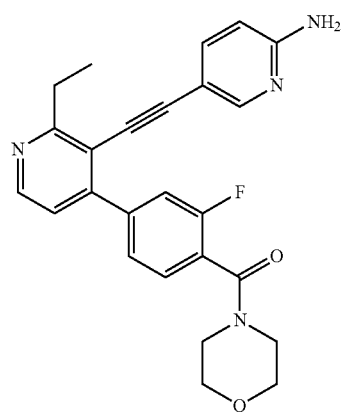 [SMILES: CCc1nccc(-c2ccc(C(=O)N3CCOCC3)c(F)c2)c1C#Cc1ccc(N)nc1]

The title compound is synthesized according to general procedure GP5 starting from 120 mg (0.33 mmol) 4-[3-(6-Amino-pyridin-3-ylethynyl)-2-ethyl-pyridin-4-yl]-2-fluoro-benzoic acid (A-38) using 43 mg (0.50 mmoL) morpholine, 139 mg (0.37 mmol) HATU and 96 µL DIEA in 1.2 mL DMF. After completion of the reaction, DMF is removed under reduced pressure and the product is purified by chromatography on silica gel using a DCM/MeOH-gradient. Yield: 66 mg (46%).

MW=430.5; [M+H]$^+$=431; $t_{Ret}$=1.60 min

Example 25

{4-[3-(6-Amino-pyridin-3-ylethynyl)-2-ethyl-pyridin-4-yl]-2-fluoro-phenyl}-piperazin-1-yl-methanone

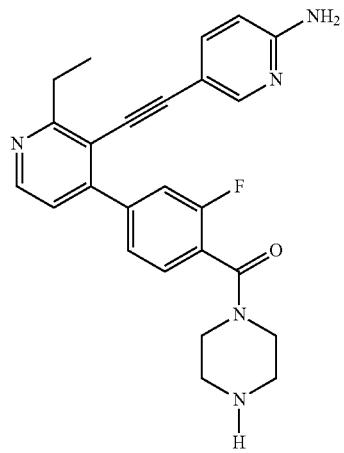 [SMILES: CCc1nccc(-c2ccc(C(=O)N3CCNCC3)c(F)c2)c1C#Cc1ccc(N)nc1]

The title compound is synthesized according to general procedure GP5 starting from 100 mg (0.28 mmol) 4-[3-(6-Amino-pyridin-3-ylethynyl)-2-ethyl-pyridin-4-yl]-2-fluoro-benzoic acid (A-38) using 29 mg (0.33 mmoL) piperazine, 116 mg (0.30 mmol) HATU and 81 µL DIPEA in 1 mL DMF. After completion of the reaction, the reaction mixture is filtered and the product is isolated from the obtained solution by RP-HPLC using a H$_2$O/MeOH-gradient. Yield: 8 mg (6%).

MW=429.5; [M+H]$^+$=430; $t_{Ret}$=1.29 min

Example 26

{4-[3-(6-Amino-pyridin-3-ylethynyl)-2-ethyl-pyridin-4-yl]-2-fluoro-phenyl}-(4-methyl-piperazin-1-yl)-methanone

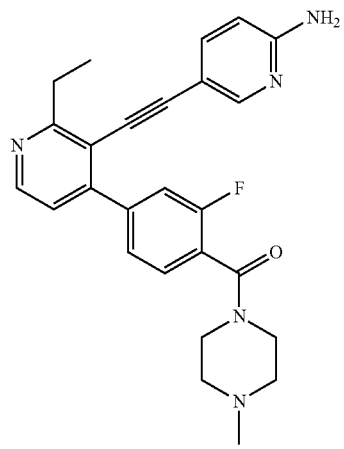 [SMILES: CCc1nccc(-c2ccc(C(=O)N3CCN(C)CC3)c(F)c2)c1C#Cc1ccc(N)nc1]

The title compound is synthesized according to general procedure GP5 starting from 120 mg (0.33 mmol) 4-[3-(6-Amino-pyridin-3-ylethynyl)-2-ethyl-pyridin-4-yl]-2-fluoro-benzoic acid (A-38) using 55 µL (0.50 mmoL) N-methyl piperazine, 139 mg (0.37 mmol) HATU and 96 µL DIPEA in 1.2 mL DMF. After completion of the reaction, the reaction mixture is filtered and the product is isolated from the obtained solution by RP-HPLC using a H$_2$O/MeOH-gradient. Yield: 55 mg (37%).

MW=443.5; [M+H]$^+$=444; $t_{Ret}$=1.68 min

Example 27

{4-[3-(6-Amino-pyridin-3-ylethynyl)-2-ethyl-pyridin-4-yl]-2-chloro-phenyl}-(4-methyl-piperazin-1-yl)-methanone

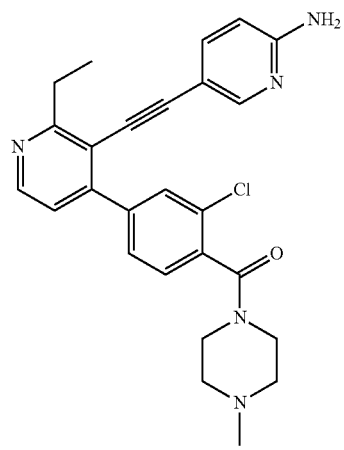 [SMILES: CCc1nccc(-c2ccc(C(=O)N3CCN(C)CC3)c(Cl)c2)c1C#Cc1ccc(N)nc1]

The title compound is synthesized according to general procedure GP5 starting from 100 mg (0.27 mmol) 4-[3-(6-Amino-pyridin-3-ylethynyl)-2-ethyl-pyridin-4-yl]-2-chloro-benzoic acid (A-40) using 40 mg (0.40 mmoL) N-methyl piperazine, 102 mg (0.53 mmol) EDC, 72 mg (0.53 mmol) HOBt and 68 mg (0.53 mmol) DIPEA in 1.2 mL DMF. After completion of the reaction, the reaction mixture is filtered and the product is isolated from the obtained solution by RP-HPLC using a H$_2$O/ACN-gradient. Yield: 66 mg (54%).

MW=460.0; [M+H]$^+$=460/62; $t_{Ret}$=1.64 min

Example 28

{4-[2-Ethyl-3-(6-methylamino-pyridin-3-ylethynyl)-pyridin-4-yl]-2-fluoro-phenyl}-(4-methyl-piperazin-1-yl)-methanone

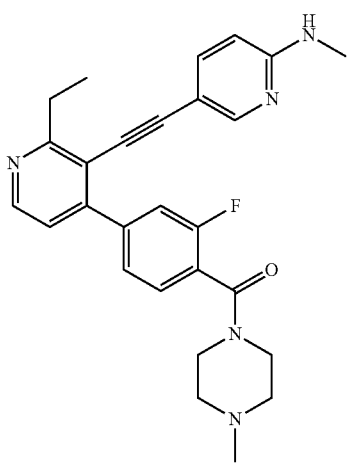 [SMILES: CCc1nccc(-c2ccc(C(=O)N3CCN(C)CC3)c(F)c2)c1C#Cc1ccc(NC)nc1]

The title compound is synthesized according to general procedure GP5 starting from 100 mg (0.27 mmol) 4-[2-Ethyl-3-(6-methylamino-pyridin-3-ylethynyl)-pyridin-4-yl]-2-fluoro-benzoic acid (A-46) using 50 µL (0.45 mmoL) N-methyl piperazine, 101 mg (0.27 mmol) HATU and 50 µL (0.29 mmol) DIPEA in 1.5 mL DMF. After completion of the reaction, the reaction mixture is filtered and the product is isolated from the obtained solution by RP-HPLC using a H$_2$O/ACN-gradient. Yield: 70 mg (58%).

MW=457.6; [M+H]$^+$=458; $t_{Ret}$=1.70 min

Example 29

{4-[3-(6-Amino-pyridin-3-ylethynyl)-2-ethyl-pyridin-4-yl]-2-methoxy-phenyl}-(4-methyl-piperazin-1-yl)-methanone

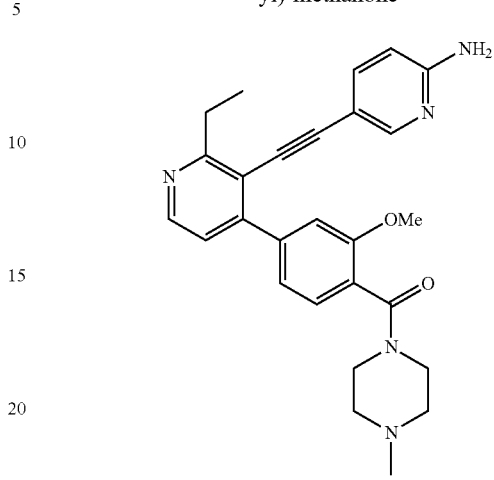

The title compound is synthesized according to general procedure GP5 starting from 70 mg (0.19 mmol) 4-[3-(6-Amino-pyridin-3-ylethynyl)-2-ethyl-pyridin-4-yl]-2-methoxy-benzoic acid (A-42) using 42 µL (0.38 mmoL) N-methyl piperazine, 71 mg (0.19 mmol) HATU and 35 µL (0.21 mmol) DIPEA in 1.0 mL DMF. After completion of the reaction, the reaction mixture is filtered and the product is isolated from the obtained solution by RP-HPLC using a H$_2$O/ACN-gradient. Yield: 81 mg (95%).

MW=455.6; [M+H]$^+$=456; $t_{Ret}$=1.57 min

Example 30

{4-[3-(6-Amino-pyridin-3-ylethynyl)-2-ethyl-pyridin-4-yl]-2-fluoro-phenyl}-(4-ethyl-piperazin-1-yl)-methanone

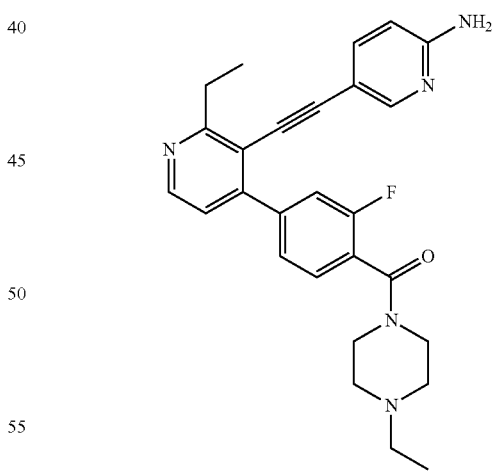

The title compound is synthesized according to general procedure GP5 starting from 100 mg (0.28 mmol) 4-[3-(6-Amino-pyridin-3-ylethynyl)-2-ethyl-pyridin-4-yl]-2-fluoro-benzoic acid (A-38) using 38 mg (0.33 mmoL) N-ethyl piperazine, 116 mg (0.30 mmol) HATU and 81 µL DIPEA in 1 mL DMF. After completion of the reaction, the reaction mixture is filtered and the product is isolated from the obtained solution by RP-HPLC using a H$_2$O/MeOH-gradient. Yield: 36 mg (28%).

MW=457.6; [M+H]$^+$=458; $t_{Ret}$=1.66 min

Example 31

{4-[3-(6-Amino-pyridin-3-ylethynyl)-2-ethyl-pyridin-4-yl]-2-chloro-phenyl}-(4-ethyl-piperazin-1-yl)-methanone

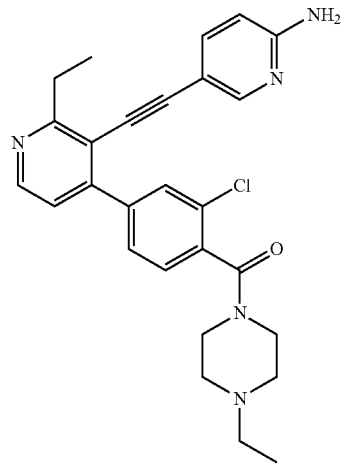 [SMILES: CCc1nccc(-c2ccc(C(=O)N3CCN(CC)CC3)c(Cl)c2)c1C#Cc1ccc(N)nc1]

The title compound is synthesized according to general procedure GP5 starting from 100 mg (0.27 mmol) 4-[3-(6-Amino-pyridin-3-ylethynyl)-2-ethyl-pyridin-4-yl]-2-chloro-benzoic acid (A-40) using 40 mg (0.40 mmoL) N-ethyl piperazine, 102 mg (0.53 mmol) EDC, 72 mg (0.53 mmol) HOBt and 68 mg (0.53 mmol) DIPEA in 1.2 mL DMF. After completion of the reaction, the reaction mixture is filtered and the product is isolated from the obtained solution by RP-HPLC using a H$_2$O/ACN-gradient. Yield: 67 mg (53%).

MW=474.0; [M+H]$^+$=474/476; t$_{Ret}$=1.73 min

Example 32

{4-[2-Ethyl-3-(6-methylamino-pyridin-3-ylethynyl)-pyridin-4-yl]-2-fluoro-phenyl}-(4-ethyl-piperazin-1-yl)-methanone

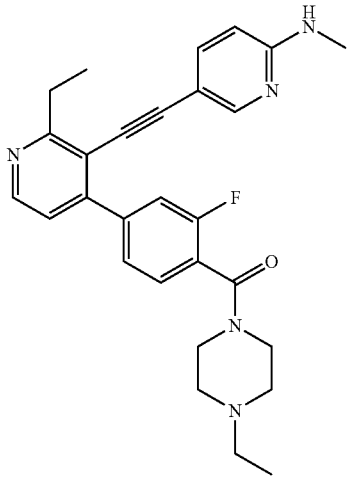 [SMILES: CCc1nccc(-c2ccc(C(=O)N3CCN(CC)CC3)c(F)c2)c1C#Cc1ccc(NC)nc1]

The title compound is synthesized according to general procedure GP5 starting from 100 mg (0.28 mmol) 4-[2-Ethyl-3-(6-methylamino-pyridin-3-ylethynyl)-pyridin-4-yl]-2-fluoro-benzoic acid (A-46) using 55 µL (0.33 mmol) N-ethyl piperazine, 101 mg (0.27 mmol) HATU and 50 µL DIPEA in 1.5 mL DMF. After completion of the reaction, the reaction mixture is filtered and the product is isolated from the obtained solution by RP-HPLC using a H$_2$O/ACN-gradient. Yield: 82 mg (65%).

MW=471.6; [M+H]$^+$=472; t$_{Ret}$=1.79 min

Example 33

{4-[3-(6-Amino-pyridin-3-ylethynyl)-2-ethyl-pyridin-4-yl]-2-methoxy-phenyl}-(4-ethyl-piperazin-1-yl)-methanone

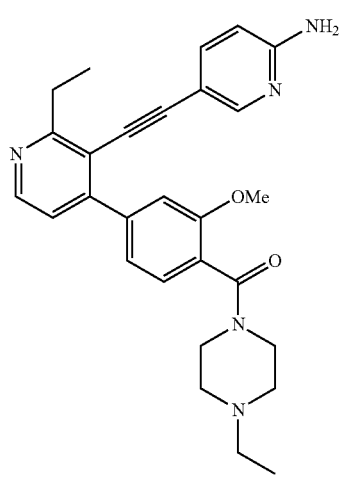 [SMILES: CCc1nccc(-c2ccc(C(=O)N3CCN(CC)CC3)c(OC)c2)c1C#Cc1ccc(N)nc1]

The title compound is synthesized according to general procedure GP5 starting from 70 mg (0.19 mmol) 4-[3-(6-Amino-pyridin-3-ylethynyl)-2-ethyl-pyridin-4-yl]-2-methoxy-benzoic acid (A-42) using 42 mg (0.38 mmol) N-ethyl piperazine, 71 mg (0.19 mmol) HATU and 35 µL (0.21 mmol) DIPEA in 1.0 mL DMF. After completion of the reaction, the reaction mixture is filtered and the product is isolated from the obtained solution by RP-HPLC using a H$_2$O/ACN-gradient. Yield: 85 mg (97%).

MW=469.6; [M+H]$^+$=470; t$_{Ret}$=1.64 min

Example 34

{4-[3-(6-Amino-pyridin-3-ylethynyl)-2-ethyl-pyridin-4-yl]-2-fluoro-phenyl}-(4-cyclopropyl-piperazin-1-yl)-methanone

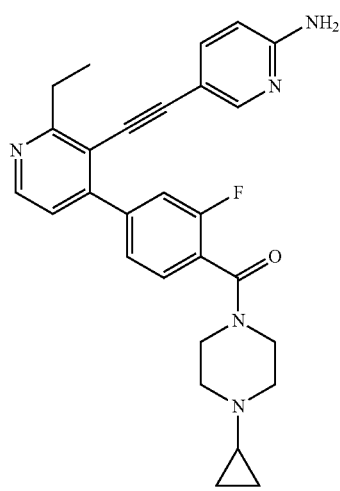 [SMILES: CCc1nccc(-c2ccc(C(=O)N3CCN(C4CC4)CC3)c(F)c2)c1C#Cc1ccc(N)nc1]

The title compound is synthesized according to general procedure GP5 starting from 120 mg (0.33 mmol) 4-[3-(6-Amino-pyridin-3-ylethynyl)-2-ethyl-pyridin-4-yl]-2-fluoro-benzoic acid (A-38) using 63 mg (0.50 mmoL) N-cyclopropyl piperazine, 139 mg (0.37 mmol) HATU and 96 µL DIPEA in 1.2 mL DMF. After completion of the reaction, the reaction mixture is filtered and the product is isolated from the obtained solution by RP-HPLC using a H$_2$O/ACN-gradient. Yield: 30 mg (20%).

MW=469.6; [M+H]$^+$=470; t$_{Ret}$=1.82 min

Example 35

{4-[3-(6-Amino-pyridin-3-ylethynyl)-2-ethyl-pyridin-4-yl]-2-fluoro-phenyl}-[4-(tetrahydro-pyran-4-yl)-piperazin-1-yl]-methanone

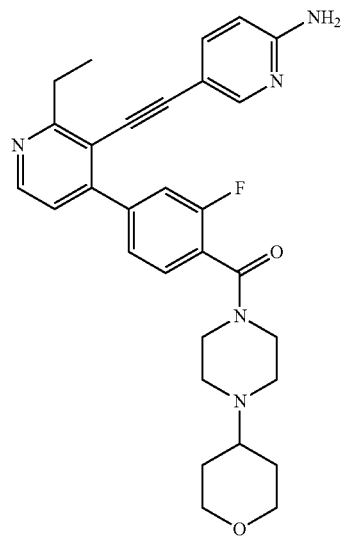 [SMILES: CCc1nccc(-c2ccc(C(=O)N3CCN(C4CCOCC4)CC3)c(F)c2)c1C#Cc1ccc(N)nc1]

The title compound is synthesized according to general procedure GP5 starting from 320 mg (0.89 mmol) 4-[3-(6-Amino-pyridin-3-ylethynyl)-2-ethyl-pyridin-4-yl]-2-fluoro-benzoic acid (A-38) using 181 mg (1.06 mmol) 1-tetrahydro-pyran-4-yl piperazine, 370 mg (0.97 mmol) HATU and 258 µL DIPEA in 3 mL DMF. After completion of the reaction, the reaction mixture is filtered and the product is isolated from the obtained solution by RP-HPLC using a $H_2O$/MeOH-gradient. Yield: 90 mg (20%).

MW=513.6; [M+H]$^+$=514; $t_{Ret}$=1.62 min

Example 36

{4-[3-(6-Amino-pyridin-3-ylethynyl)-2-ethyl-pyridin-4-yl]-2-chloro-phenyl}-(4-morpholin-4-yl-piperidin-1-yl)-methanone The title compound is synthesized according to general procedure GP5 starting from 100 mg (0.27 mmol) 4-[3-(6-Amino-pyridin-3-ylethynyl)-2-ethyl-pyridin-4-yl]-2-chloro-benzoic acid (A-40) using 68 mg (0.40 mmoL) 4-piperidin-4-yl morpholine, 102 mg (0.53 mmol) EDC, 72 mg (0.53 mmol) HOBt and 68 mg (0.53 mmol) DIPEA in 1.2 mL DMF. After completion of the reaction, the reaction mixture is filtered and the product is isolated from the obtained solution by RP-HPLC using a $H_2O$/ACN-gradient. Yield: 73 mg (51%).

MW=530.1; [M+H]$^+$=530/532; $t_{Ret}$=1.66 min

Example 37

{4-[2-Ethyl-3-(6-methylamino-pyridin-3-ylethynyl)-pyridin-4-yl]-2-fluoro-phenyl}-[4-(tetrahydro-pyran-4-yl)-piperazin-1-yl]-methanone The title compound is synthesized according to general procedure GP5 starting from 100 mg (0.27 mmol) 4-[2-Ethyl-3-(6-methylamino-pyridin-3-ylethynyl)-pyridin-4-yl]-2-fluoro-benzoic acid (A-46) using 68 mg (0.40 mmoL) tetrahydro-pyran-4-yl piperazine, 101 mg (0.27 mmol) HATU and 50 µL DIPEA in 1.5 mL DMF. After completion of the reaction, the reaction mixture is filtered and the product is isolated from the obtained solution by RP-HPLC using a $H_2O$/ACN-gradient. Yield: 59 mg (42%).

MW=527.6; [M+H]$^+$=528; $t_{Ret}$=1.81 min

Example 38

1-(4-{4-[3-(6-Amino-pyridin-3-ylethynyl)-2-ethyl-pyridin-4-yl]-2-fluoro-benzoyl}-piperazin-1-yl)-ethanone

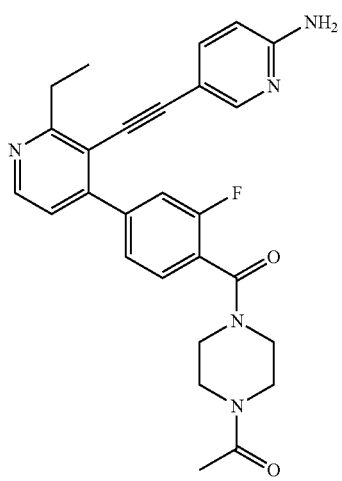 [SMILES: CCc1nccc(-c2ccc(C(=O)N3CCN(C(C)=O)CC3)c(F)c2)c1C#Cc1ccc(N)nc1]

The title compound is synthesized according to general procedure GP5 starting from 100 mg (0.28 mmol) 4-[3-(6-Amino-pyridin-3-ylethynyl)-2-ethyl-pyridin-4-yl]-2-fluoro-benzoic acid (A-38) using 46 mg (0.36 mmoL) N-acetyl piperazine, 116 mg (0.30 mmol) HATU and 81 µL DIPEA in 1 mL DMF. After completion of the reaction, the reaction mixture is filtered and the product is isolated from the obtained solution by RP-HPLC using a $H_2O$/ACN-gradient. Yield: 69 mg (53%).

MW=471.5; $[M+H]^+$=472; $t_{Ret}$=1.52 min

Example 39

4-[3-(6-Amino-pyridin-3-ylethynyl)-2-ethyl-pyridin-4-yl]-2-fluoro-N-(2-methoxy-ethyl)-N-methyl-benzamide

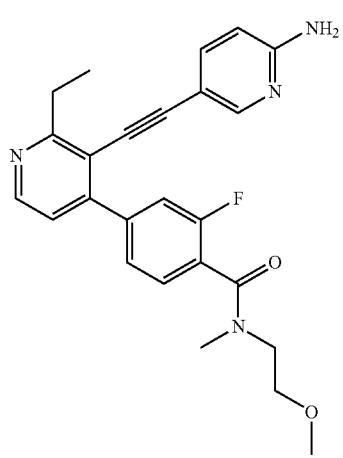 [SMILES: CCc1nccc(-c2ccc(C(=O)N(C)CCOC)c(F)c2)c1C#Cc1ccc(N)nc1]

The title compound is synthesized according to general procedure GP5 starting from 320 mg (0.89 mmol) 4-[3-(6-Amino-pyridin-3-ylethynyl)-2-ethyl-pyridin-4-yl]-2-fluoro-benzoic acid (A-38) using 95 mg (1.06 mmoL) 2-methoxy methylamine, 370 mg (0.97 mmol) HATU and 258 µL DIPEA in 3 mL DMF. After completion of the reaction, the reaction mixture is filtered and the product is isolated from the obtained solution by RP-HPLC using a $H_2O$/ACN-gradient. Yield: 130 mg (34%).

MW=432.5; $[M+H]^+$=433; $t_{Ret}$=1.62 min

TABLE 1

| | Examples (cont.) | | | |
|---|---|---|---|---|
| No. | Structures | Starting material | MW | $[M + H]^+$ | $t_{Ret}$ |
| 40 | | | 355.4 | M + H = 356 | tR = 1.62 |

TABLE 1-continued

Examples (cont.)

| No. | Structures | Starting material | MW | [M + H]+ | t$_{Ret}$ |
|---|---|---|---|---|---|
| 41 | 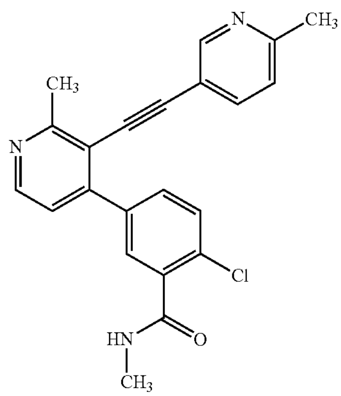 [SMILES: CNC(=O)c1cc(-c2ccnc(C)c2C#Cc2ccc(C)nc2)ccc1Cl] | | 375.9 | M + H = 376 | tR = 1.61 |
| 42 | 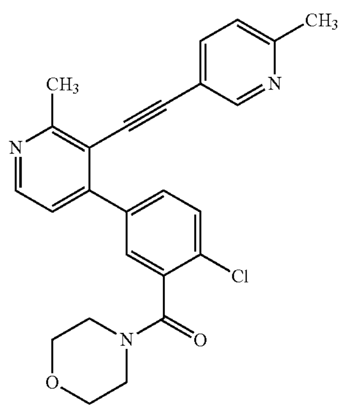 [SMILES: Cc1ccc(C#Cc2c(-c3ccc(Cl)c(C(=O)N4CCOCC4)c3)ccnc2C)cn1] | A-28 | 432.9 | | |
| 43 | 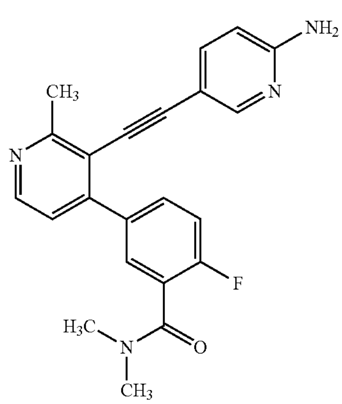 [SMILES: Cc1nccc(-c2ccc(F)c(C(=O)N(C)C)c2)c1C#Cc1ccc(N)nc1] | A-28 | 374.4 | | |

TABLE 1-continued

Examples (cont.)

| No. | Structures | Starting material | MW | [M + H]+ | $t_{Ret}$ |
|-----|-----------|-------------------|------|----------|-----------|
| 44 | 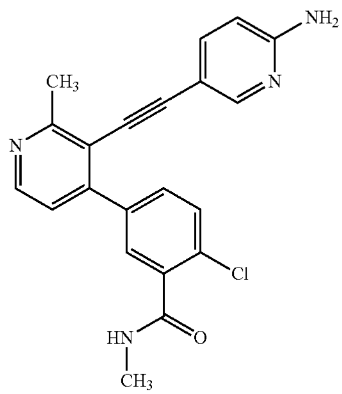 [SMILES: CNC(=O)c1cc(-c2ccnc(C)c2C#Cc2ccc(N)nc2)ccc1Cl] | A-28 | 376.8 | | |
| 45 | 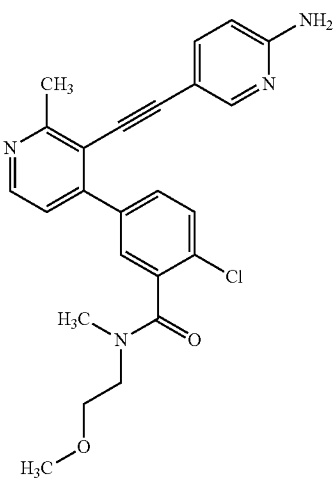 [SMILES: COCCN(C)C(=O)c1cc(-c2ccnc(C)c2C#Cc2ccc(N)nc2)ccc1Cl] | | 434.9 | | |
| 46 | 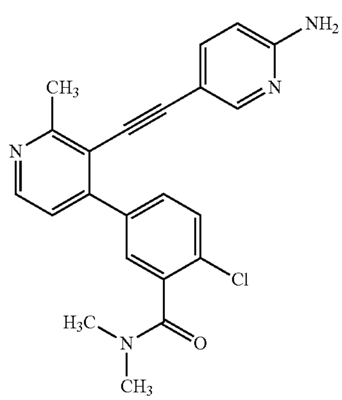 [SMILES: Cc1nccc(-c2ccc(Cl)c(C(=O)N(C)C)c2)c1C#Cc1ccc(N)nc1] | A-28 | 390.9 | | |
| 47 | 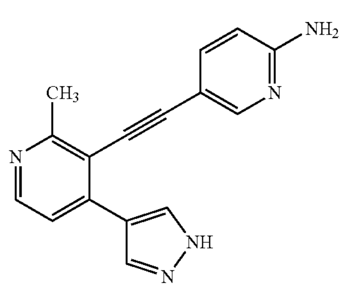 [SMILES: Cc1nccc(-c2cn[nH]c2)c1C#Cc1ccc(N)nc1] | A-28 | 275.3 | M + H = 276 | tR = 1.19 |

TABLE 1-continued

Examples (cont.)

| No. | Structures | Starting material | MW | [M + H]+ | $t_{Ret}$ |
|---|---|---|---|---|---|
| 48 | 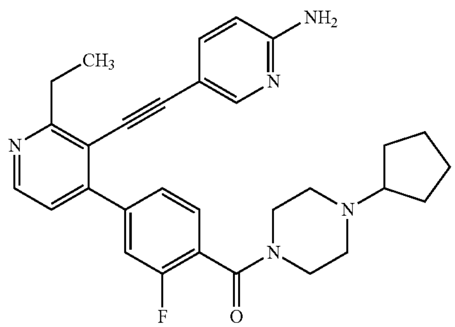 [SMILES: CCc1nccc(-c2ccc(C(=O)N3CCN(C4CCCC4)CC3)c(F)c2)c1C#Cc1ccc(N)nc1] | A-38 | 497.6 | M + H = 498 | tR = 1.89 |
| 49 | 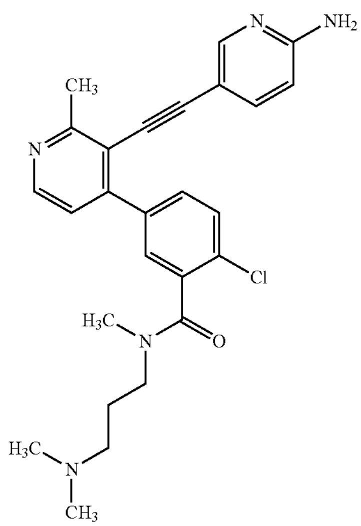 [SMILES: Cc1nccc(-c2ccc(Cl)c(C(=O)N(C)CCCN(C)C)c2)c1C#Cc1ccc(N)nc1] | | 462.0 | | |
| 50 | 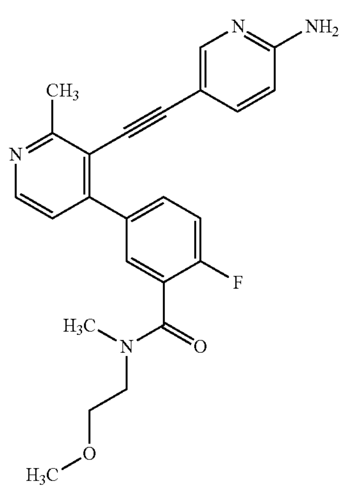 [SMILES: COCCN(C)C(=O)c1cc(-c2ccnc(C)c2C#Cc2ccc(N)nc2)ccc1F] | | 418.5 | | |

TABLE 1-continued

Examples (cont.)

| No. | Structures | Starting material | MW | [M + H]+ | t_Ret |
|---|---|---|---|---|---|
| 51 | 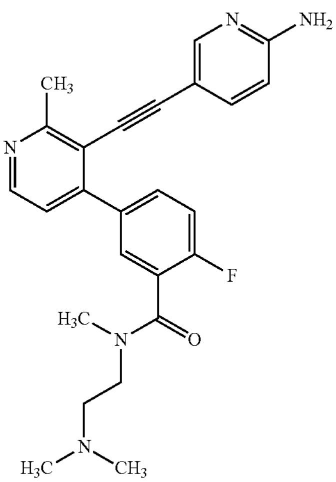 [SMILES: Cc1nccc(-c2ccc(F)c(C(=O)N(C)CCN(C)C)c2)c1C#Cc1ccc(N)nc1] | | 431.5 | | |
| 52 | 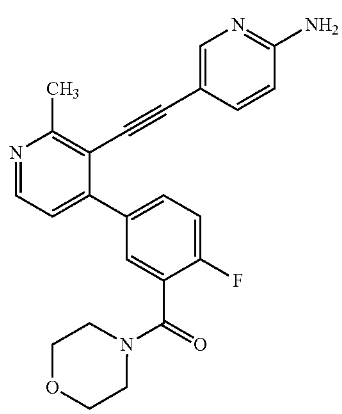 [SMILES: Cc1nccc(-c2ccc(F)c(C(=O)N3CCOCC3)c2)c1C#Cc1ccc(N)nc1] | | 416.5 | | |
| 53 | 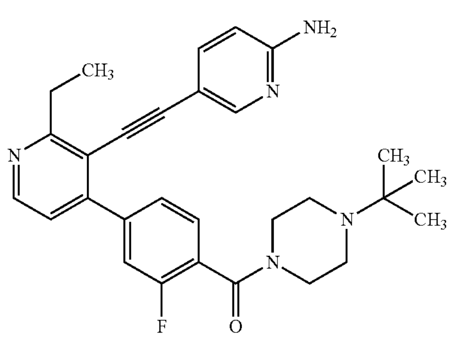 [SMILES: CCc1nccc(-c2ccc(C(=O)N3CCN(C(C)(C)C)CC3)c(F)c2)c1C#Cc1ccc(N)nc1] | A-38 | 485.6 | M + H = 486 | tR = 1.83 |

TABLE 1-continued

Examples (cont.)

| No. | Structures | Starting material | MW | [M + H]⁺ | t_Ret |
|---|---|---|---|---|---|
| 54 | 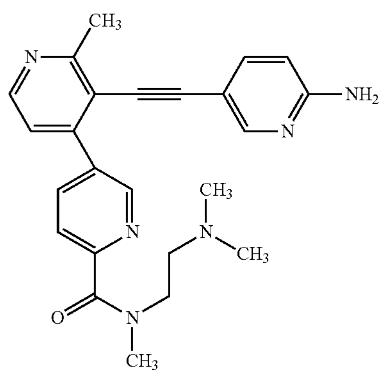 [SMILES: Cc1nccc(-c2ccc(C(=O)N(C)CCN(C)C)nc2)c1C#Cc1ccc(N)nc1] | | 414.5 | M + H = 415 (358) | tR = 1.32 (1.25) |
| 55 | 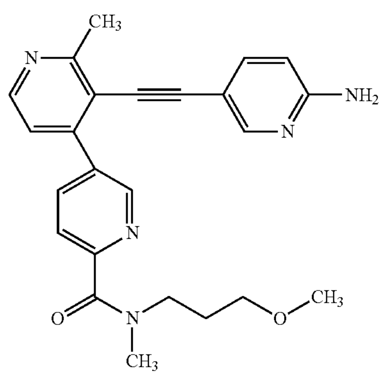 [SMILES: COCCCN(C)C(=O)c1ccc(-c2ccnc(C)c2C#Cc2ccc(N)nc2)cn1] | | 415.5 | M + H = 416 (358) | tR = 1.35 (1.25) |
| 56 | 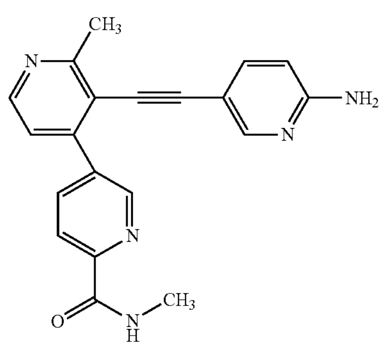 [SMILES: CNC(=O)c1ccc(-c2ccnc(C)c2C#Cc2ccc(N)nc2)cn1] | | 343.4 | M + H = 344 | tR = 1.30 |
| 57 | 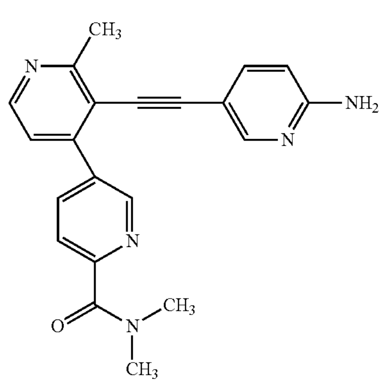 [SMILES: Cc1nccc(-c2ccc(C(=O)N(C)C)nc2)c1C#Cc1ccc(N)nc1] | | 357.4 | M + H = 358 | tR = 1.25 |

TABLE 1-continued
Examples (cont.)
| No. | Structures | Starting material | MW | [M + H]⁺ | $t_{Ret}$ |
|---|---|---|---|---|---|
| 58 | 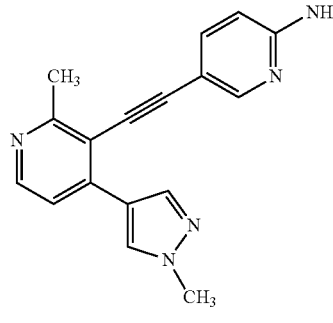 | A-28 | 289.3 | M + H = 290 (497) | tR = 1.23 (1.53) |
| 59 | 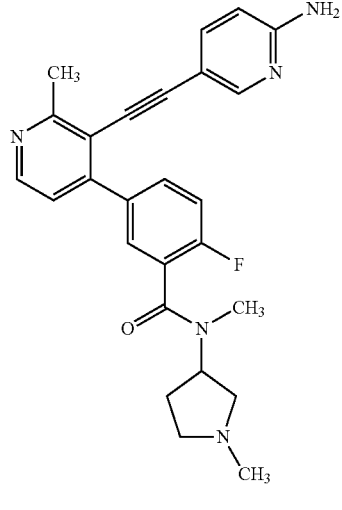 [SMILES: Cc1nccc(-c2ccc(F)c(C(=O)N(C)C3CCN(C)C3)c2)c1C#Cc1ccc(N)nc1] | | 443.5 | M + H = 444 | tR = 1.49 |
| 60 | 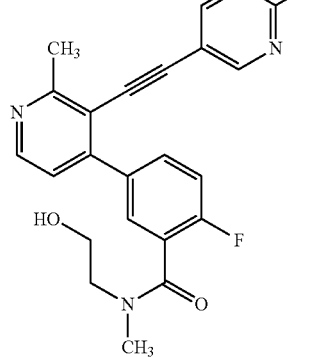 | | 404.4 | M + H = 405 | tR = 1.30 |

TABLE 1-continued
Examples (cont.)
| No. | Structures | Starting material | MW | [M + H]⁺ | $t_{Ret}$ |
|---|---|---|---|---|---|
| 61 | 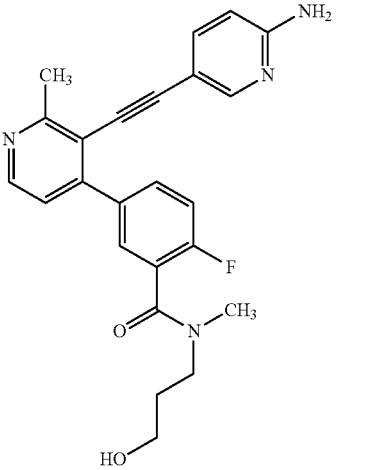 [SMILES: Cc1nccc(-c2ccc(F)c(C(=O)N(C)CCCO)c2)c1C#Cc1ccc(N)nc1] | | 418.5 | M + H = 419 | tR = 1.35 |
| 62 | 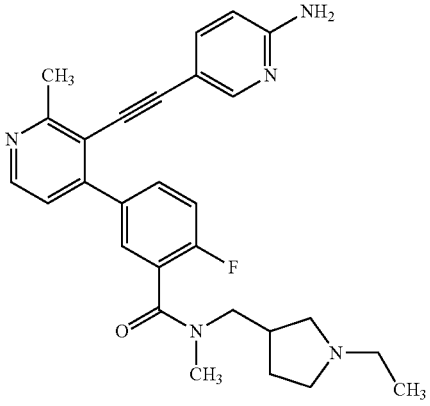 [SMILES: CCN1CCC(CN(C)C(=O)c2cc(-c3ccnc(C)c3C#Cc3ccc(N)nc3)ccc2F)C1] | | 471.6 | M + H = 472 | tR = 1.59 |
| 63 | 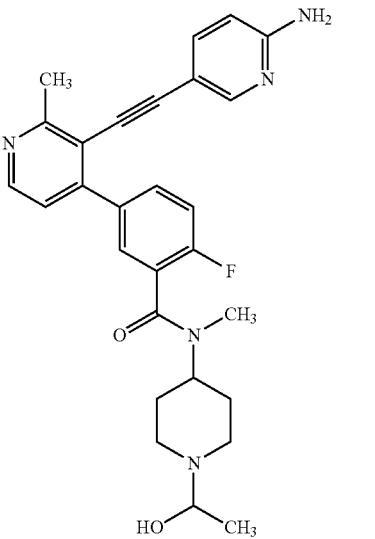 [SMILES: Cc1nccc(-c2ccc(F)c(C(=O)N(C)C3CCN(C(C)O)CC3)c2)c1C#Cc1ccc(N)nc1] | | 485.6 | M + H = 486 | tR = 1.69 |

TABLE 1-continued
Examples (cont.)
| No. | Structures | Starting material | MW | [M + H]⁺ | t$_{Ret}$ |
|---|---|---|---|---|---|
| 64 | 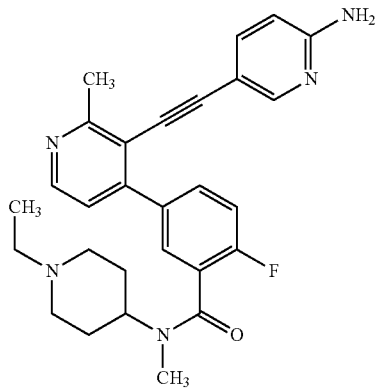 [SMILES: CCN1CCC(N(C)C(=O)c2cc(-c3ccnc(C)c3C#Cc3ccc(N)nc3)ccc2F)CC1] | | 471.6 | M + H = 472 | tR = 1.56 |
| 65 | 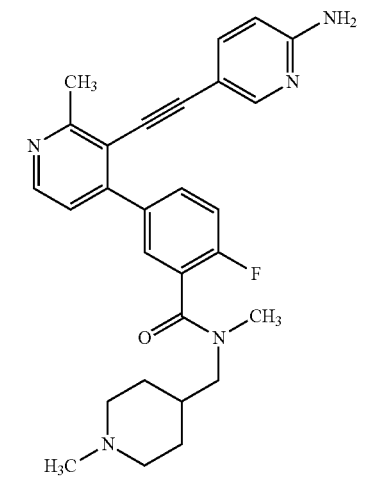 [SMILES: Cc1nccc(-c2ccc(F)c(C(=O)N(C)CC3CCN(C)CC3)c2)c1C#Cc1ccc(N)nc1] | | 471.6 | M + H = 472 | tR = 1.57 |
| 66 | 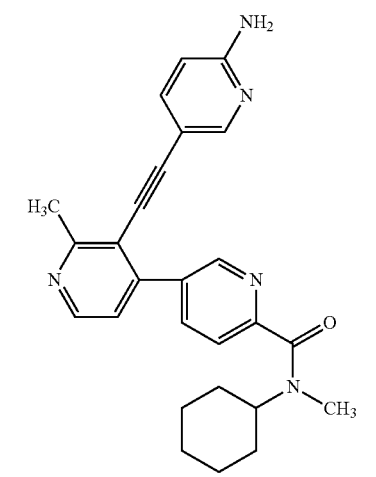 [SMILES: Cc1nccc(-c2ccc(C(=O)N(C)C3CCCCC3)nc2)c1C#Cc1ccc(N)nc1] | | 425.5 | M + H = 426 | tR = 1.65 |

TABLE 1-continued
Examples (cont.)
| No. | Structures | Starting material | MW | [M + H]+ | $t_{Ret}$ |
|---|---|---|---|---|---|
| 67 | 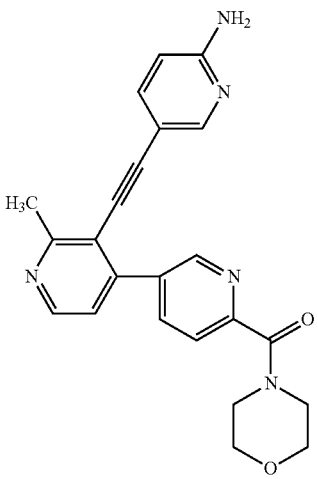 [SMILES: Cc1nccc(-c2ccc(C(=O)N3CCOCC3)nc2)c1C#Cc1ccc(N)nc1] | | 399.5 | 29M + H = 400 | tR = 1.29 |
| 68 | 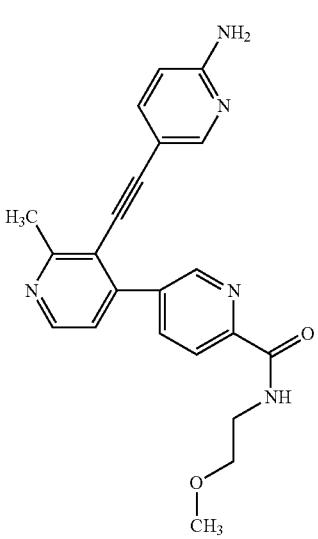 [SMILES: COCCNC(=O)c1ccc(-c2ccnc(C)c2C#Cc2ccc(N)nc2)cn1] | | 387.4 | M + H = 388 | tR = 1.44 |
| 69 | 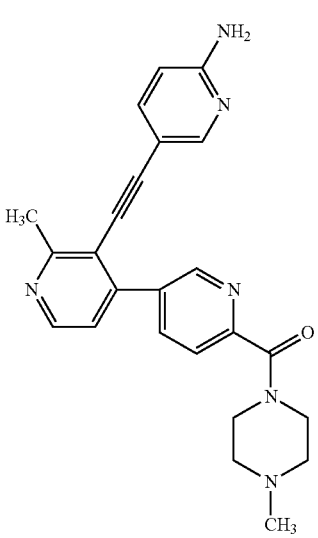 [SMILES: Cc1nccc(-c2ccc(C(=O)N3CCN(C)CC3)nc2)c1C#Cc1ccc(N)nc1] | | 412.5 | M + H = 413 | tR = 1.30 |

TABLE 1-continued
Examples (cont.)
| No. | Structures | Starting material | MW | [M + H]+ | $t_{Ret}$ |
|---|---|---|---|---|---|
| 70 | 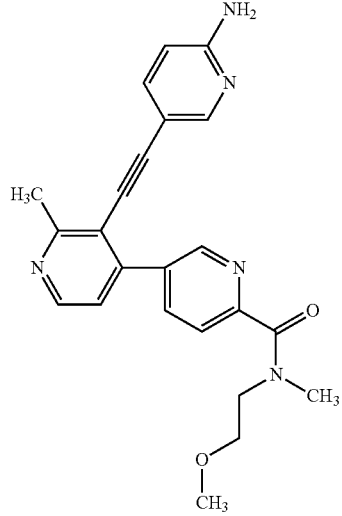 [SMILES: COCCN(C)C(=O)c1ccc(-c2ccnc(C)c2C#Cc2ccc(N)nc2)cn1] | | 401.5 | M + H = 402 | tR = 1.35 |
| 71 | 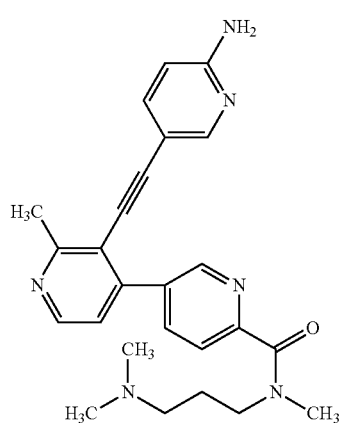 [SMILES: Cc1nccc(-c2ccc(C(=O)N(C)CCCN(C)C)nc2)c1C#Cc1ccc(N)nc1] | | 428.5 | M + H = 429 | tR = 1.39 |
| 72 | 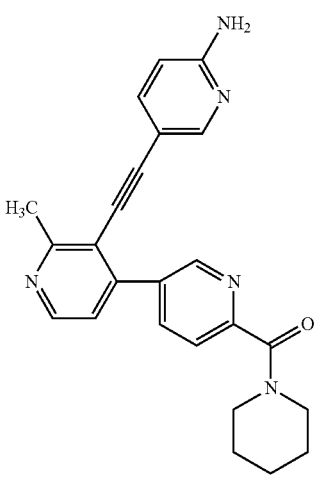 [SMILES: Cc1nccc(-c2ccc(C(=O)N3CCCCC3)nc2)c1C#Cc1ccc(N)nc1] | | 397.5 | M + H = 398 | tR = 1.47 |

TABLE 1-continued
Examples (cont.)
| No. | Structures | Starting material | MW | [M + H]+ | $t_{Ret}$ |
|---|---|---|---|---|---|
| 73 | 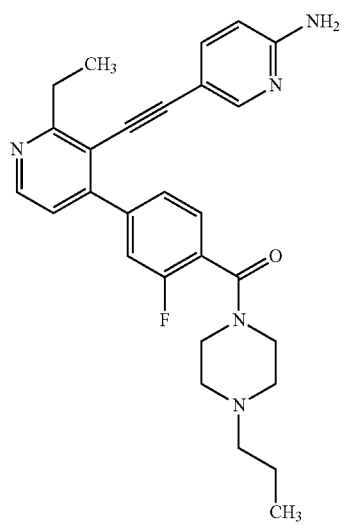 [SMILES: CCCN1CCN(C(=O)c2ccc(-c3ccnc(CC)c3C#Cc3ccc(N)nc3)cc2F)CC1] | A-38 | 471.6 | M + H = 472 | tR = 1.79 |
| 74 | 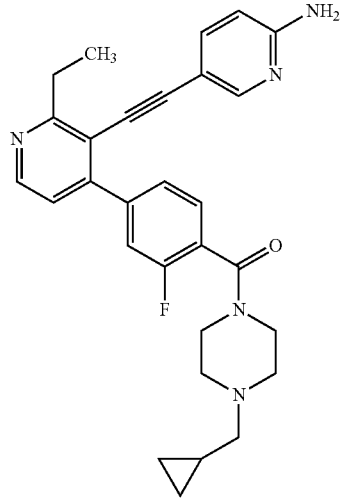 [SMILES: CCc1nccc(-c2ccc(C(=O)N3CCN(CC4CC4)CC3)c(F)c2)c1C#Cc1ccc(N)nc1] | A-38 | 483.6 | M + H = 484 | tR = 1.78 |
| 75 | 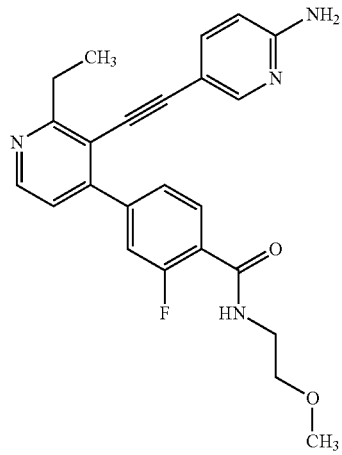 [SMILES: CCc1nccc(-c2ccc(C(=O)NCCOC)c(F)c2)c1C#Cc1ccc(N)nc1] | A-38 | 418.5 | M + H = 419 | tR = 1.58 |

TABLE 1-continued

Examples (cont.)

| No. | Structures | Starting material | MW | [M + H]+ | $t_{Ret}$ |
|---|---|---|---|---|---|
| 76 | 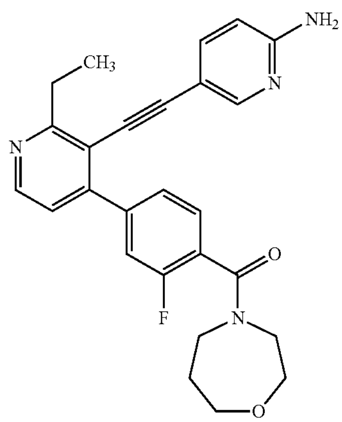 [SMILES: CCc1nccc(-c2ccc(C(=O)N3CCCOCC3)c(F)c2)c1C#Cc1ccc(N)nc1] | A-38 | 444.5 | M + H = 445 | tR = 1.58 |
| 77 | 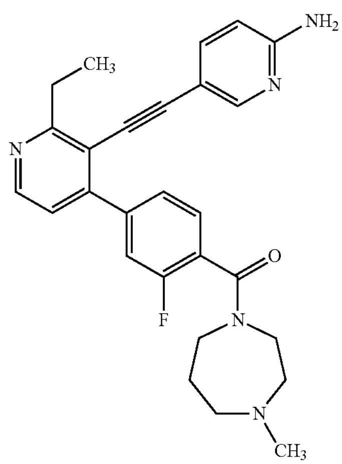 [SMILES: CCc1nccc(-c2ccc(C(=O)N3CCCN(C)CC3)c(F)c2)c1C#Cc1ccc(N)nc1] | A-38 | 457.6 | M + H = 458 | tR = 1.58 |
| 78 | 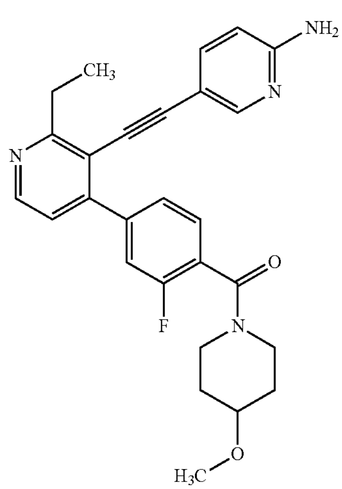 [SMILES: CCc1nccc(-c2ccc(C(=O)N3CCC(OC)CC3)c(F)c2)c1C#Cc1ccc(N)nc1] | A-38 | 458.5 | M + H = 459 | tR = 1.68 |

TABLE 1-continued

Examples (cont.)

| No. | Structures | Starting material | MW | [M + H]+ | t$_{Ret}$ |
|---|---|---|---|---|---|
| 79 | 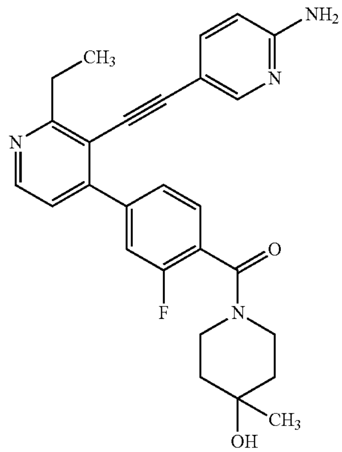 [SMILES: CCc1nccc(-c2ccc(C(=O)N3CCC(C)(O)CC3)c(F)c2)c1C#Cc1ccc(N)nc1] | A-38 | 458.5 | M + H = 459 | tR = 1.56 |
| 80 | 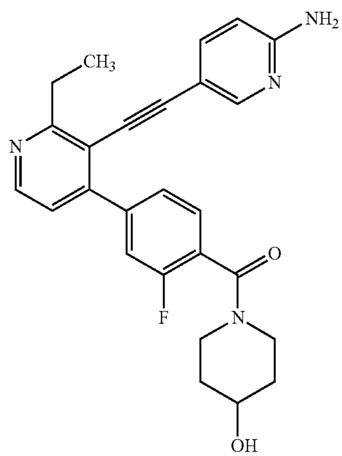 [SMILES: CCc1nccc(-c2ccc(C(=O)N3CCC(O)CC3)c(F)c2)c1C#Cc1ccc(N)nc1] | A-38 | 444.5 | M + H = 445 | tR = 1.49 |
| 81 | 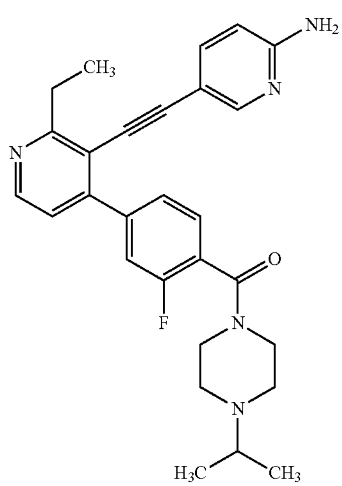 [SMILES: CCc1nccc(-c2ccc(C(=O)N3CCN(C(C)C)CC3)c(F)c2)c1C#Cc1ccc(N)nc1] | A-38 | 471.6 | M + H = 472 | tR = 1.75 |

TABLE 1-continued

Examples (cont.)

| No. | Structures | Starting material | MW | [M + H]+ | t$_{Ret}$ |
|---|---|---|---|---|---|
| 82 | 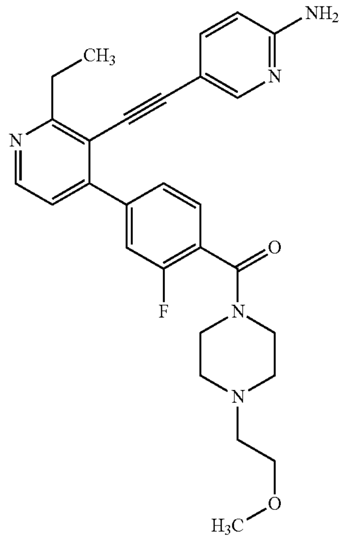 [SMILES: CCc1nccc(-c2ccc(C(=O)N3CCN(CCOC)CC3)c(F)c2)c1C#Cc1ccc(N)nc1] | A-38 | 487.6 | M + H = 488 | tR = 1.62 |
| 83 | 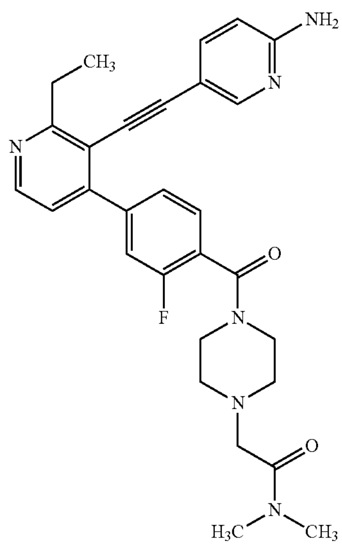 [SMILES: CCc1nccc(-c2ccc(C(=O)N3CCN(CC(=O)N(C)C)CC3)c(F)c2)c1C#Cc1ccc(N)nc1] | A-38 | 514.6 | VB1HUJ00188PA1 | tR = 1.54 |
| 84 | 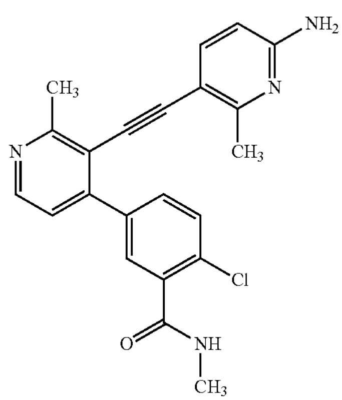 [SMILES: CNC(=O)c1cc(-c2ccnc(C)c2C#Cc2ccc(N)nc2C)ccc1Cl] | | 390.9 | M + H = 391 | tR = 1.45 |

TABLE 1-continued

Examples (cont.)

| No. | Structures | Starting material | MW | [M + H]+ | t_Ret |
|---|---|---|---|---|---|
| 85 | 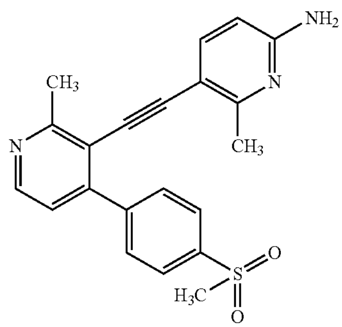 [SMILES: Cc1nc(N)ccc1C#Cc1c(-c2ccc(S(C)(=O)=O)cc2)ccnc1C] | | 377.5 | M + H = 378 | tR = 1.47 |
| 86 | 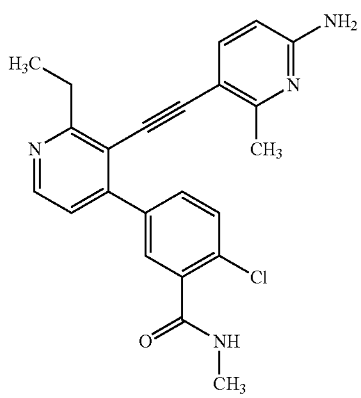 [SMILES: CCc1nccc(-c2ccc(Cl)c(C(=O)NC)c2)c1C#Cc1ccc(N)nc1C] | | 404.9 | M + H = 405 | tR = 1.55 |
| 87 | 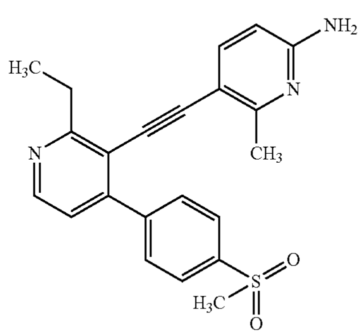 [SMILES: CCc1nccc(-c2ccc(S(C)(=O)=O)cc2)c1C#Cc1ccc(N)nc1C] | | 391.5 | M + H = 392 | tR = 1.58 |
| 88 | 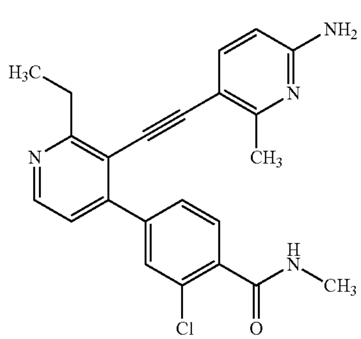 [SMILES: CCc1nccc(-c2ccc(C(=O)NC)c(Cl)c2)c1C#Cc1ccc(N)nc1C] | | 404.9 | M + H = 405 | tR = 1.56 |

TABLE 1-continued
Examples (cont.)
| No. | Structures | Starting material | MW | [M + H]+ | t_Ret |
|---|---|---|---|---|---|
| 89 | 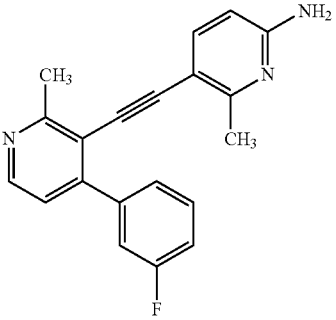 [SMILES: Cc1nc(N)ccc1C#Cc1c(-c2cccc(F)c2)ccnc1C] |  | 317.4 | M + H = 318 | tR = 1.73 |
| 90 | 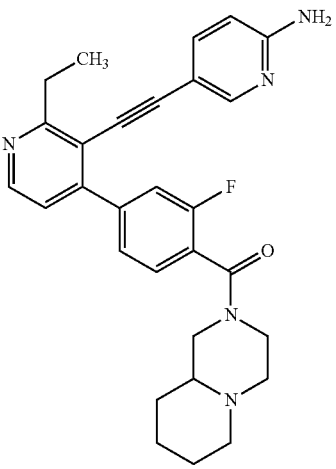 [SMILES: CCc1nccc(-c2ccc(C(=O)N3CCN4CCCCC4C3)c(F)c2)c1C#Cc1ccc(N)nc1] | A-38 | 483.6 | M + H = 484 | tR = 1.75 |
| 91 | 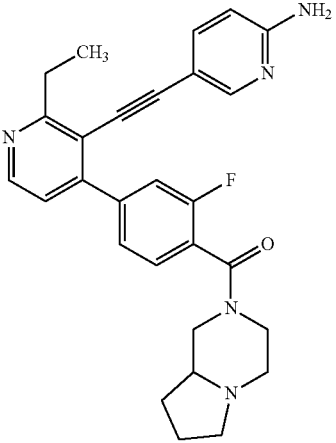 [SMILES: CCc1nccc(-c2ccc(C(=O)N3CCN4CCCC4C3)c(F)c2)c1C#Cc1ccc(N)nc1] | A-38 | 469.6 | M + H = 470 | tR = 1.68 |

TABLE 1-continued

Examples (cont.)

| No. | Structures | Starting material | MW | [M + H]+ | t$_{Ret}$ |
|---|---|---|---|---|---|
| 92 | 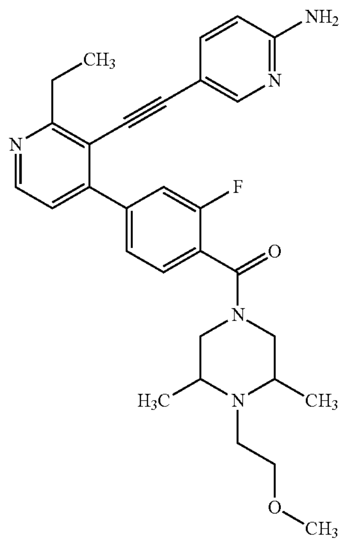 [SMILES: CCc1nccc(-c2ccc(C(=O)N3CC(C)N(CCOC)C(C)C3)c(F)c2)c1C#Cc1ccc(N)nc1] | A-38 | 515.6 | M + H = 516 | tR = 1.74 |
| 93 | 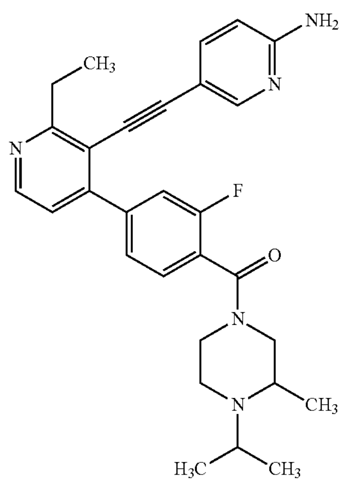 [SMILES: CCc1nccc(-c2ccc(C(=O)N3CCN(C(C)C)C(C)C3)c(F)c2)c1C#Cc1ccc(N)nc1] | A-38 | 485.6 | M + H = 486 | tR = 1.80 |
| 94 | 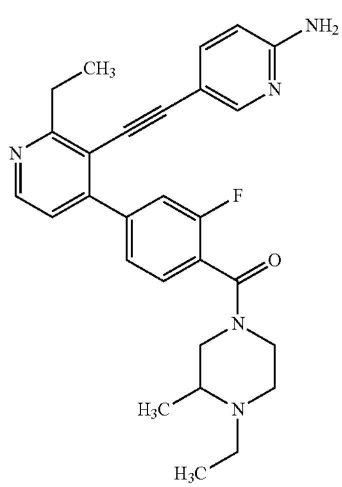 [SMILES: CCc1nccc(-c2ccc(C(=O)N3CCN(CC)C(C)C3)c(F)c2)c1C#Cc1ccc(N)nc1] | A-38 | 471.6 | M + H = 472 | tR = 1.70 |

TABLE 1-continued

Examples (cont.)

| No. | Structures | Starting material | MW | [M + H]+ | t$_{Ret}$ |
|---|---|---|---|---|---|
| 95 | 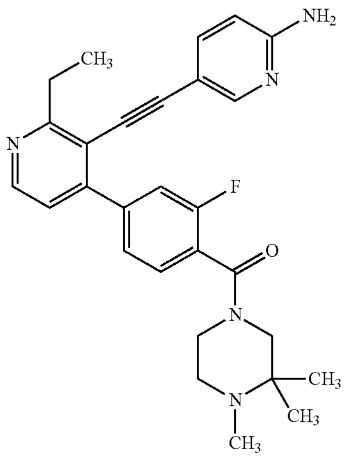 [SMILES: CCc1nccc(-c2ccc(C(=O)N3CCN(C)C(C)(C)C3)c(F)c2)c1C#Cc1ccc(N)nc1] | A-38 | 471.6 | M + H = 472 | tR = 1.66 |
| 96 | 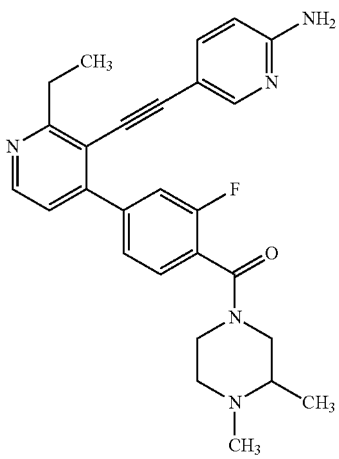 [SMILES: CCc1nccc(-c2ccc(C(=O)N3CCN(C)C(C)C3)c(F)c2)c1C#Cc1ccc(N)nc1] | A-38 | 457.6 | M + H = 458 | tR = 1.62 |
| 97 | Chiral | A-38 | 455.5 | M + H = 456 (389) | tR = 1.50 (1.56) |

TABLE 1-continued

Examples (cont.)

| No. | Structures | Starting material | MW | [M + H]+ | t$_{Ret}$ |
|---|---|---|---|---|---|
| 98 | (structure, Chiral) | A-38 | 535.6 | M + H = 536 | tR = 1.91 |
| 99 | (structure) | | 446.5 | | |
| 100 | (structure) | | 457.6 | M + H = 458 | tR = 1.62 |

TABLE 1-continued
Examples (cont.)
| No. | Structures | Starting material | MW | [M + H]⁺ | t_Ret |
|---|---|---|---|---|---|
| 101 | 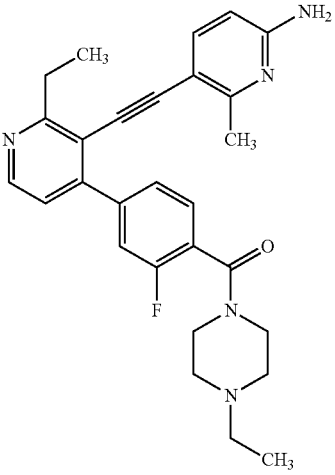 [SMILES: CCc1nccc(-c2ccc(C(=O)N3CCN(CC)CC3)c(F)c2)c1C#Cc1ccc(N)nc1C] | | 471.6 | M + H = 472 | tR = 1.70 |
| 102 | 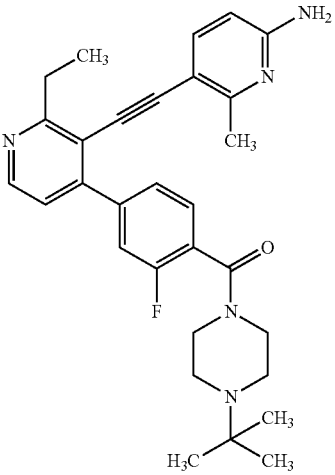 [SMILES: CCc1nccc(-c2ccc(C(=O)N3CCN(C(C)(C)C)CC3)c(F)c2)c1C#Cc1ccc(N)nc1C] | | 499.6 | M + H = 500 | tR = 1.86 |
| 103 | 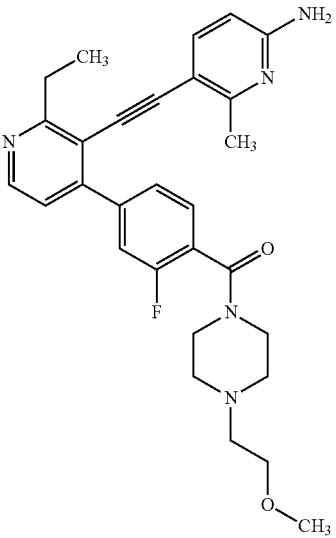 [SMILES: CCc1nccc(-c2ccc(C(=O)N3CCN(CCOC)CC3)c(F)c2)c1C#Cc1ccc(N)nc1C] | | 501.6 | M + H = 502 | tR = 1.64 |

TABLE 1-continued

Examples (cont.)

| No. | Structures | Starting material | MW | [M + H]⁺ | $t_{Ret}$ |
|---|---|---|---|---|---|
| 104 | 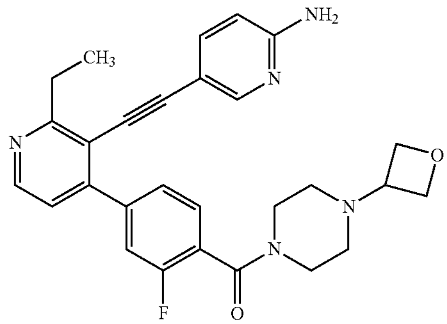 [SMILES: CCc1nccc(-c2ccc(C(=O)N3CCN(C4COC4)CC3)c(F)c2)c1C#Cc1ccc(N)nc1] | A-38 | 485.6 | M + H = 486 | tR = 1.51 |
| 105 | 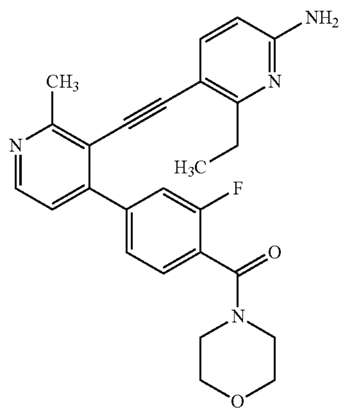 [SMILES: CCc1nc(N)ccc1C#Cc1c(-c2ccc(C(=O)N3CCOCC3)c(F)c2)ccnc1C] | | 444.5 | M + H = 445 | tR = 1.57 |
| 106 | 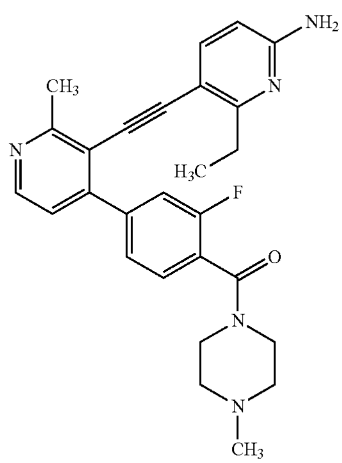 [SMILES: CCc1nc(N)ccc1C#Cc1c(-c2ccc(C(=O)N3CCN(C)CC3)c(F)c2)ccnc1C] | | 457.6 | M + H = 458 | tR = 1.57 |
| 107 | 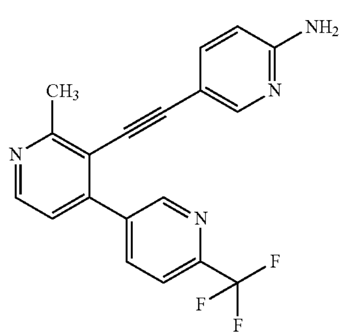 [SMILES: Cc1nccc(-c2ccc(C(F)(F)F)nc2)c1C#Cc1ccc(N)nc1] | A-28 | 354.3 | M + H = 355 | tR = 1.61 |

TABLE 1-continued

Examples (cont.)

| No. | Structures | Starting material | MW | [M + H]+ | t_Ret |
|---|---|---|---|---|---|
| 108 | 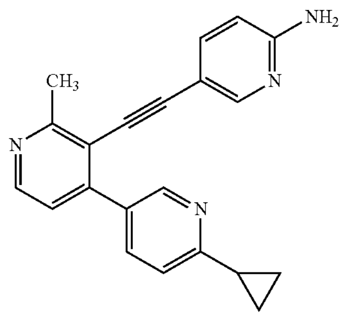 [SMILES: Cc1nccc(-c2ccc(C3CC3)nc2)c1C#Cc1ccc(N)nc1] | A-28 | 326.4 | M + H = 327 | tR = 1.57 |
| 109 | 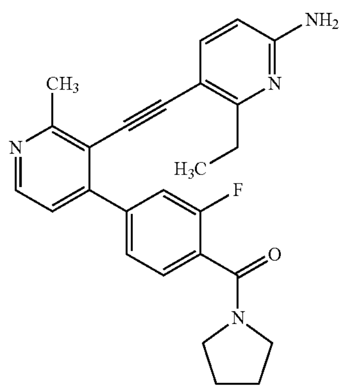 [SMILES: CCc1nc(N)ccc1C#Cc1c(-c2ccc(C(=O)N3CCCC3)c(F)c2)ccnc1C] | | 428.5 | M + H = 429 | tR = 1.70 |
| 110 | 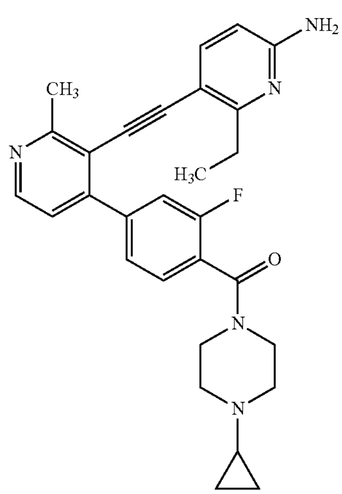 [SMILES: CCc1nc(N)ccc1C#Cc1c(-c2ccc(C(=O)N3CCN(C4CC4)CC3)c(F)c2)ccnc1C] | | 483.6 | M + H = 484 | tR = 1.77 |

TABLE 1-continued

Examples (cont.)

| No. | Structures | Starting material | MW | [M + H]⁺ | $t_{Ret}$ |
|---|---|---|---|---|---|
| 111 | 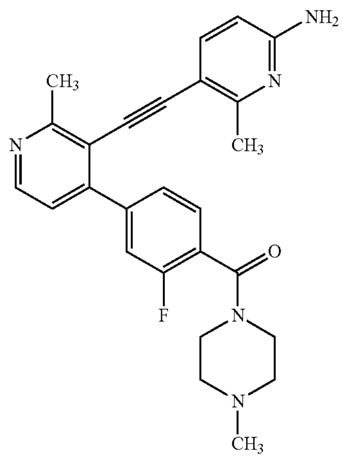 [SMILES: Cc1nc(N)ccc1C#Cc1c(-c2ccc(C(=O)N3CCN(C)CC3)c(F)c2)ccnc1C] | | 443.5 | M + H = 444 | tR = 1.50 |
| 112 | 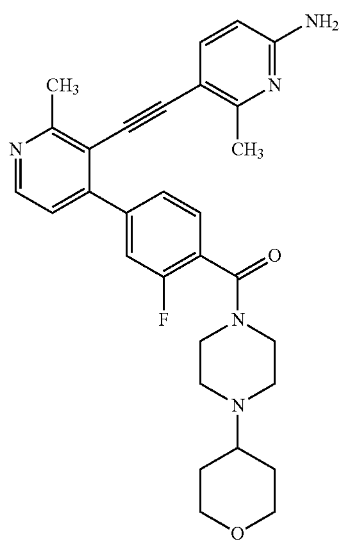 [SMILES: Cc1nc(N)ccc1C#Cc1c(-c2ccc(C(=O)N3CCN(C4CCOCC4)CC3)c(F)c2)ccnc1C] | | 513.6 | M + H = 514 | tR = 1.63 |
| 113 | 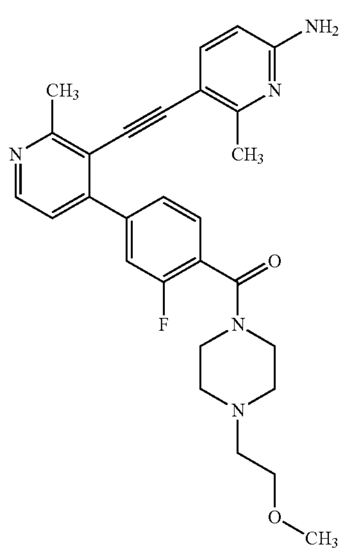 [SMILES: COCCN1CCN(C(=O)c2ccc(-c3ccnc(C)c3C#Cc3ccc(N)nc3C)cc2F)CC1] | | 487.6 | M + H = 488 | tR = 1.56 |

TABLE 1-continued

| | | Starting | | | |
|---|---|---|---|---|---|
| No. | Structures | material | MW | [M + H]⁺ | $t_{Ret}$ |
| 114 | | | 485.6 | M + H = 486 | tR = 1.77 |
| 115 | | | 457.6 | M + H = 458 | tR = 1.60 |
| 116 | | A-46 | 499.6 | M + H = 500 | tR = 1.97 |

TABLE 1-continued
Examples (cont.)
| No. | Structures | Starting material | MW | [M + H]⁺ | $t_{Ret}$ |
|---|---|---|---|---|---|
| 117 | 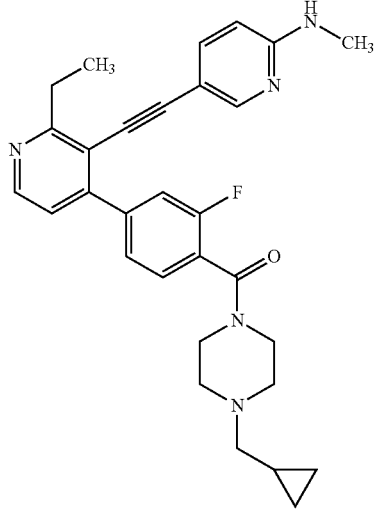 [SMILES: CCc1nccc(-c2ccc(C(=O)N3CCN(CC4CC4)CC3)c(F)c2)c1C#Cc1ccc(NC)nc1] | A-46 | 497.6 | M + H = 498 | tR = 1.92 |
| 118 | 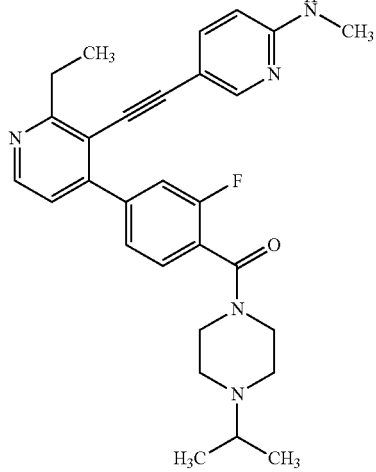 | A-46 | 485.6 | M + H = 486 | tR = 1.90 |
| 119 | 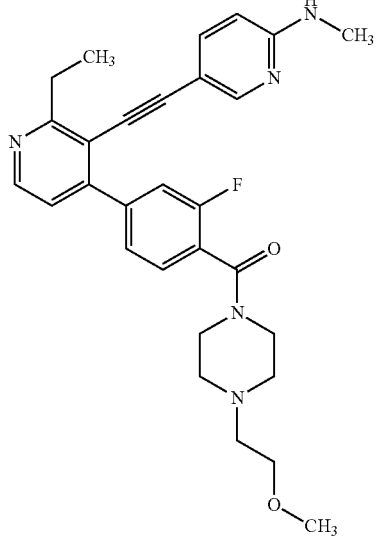 | A-46 | 501.6 | M + H = 502 | tR = 1.75 |

TABLE 1-continued

Examples (cont.)

| No. | Structures | Starting material | MW | [M + H]+ | t_Ret |
|---|---|---|---|---|---|
| 120 | 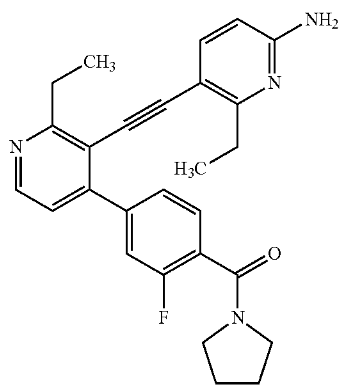 [SMILES: CCc1nc(N)ccc1C#Cc1c(-c2ccc(C(=O)N3CCCC3)c(F)c2)ccnc1CC] | A-44 | 442.5 | M + H = 443 | tR = 1.79 |
| 121 | 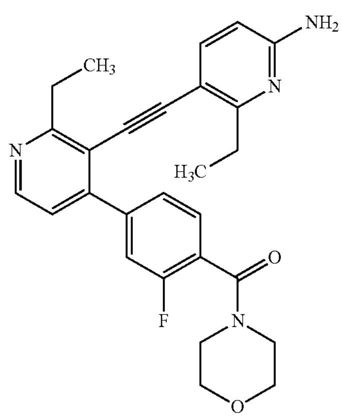 [SMILES: CCc1nc(N)ccc1C#Cc1c(-c2ccc(C(=O)N3CCOCC3)c(F)c2)ccnc1CC] | A-44 | 458.5 | M + H = 459 | tR = 1.69 |
| 122 | 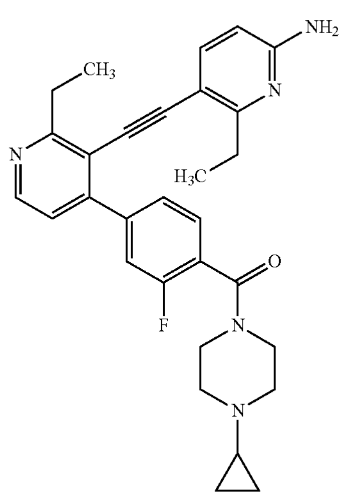 [SMILES: CCc1nc(N)ccc1C#Cc1c(-c2ccc(C(=O)N3CCN(C4CC4)CC3)c(F)c2)ccnc1CC] | A-44 | 497.6 | M + H = 498 | tR = 1.88 |

TABLE 1-continued

Examples (cont.)

| No. | Structures | Starting material | MW | [M + H]+ | t_Ret |
|---|---|---|---|---|---|
| 123 | 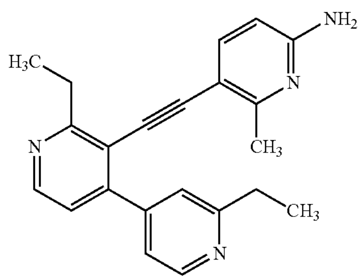 [SMILES: CCc1cc(-c2ccnc(CC)c2C#Cc2ccc(N)nc2C)ccn1] | | 342.4 | M + H = 343 | tR = 1.81 |
| 124 | 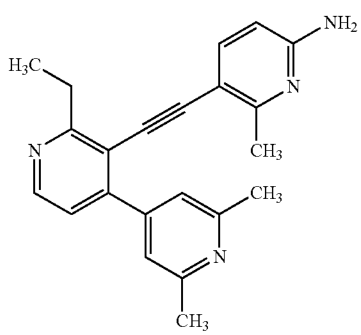 [SMILES: CCc1nccc(-c2cc(C)nc(C)c2)c1C#Cc1ccc(N)nc1C] | | 342.4 | M + H = 343 | tR = 1.70 |
| 125 | 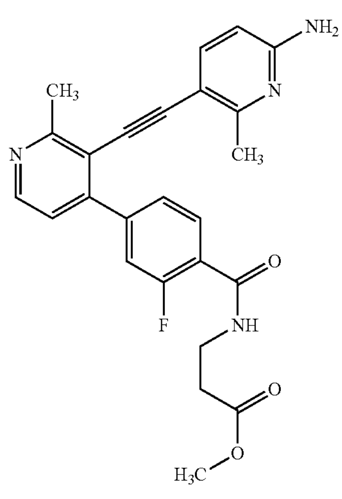 [SMILES: COC(=O)CCNC(=O)c1ccc(-c2ccnc(C)c2C#Cc2ccc(N)nc2C)cc1F] | | 446.5 | M + H = 447 | tR = 1.60 |

TABLE 1-continued
Examples (cont.)
| No. | Structures | Starting material | MW | [M + H]+ | t$_{Ret}$ |
|---|---|---|---|---|---|
| 126 | 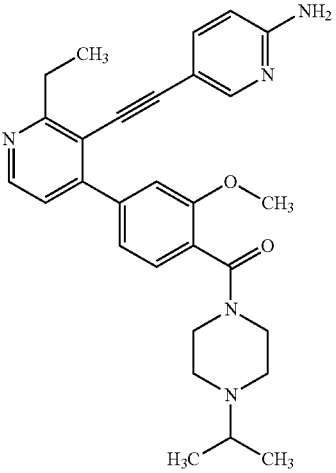 [SMILES: CCc1nccc(-c2ccc(C(=O)N3CCN(C(C)C)CC3)c(OC)c2)c1C#Cc1ccc(N)nc1] | A-42 | 483.6 | M + H = 484 | tR = 1.79 |
| 127 | 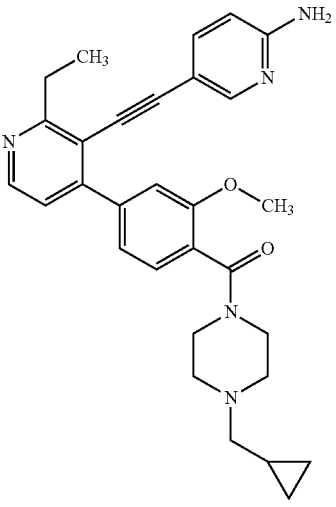 [SMILES: CCc1nccc(-c2ccc(C(=O)N3CCN(CC4CC4)CC3)c(OC)c2)c1C#Cc1ccc(N)nc1] | A-42 | 495.6 | M + H = 469 | tR = 1.82 |
| 128 | 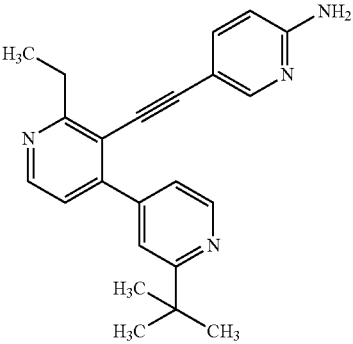 [SMILES: CCc1nccc(-c2ccnc(C(C)(C)C)c2)c1C#Cc1ccc(N)nc1] | A-38 | 356.5 | M + H = 357 | tR = 1.89 |

TABLE 1-continued

Examples (cont.)

| No. | Structures | Starting material | MW | [M + H]⁺ | $t_{Ret}$ |
|---|---|---|---|---|---|
| 129 | (structure) | A-42 | 483.6 | M + H = 484 | tR = 1.77 |
| 130 | (structure) | A-42 | 455.5 | M + H = 456 | tR = 1.42 |

Analytical Methods
HPLC: Agilent 1100 Series
MS: Agilent LC/MSD SL
column: Phenomenex, Mercury Gemini C18, 3 μm, 2.0×20 mm, Part. No. 00M-4439-B0-CE
solvent
  A: 5 mM NH₄HCO₃/20 mM NH₃
  B: acetonitrile HPLC grade
detection:
  MS: Positive and negative
  mass range: 120-700 m/z
  fragmentor: 70
  gain EMV: 1
  threshold: 150
  stepsize: 0.25
  UV: 315 nm
  bandwidth: 170 nm
  reference: off
  range: 210-400 nm
  range step: 2.00 nm
  peakwidth: <0.01 min
  slit: 2 nm injection: 5 μL
flow: 1.00 mL/min
column temperature: 40° C.
gradient:

| | |
|---|---|
| 0.00 min | 5% B |
| 0.00-2.50 min | 5% –> 95% B |
| 2.50-2.80 min | 95% B |
| 2.81-3.10 min | 95% –> 5% B |

Analytical Method 2
Instrument: Agilent 1100-SL: incl. ELSD/DAD/MSD
Chromatography:
  Column: Phenomenex Gemini® C18, 50×2.0 mm, 3μ
Method "Acid"
  Eluent A: 0.1% formic acid in acetonitrile
  Eluent B: 0.1% formic acid in Water
  Linear Gradient program: $t_0$=2% A, $t_{3.5min}$=98% A, $t_{6min}$=98% A
  Flow: 1 mL/min
  Column oven temperature: 35° C.

Method "Base"
 Eluent A: 10 mM ammonia in acetonitrile
 Eluent B: 10 mM ammonia in water
 Linear Gradient program: $t_0$=2% A, $t_{3.5min}$=98% A, $t_{6min}$=98% A
 Flow: 1 mL/min
 Column oven temperature: 35° C.
Evaporative Light Scattering Detector (ELSD):
 Instrument: Polymer Laboratories PL-ELS 2100
 Nebuliser gas flow: 1.1 L/min $N_2$
 Nebuliser temp: 50° C.
 Evaporation temp: 80° C.
 Lamp: Blue LED 480 nm
Diode Array Detector (DAD):
 Instrument: Agilent G1316A
 Sample wavelength: 220-320 nm
 Reference wavelength: Off
Mass Spectroscopy (MSD):
 Instrument: Agilent LC/MSD-SL
 Ionisation: ESI (Positive & Negative)
 Mass range: 100-800

ABBREVIATIONS USED

| ACN | acetonitrile | Me | methyl |
|---|---|---|---|
| bu | butyl | min | minute(s) |
| CDI | carbonyl diimidazole | mL | millilitre |
| d | day(s) | MeOH | methanole |
| DC | thin layer chromatography | MS | mass spectrometry |
| DCM | dichloromethane | N | normal |
| DIPEA | diisopropylethyl amine | NIS | N-iodosuccinimide |
| DME | 1,2-dimethoxyethane | NMP | N-methylpyrrolindinone |
| DMF | N,N-dimethylformamide | NMR | nuclear resonance spectroscopy |
| DMSO | dimethylsulphoxide | NP | normal phase |
| EDC | 1-Ethyl-3-(3-dimethylamino-propyl)carbodiimide (hydrochloride) | ppm | part per million |
| Et | ethyl | Rf | retention factor |
| h | hour(s) | RP | reversed phase |
| HATU | O-(7-Azabenzotriazol-1-yl)-N,N,N',N'-tetramethyluronium hexafluorophosphate | prep | preparative |
| HOBt | 1-Hydroxybenzotriazole | RT | room temperature |
| HPLC | high performance liquid chromatography | tert | tertiary |
| iPr | isopropyl | $t_{Ret}$ | retention time |
| LC | liquid chromatography | THF | tetrahydrofuran |
| M | molar | TMS | tetramethylsilanyl |
| | | XPhos | 2-Dicyclohexyl-phosphino-2',4',6'-triisopropylbiphenyl |

The Examples that follow describe the biological activity of the compounds according to the invention without restricting the invention to these Examples.
Inhibition of Proliferation: CyQuant PC-3
Description:
 The CyQuant NF assay is based on measurement of cellular DNA content via fluorescent dye binding. Because cellular DNA content is highly regulated, it is closely proportional to cell number. The extent of proliferation is determined by comparing cell counts for samples treated with drugs with untreated controls. The assay is not dependent on physiological activities that may exhibit cell number-independent variability.
 In the assay, a DNA-binding dye in combination with a plasma membrane permeabilization reagent is used. The medium is aspirated, replaced with dye binding solution, cells are incubated for 30-60 min, then fluorescence is measured (excitation at 485 nm, emission detection at 530 nm). Data are expressed as fluorescence emission intensity units as a function of time of incubation.
Cells and Reagents:
 PC-3 cells Human prostate carcinoma cells (ATCC CRL-1435)
 CyQuant NF assay Invitrogen Cat. #C35006
 PBS (w/o Ca, Mg) Life Technologies, Gibco BRL (Cat. No. 4190-094)
 F-12K Medium Life Technologies, Gibco BRL (Cat. No. 21127-022)
 Fetal calf serum Life Technologies, Gibco BRL (Cat. No. 10270-106)
Equipment:
 96-well plates, flat bottom (Falcon, Cat. No.: 353072)
 96-well plates, U-shaped (Costar, Cat. No.: 3799)
 $CO_2$-Incubator
 Microplate Reader, Wallac Victor
Procedure:
 Day 0: Seed 3000 PC-3 cells (cultured in F-12K/10% FCS) in 150 IA medium into a 96-well plate, flat bottom (include mediumblank). Incubate plates at 37° C. in a $CO_2$ incubator overnight.
 Day 1: Dilute compounds to a concentration 80 µM→1:5 in medium, 7 dilution steps, in 96-well plates.
  Add 50 µl per well of each dilution (total volume per well 2001.11; final conc. of cpds: 20 µM→1:5). If required, test further dilutions.
 All concentrations are tested in duplicates or triplicates.
 Controls: Cells w/o cpd. (+50 µl medium+DMSO).
 Cells are incubated with compounds for 3 days.
 Day 4: Aspirate off medium and replace with 100 µl of 1× dye binding solution (22 µl CyQuant NF dye reagent added to 11 ml of 1×HBSS buffer). Cover the microplate and incubate for 30-60 min for equilibration of dye-DNA binding.
 Measure the fluorescence intensity in a microplate reader (excitation at 485 nm, emission detection at 530 nm).
Evaluation:
 Calculate $IC_{50}$ using GraphPad Prism (Fifty)
Inhibition of mTOR-Induced p-4E-BP1 Phosphorylation (TR-FRET mTOR Activity Kit; Invitrogen)
Materials:
 GFP-4E-BP1 substrate; Invitrogen order no. PV4759
 Lanthascreen Tb-anti-p4E-BP1 (pThr46) Antibody Kit; Invitrogen order no. PV4758
 FRAP1 (mTOR) kinase; Invitrogen order no. PV4753
 ATP 10 mM
 5× Assay Buffer (250 mM HEPES pH7.5, 0.05% Polysorbate 20, 5 mM EGTA, 50 mM MnCl2)
 EDTA 500 mM
Determining IC50 Values for Test Compounds:
Kinase Reaction Conditions:
400 nM GFP-4E-BP1, 8 µM ATP, ~150 ng/mL mTOR, 50 mM HEPES pH 7.5, 0.01% Polysorbate 20, 1 mM EGTA, 10 mM MnCl2, and variable amounts of test compounds.
 Preparation of Reagents:
 Note: Thaw and keep mTOR, the substrate, ATP, and the antibody on ice prior to making working dilutions. Working dilutions of these components can be kept at room temperature for short periods of time the day of use.

1. Add 2 ml of 5× Assay Buffer to 8 ml water to prepare 10 ml of 1× Assay Buffer.
Note: The concentration of 1× Assay Buffer is 50 mM HEPES pH 7.5, 0.01% Polysorbate 20, 1 mM EGTA, and 10 mM MnCl2.
2. Prepare Antibody/EDTA Solution by first adding 2.75 µl of Tb-anti p4E-BP1 Antibody to 2397 µl of LanthaScreen™ TR-FRET Dilution Buffer. Then, add 100 µl of 0.5 M EDTA.
3. Prepare 4× Substrate/Enzyme Solution by first adding 72 µl of GFP-4E-BP1 (22 µM) to 926 µl of 1× Assay Buffer. Then, add 1.6 µl of mTOR (0.45 mg/mL).
4. Prepare ATP Solution by adding 3.2 µl of 10 mM ATP to 1997 µl of 1× Assay Buffer.

Serial Dilution of Inhibitors (16 Point Curve):
Note: It is recommended that inhibitors be serially diluted in DMSO, then diluted to a 4× working concentration with 1× Assay Buffer. The below procedure describes dilution of compounds in a 96-well format prior to transfer to a 384-well format for kinase assays. This procedure calls for dilution of the compounds in 2 adjacent columns of a 96-well plate, which upon transfer to a single column of a 384-well plate with an 8-channel pipette will align the samples in order of concentration.
  1. Dispense 40 µl of DMSO to two adjacent columns of a 96 well plate per compound (e.g. columns 1 and 2).
  2. Add 10 µl of inhibitor stock (10 mM) to the first well of the first column (A1) and mix.
  3. Remove 10 µl from A1 and transfer to the adjacent well in the next column (B1) and mix.
  4. Remove 10 µl from B1 and transfer to the next well in the first column (B2) and mix.
  5. Repeat this dilution pattern through well H1 and leave the last well (H2) as DMSO only.
  6. Remove 4 µl of diluted compounds and add to 96 µl of 1× Assay Buffer in a 96-well plate making 4× compound dilutions.

Kinase Reaction:
  1. Add 2.5 µl of 4× compound dilutions from the first column of the 96-well plate to every other well of column 1 of a 384-well plate with an 8-channel pipette. Repeat for columns 2 and 3.
  2. Add 2.5 µl of 4× compound dilutions from the second column of the 96-well plate to the empty wells of column 1 of the 384-well plate with an 8-channel pipette. Repeat for columns 2 and 3.
  Note: This procedure aligns the compound dilutions in order of concentration.
  3. Add 2.5 µl of 4× Enzyme/Substrate Solution to all columns 1-6.
  4. Preincubate for 30 min. at RT (shaker).
  5. Add 5 µl of ATP Solution to all wells to start reactions.
  6. Shake the assay plate on a plate shaker for 30 seconds.
  7. Incubate the assay plate for one hour at room temperature (20-25° C.).

Stop Step and Fluorescence Detection:
  1. Add 10 µl of Antibody/EDTA Solution to each well in columns 1-9.
  2. Shake the assay plate on a plate shaker for 30 seconds.
  3. Incubate the assay plate for one hour at room temperature (20-25° C.).
  4. Measure the GFP (FRET) and terbium (reference) emission signals on a fluorescence plate reader (e.g. Perkin Elmer Envision).

Data Analysis:
  1. Calculate the emission ratio for each sample by dividing the GFP (FRET) signal by the terbium (reference) signal.
  2. Plot the concentration of each compound versus the emission ratio. Determine the concentration of compound required to reach 50% of the maximum signal (IC50). Determination of IC50 values can be obtained by curve fitting (sigmoidal dose response, variable slope) using Prism software from GraphPad).

TABLE 2

Biological data

| Example | mTOR (IC50) | CQ PC3 (EC50) |
|---|---|---|
| 1 | 0.66 | 45 |
| 2 | 2 | 44 |
| 3 | 7 | 288 |
| 4 | 7 | 100 |
| 5 | 236 | |
| 6 | 5 | 80 |
| 7 | 4 | 78 |
| 8 | 2 | 44 |
| 9 | 4 | 49 |
| 10 | 3 | 75 |
| 11 | 1 | 56 |
| 12 | 17 | 57 |
| 13 | 8 | 121 |
| 14 | 3 | 65 |
| 15 | 7 | 122 |
| 16 | 7 | 160 |
| 17 | 10 | 97 |
| 18 | 5 | 42 |
| 19 | 93 | |
| 20 | 9 | 248 |
| 21 | 78 | |
| 22 | 47 | 344 |
| 23 | 26 | 214 |
| 24 | 3 | 74 |
| 25 | 4 | 85 |
| 26 | 2 | 25 |
| 27 | | |
| 28 | 11 | 178 |
| 29 | 6 | 161 |
| 30 | 2 | 40 |
| 31 | | |
| 32 | 9 | 310 |
| 33 | 32 | 236 |
| 34 | 4 | 71 |
| 35 | 1 | 30 |
| 36 | | |
| 37 | 5 | 160 |
| 38 | 2 | |
| 39 | 3 | 58 |
| 40 | 207 | 1953 |
| 41 | 497 | 2113 |
| 42 | 4 | 236 |
| 43 | 12 | 355 |
| 44 | 42 | 514 |
| 45 | 6 | 224 |
| 46 | 5 | 188 |
| 47 | 97 | 644 |
| 48 | 4 | 31 |
| 49 | 19 | 394 |
| 50 | 6 | 119 |
| 51 | 20 | 326 |
| 52 | 26 | 617 |
| 53 | 5 | 104 |
| 54 | 35 | 306 |
| 55 | 10 | 200 |
| 56 | 28 | 354 |
| 57 | 9 | 106 |
| 58 | 95 | 519 |
| 59 | 37 | 426 |
| 60 | 3 | 103 |
| 61 | 3 | 275 |
| 62 | 19 | 309 |
| 63 | 23 | 451 |
| 64 | 33 | 470 |
| 65 | 69 | 385 |
| 66 | 60 | 425 |
| 67 | 17 | 156 |

TABLE 2-continued

Biological data

| Example | mTOR (IC50) | CQ PC3 (EC50) |
|---|---|---|
| 68 | 88 | 429 |
| 69 | 28 | 206 |
| 70 | 20 | 130 |
| 71 | 105 | 343 |
| 72 | 21 | 186 |
| 73 | 2 | 131 |
| 74 | 2 | 69 |
| 75 | 7 | 110 |
| 76 | 2 | 35 |
| 77 | 10 | 100 |
| 78 | 3 | 81 |
| 79 | 2 | 55 |
| 80 | 2 | 114 |
| 81 | 2 | 54 |
| 82 | 2 | 40 |
| 83 | 2 | 75 |
| 84 | 85 | 688 |
| 85 | 5 | 136 |
| 86 | 77 | 694 |
| 87 | 5 | 45 |
| 88 | 4 | 86 |
| 89 | 113 | 537 |
| 90 | 4 | 79 |
| 91 | 3 | 35 |
| 92 | 9 | 109 |
| 93 | 10 | 70 |
| 94 | 9 | 134 |
| 95 | 9 | 58 |
| 96 | 6 | 59 |
| 97 | 9 | 121 |
| 98 | 42 | 185 |
| 99 | 28 | 548 |
| 100 | 5 | 45 |
| 101 | 38 | 176 |
| 102 | 69 | 66 |
| 103 | 21 | 85 |
| 104 | 4 | 12 |
| 105 | 44 | 121 |
| 106 | 17 | 88 |
| 107 | 27 | 196 |
| 108 | 37 | 237 |
| 109 | 21 | 152 |
| 110 | 11 | 100 |
| 111 | 3 | 50 |
| 112 | 4 | 77 |
| 113 | 5 | 114 |
| 114 | 5 | 84 |
| 115 | 19 | 368 |
| 116 | 10 | 324 |
| 117 | 14 | 566 |
| 118 | 13 | 247 |
| 119 | 13 | 255 |
| 120 | 79 | 149 |
| 121 | 41 | 166 |
| 122 | 96 | 126 |
| 123 | 44 | 616 |
| 124 | 15 | 84 |
| 125 | 24 | 425 |
| 126 | 33 | 256 |
| 127 | 27 | 252 |
| 128 | 56 | 315 |
| 129 | 11 | 237 |
| 130 | 3 | 262 |

The substances of the present invention are PI3 kinase pathway inhibitors, in particular of the serine/threonine kinase mTOR and/or members of the lipid kinase family Pi3K. On account of their biological properties, the novel compounds of the general formula (1) and their isomers and their physiologically tolerated salts are suitable for treating diseases which are characterized by excessive or anomalous cell proliferation. These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:

1. A compound of the formula (1),

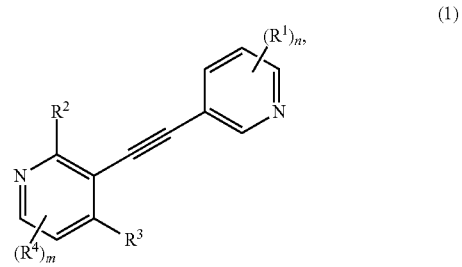

wherein $R^1$ is, in each instance, independently selected from the group consisting of methyl, ethyl, $-NH_2$, $-NHCH_3$ and $-N(CH_3)_2$;

$R^2$ denotes methyl or ethyl;

$R^3$ denotes $C_{6-10}$aryl or 5-12 membered Heteroaryl, optionally substituted by one or more identical or different $R^5$;

each $R^5$ denotes a group selected from among $R^a$, $R^b$ and $R^a$ substituted by one or more identical or different $R^b$ and/or $R^c$; and each $R^a$ independently of one another denotes a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among $=O$, $-OR^c$, $C_{1-3}$haloalkyloxy, $-OCF_3$, $=S$, $-SR^c$, $=NR^c$, $=NOR^c$, $=NNR^cR^c$, $=NN(R^g)C(O)$ $NR^cR^c$, $-NR^cR^c$, $-ONR^cR^c$, $-N(OR^c)R^c$, $-N(R^g)$ $NR^cR^c$, halogen, $-CF_3$, $-CN$, $-NC$, $-OCN$, $-SCN$, $-NO$, $-NO_2$, $=N_2$, $-N_3$, $-S(O)R^c$, $-S(O)$ $OR^c$, $-S(O)_2R^c$, $-S(O)_2OR^c$, $-S(O)NR^cR^c$, $-S(O)_2$ $NR^cR^c$, $-OS(O)R^c$, $-OS(O)_2R^c$, $-OS(O)_2OR^c$, $-OS(O)NR^cR^c$, $-OS(O)_2NR^cR^c$, $-C(O)R^c$, $-C(O)$ $OR^c$, $-C(O)SR^c$, $-C(O)NR^cR^c$, $-C(O)N(R^g)NR^cR^c$, $-C(O)N(R^g)OR^c$, $-C(NR^g)NR^cR^c$, $-C(NOH)R^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$, —N(R$^g$)C(NR$^g$)NR$^c$R$^c$ and —N═C(R$^g$)NR$^c$R$^c$ and each R$^e$ independently of one another denotes hydrogen or a group optionally substituted by one or more identical or different R$^d$ and/or R$^e$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$ aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each R$^d$ denotes a suitable group and is selected independently of one another from among ═O, —OR$^e$, C$_{1-3}$haloalkyloxy, —OCF$_3$, ═S, —SR$^e$, ═NR$^e$, ═NOR$^e$, ═NNR$^e$R$^e$, ═NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, ═N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$ and —N═C(R$^g$)NR$^e$R$^e$ each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each R$^f$ denotes a suitable group and in each case is selected independently of one another from among ═O, —OR$^g$, C$_{1-3}$haloalkyloxy, —OCF$_3$, ═S, —SR$^g$, ═NR$^g$, ═NOR$^g$, ═NNR$^g$R$^g$, ═NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, ═N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$; and —N═C(R$^h$)NR$^h$R$^h$; and each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl; and each R$^h$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl; and m denotes 0; and n denotes 0, 1, 2 or 3; and or a tautomer or salt thereof.

2. A compound according to claim 1, wherein R$^3$ denotes phenyl, optionally substituted by one or more identical or different R$^5$.

3. A compound according to claim 1, wherein n denotes 1 or 2.

4. A compound according to claim 1, wherein R$^b$ is —F, —Cl, —CH$_3$, —OCH$_3$, —CF$_3$, —C(O)—R$^c$, —C(O)NR$^c$R$^c$, —C(O)OH, —C(O)OCH$_3$, —C(O)—NH$_2$, —C(O)—NHCH$_3$, —C(O)—N(CH$_3$)$_2$, —S(O)$_2$CH$_3$, or -2-propyl-R$^c$.

5. A compound according to claim 1, wherein R$^e$ is —H, —CN, -methyl, -ethyl, —(CH$_2$)$_2$—OCH$_3$, piperazinyl, piperidinyl, pyrrolidinyl or morpholinyl.

6. A compound according to claim 1, wherein R$^3$ is phenyl substituted with one or more R$^5$, wherein at least one of R$^5$ is —C(O)R$^c$ and wherein R$^c$ is

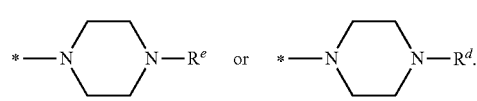

7. A compound according to claim 1, wherein R$^3$ is selected from the group consisting of:

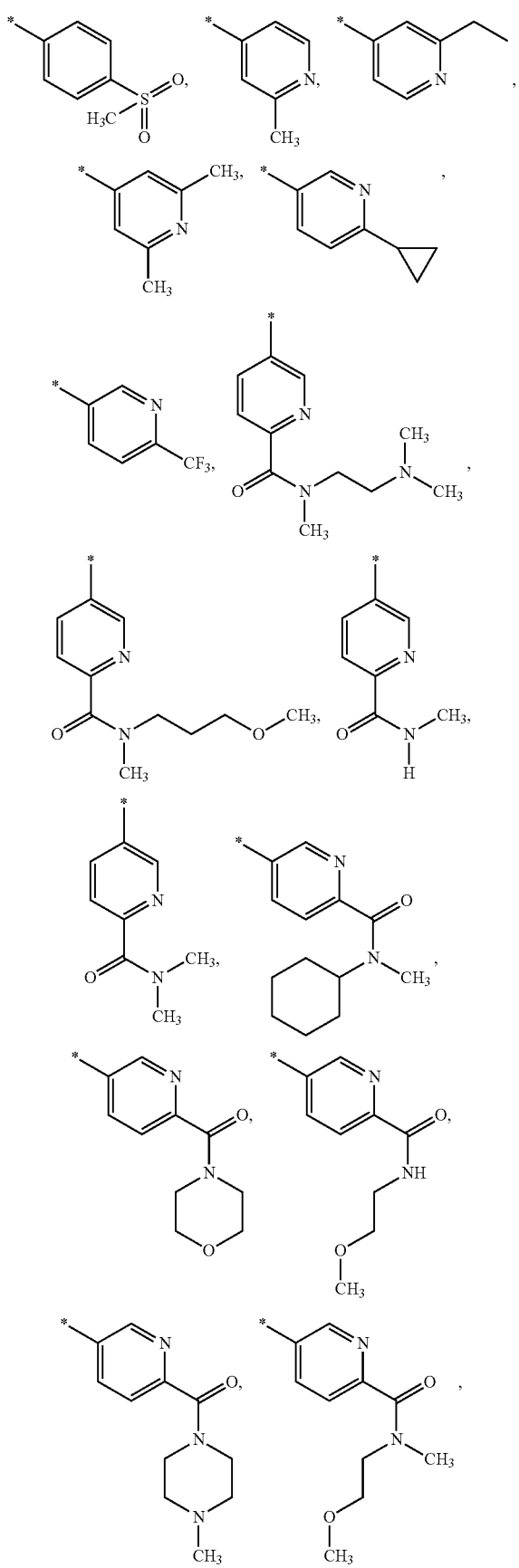
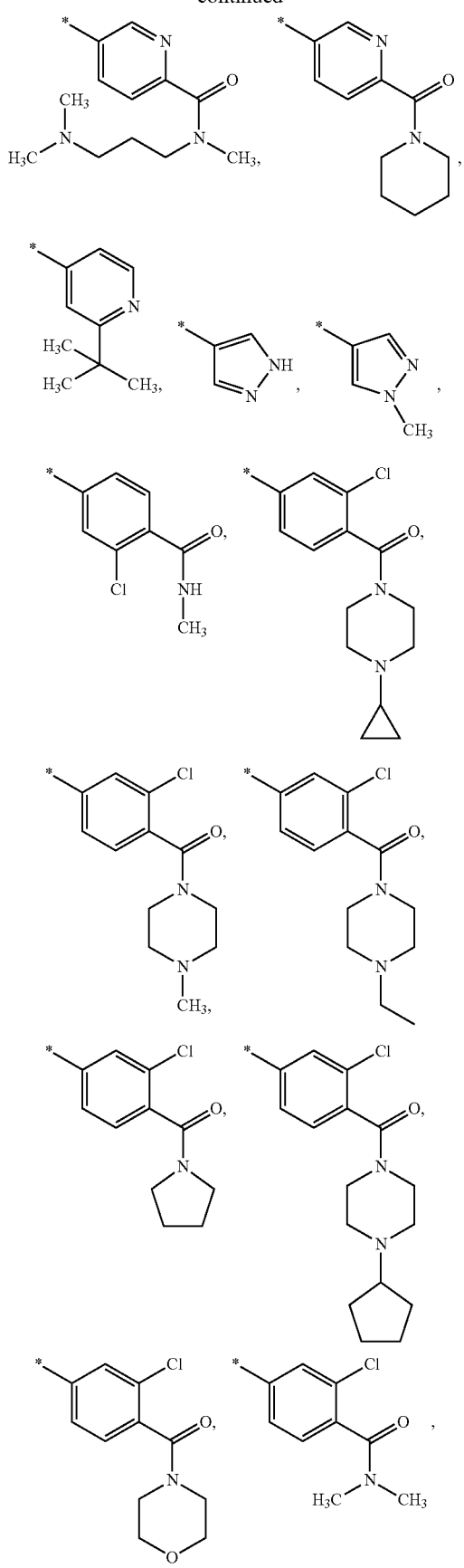

131
-continued
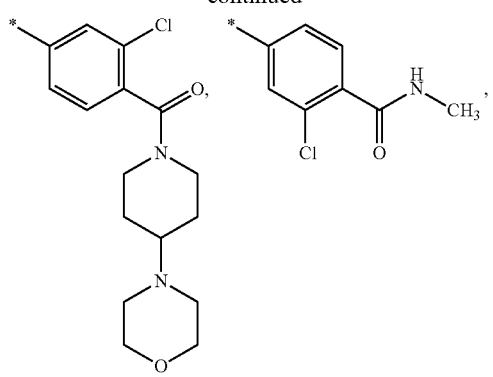
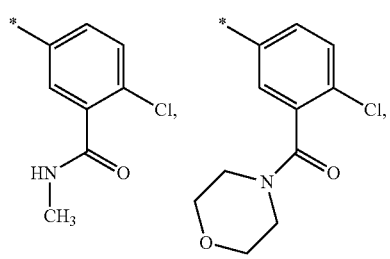
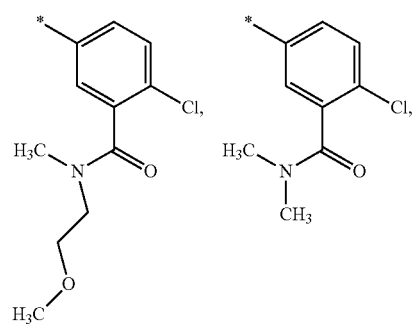
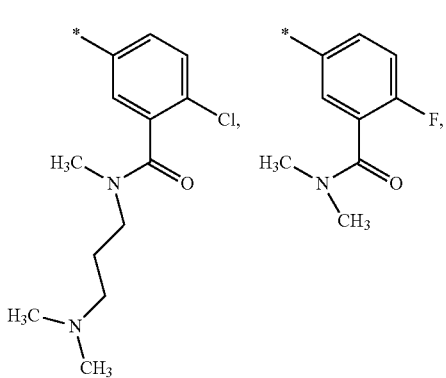
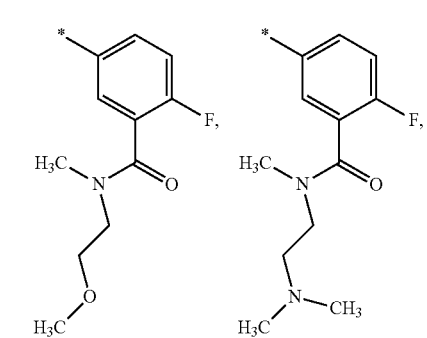
132
-continued
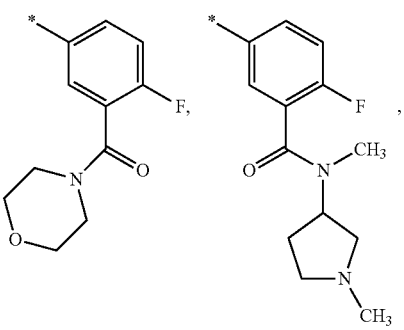
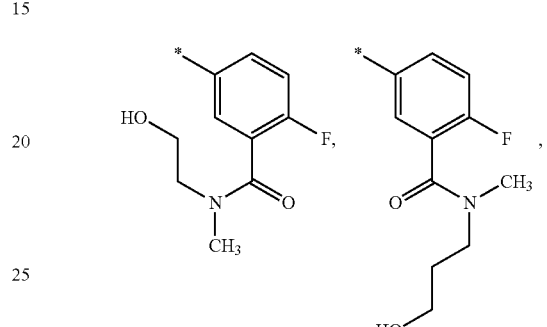
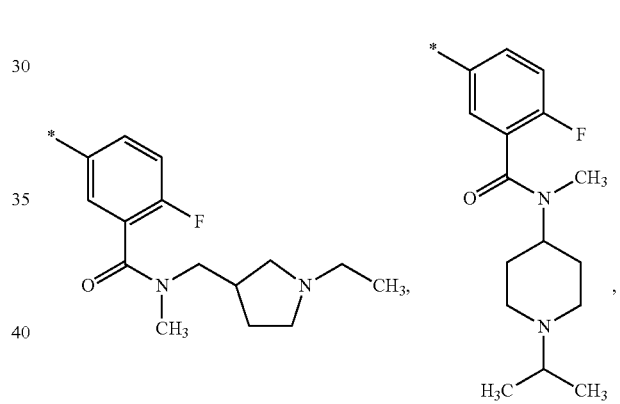
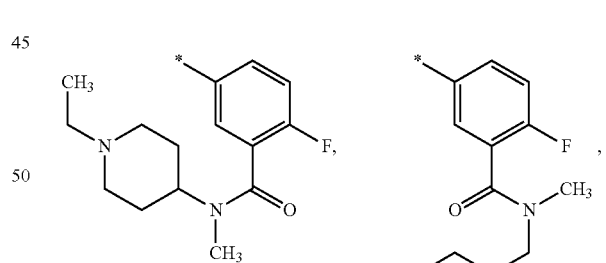
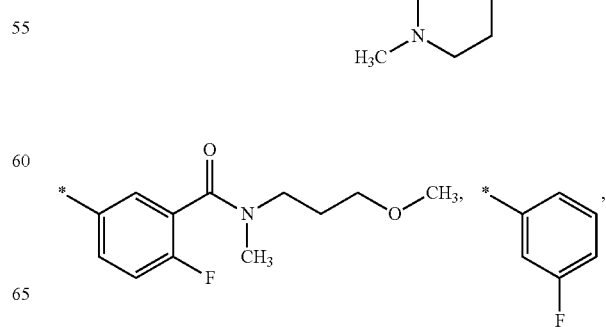

-continued
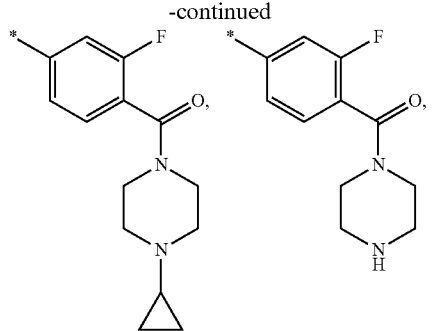
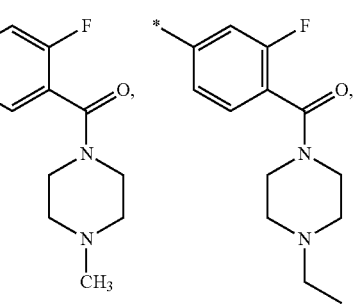
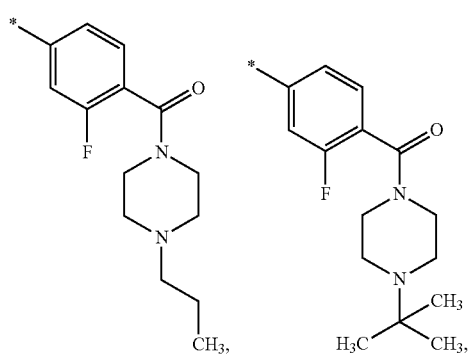
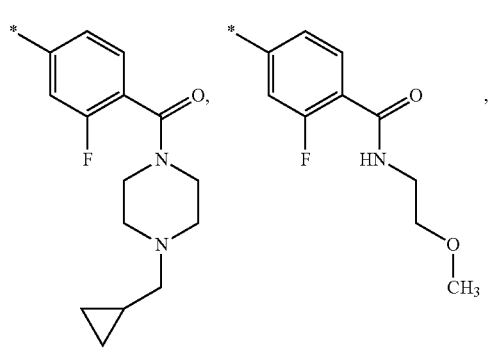
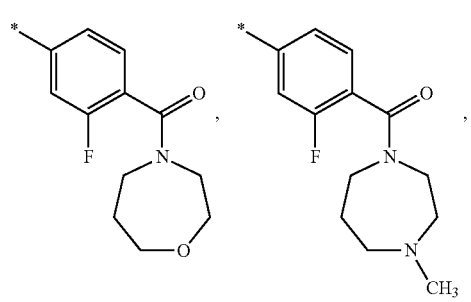
-continued
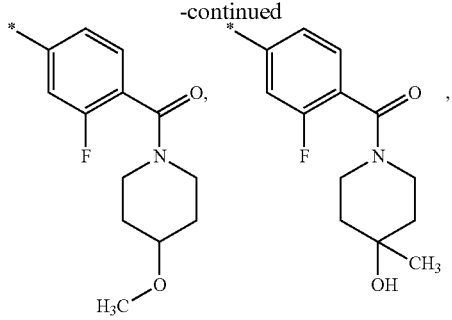
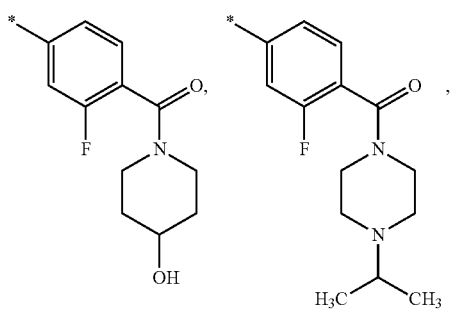
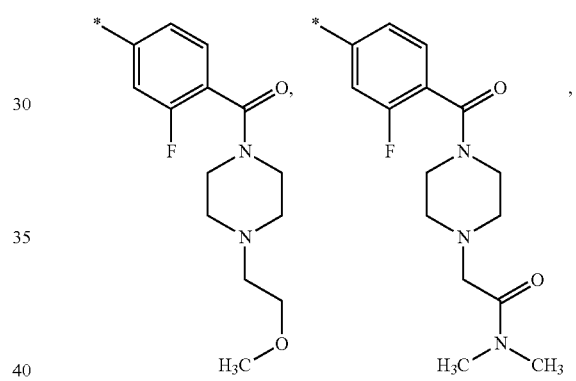
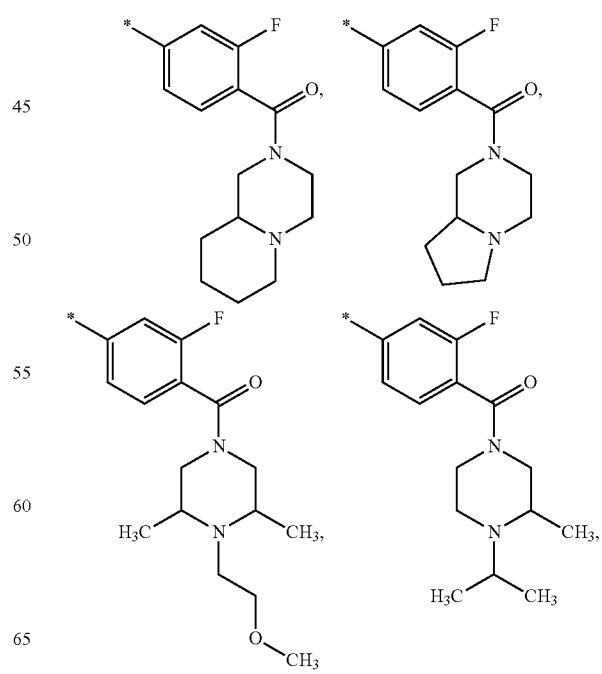

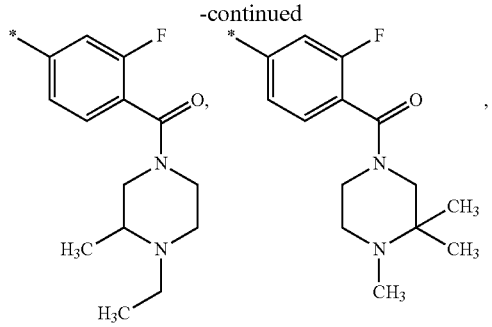
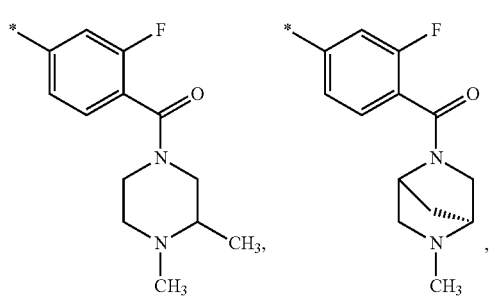
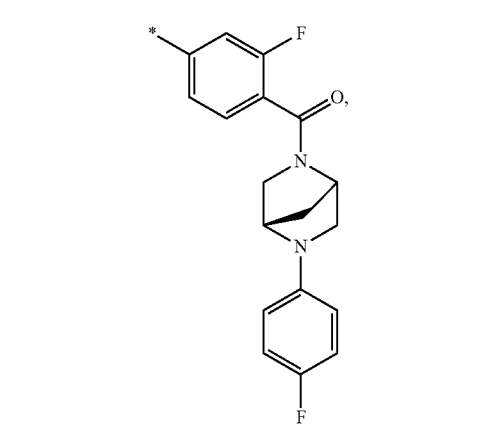
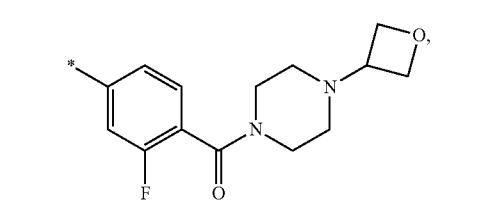
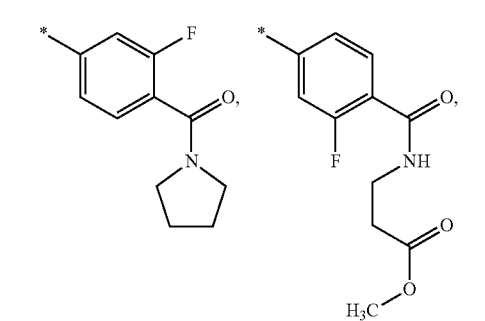

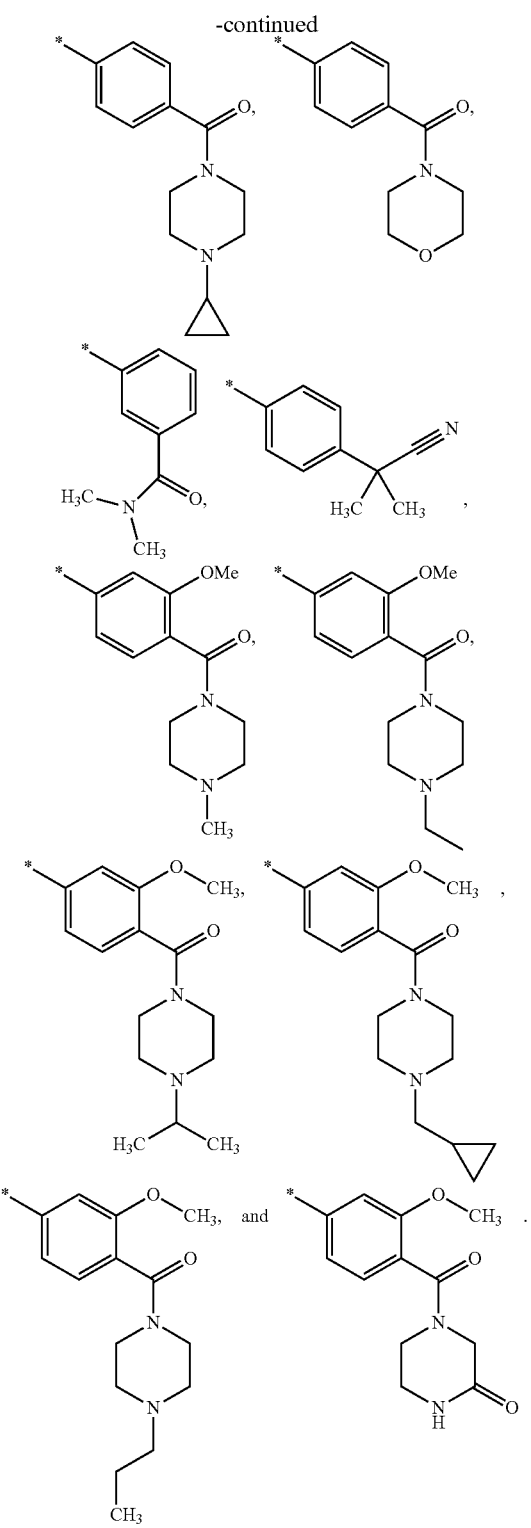

8. A compound selected from the group consisting of:
2-{4-[3-(6-Amino-pyridin-3-ylethynyl)-2-ethyl-pyridin-4-yl]-phenyl}-2-methyl-propionitrile,
5-(2,2'-Diethyl-[4,4']bipyridinyl-3-ylethynyl)-pyridin-2-ylamine,
5-(2-Ethyl-2',6'-dimethyl-[4,4']bipyridinyl-3-ylethynyl)-pyridin-2-ylamine,
5-(6-Cyclopropyl-2'-ethyl-[3,4']bipyridinyl-3'-ylethynyl)-pyridin-2-ylamine,
5-(2'-Ethyl-6-trifluoromethyl-[3,4']bipyridinyl-3'-ylethynyl)-pyridin-2-ylamine,
{4-[3-(6-Amino-pyridin-3-ylethynyl)-2-ethyl-pyridin-4-yl]-2-fluoro-phenyl}-morpholin-4-yl-methanone,
{4-[3-(6-Amino-pyridin-3-ylethynyl)-2-ethyl-pyridin-4-yl]-2-fluoro-phenyl}-piperazin-1-yl-methanone,
{4-[3-(6-Amino-pyridin-3-ylethynyl)-2-ethyl-pyridin-4-yl]-2-fluoro-phenyl}-(4-methyl-piperazin-1-yl)-methanone,
{4-[3-(6-Amino-pyridin-3-ylethynyl)-2-ethyl-pyridin-4-yl]-2-chloro-phenyl}-(4-methyl-piperazin-1-yl)-methanone,
{4-[2-Ethyl-3-(6-methylamino-pyridin-3-ylethynyl)-pyridin-4-yl]-2-fluoro-phenyl}-(4-methyl-piperazin-1-yl)-methanone,
{4-[3-(6-Amino-pyridin-3-ylethynyl)-2-ethyl-pyridin-4-yl]-2-methoxy-phenyl}-(4-methyl-piperazin-1-yl)-methanone,
{4-[3-(6-Amino-pyridin-3-ylethynyl)-2-ethyl-pyridin-4-yl]-2-fluoro-phenyl}-(4-ethyl-piperazin-1-yl)-methanone,
{4-[3-(6-Amino-pyridin-3-ylethynyl)-2-ethyl-pyridin-4-yl]-2-chloro-phenyl}-(4-ethyl-piperazin-1-yl)-methanone,
{4-[2-Ethyl-3-(6-methylamino-pyridin-3-ylethynyl)-pyridin-4-yl]-2-fluoro-phenyl}-(4-ethyl-piperazin-1-yl)-methanone,
{4-[3-(6-Amino-pyridin-3-ylethynyl)-2-ethyl-pyridin-4-yl]-2-methoxy-phenyl}-(4-ethyl-piperazin-1-yl)-methanone,
{4-[3-(6-Amino-pyridin-3-ylethynyl)-2-ethyl-pyridin-4-yl]-2-fluoro-phenyl}-(4-cyclopropyl-piperazin-1-yl)-methanone,
{4-[3-(6-Amino-pyridin-3-ylethynyl)-2-ethyl-pyridin-4-yl]-2-fluoro-phenyl}-[4-(tetrahydro-pyran-4-yl)-piperazin-1-yl]-methanone,
{4-[3-(6-Amino-pyridin-3-ylethynyl)-2-ethyl-pyridin-4-yl]-2-chloro-phenyl}-(4-morpholin-4-yl-piperidin-1-yl)-methanone,
{4-[2-Ethyl-3-(6-methylamino-pyridin-3-ylethynyl)-pyridin-4-yl]-2-fluoro-phenyl}-[4-(tetrahydro-pyran-4-yl)-piperazin-1-yl]-methanone,
1-(4-{4-[3-(6-Amino-pyridin-3-ylethynyl)-2-ethyl-pyridin-4-yl]-2-fluoro-benzoyl}-piperazin-1-yl)-ethanone, and
4-[3-(6-Amino-pyridin-3-ylethynyl)-2-ethyl-pyridin-4-yl]-2-fluoro-N-(2-methoxy-ethyl)-N-methyl-benzamide,
or a salt thereof.

9. A pharmaceutically acceptable salt of a compound according to any one of claim 1 or 8.

10. A pharmaceutical composition comprising a compound according to one of claim 1 or 8 or a pharmaceutically acceptable salt thereof, in combination with a carrier or diluent.

* * * * *